United States Patent [19]
Jautelat et al.

[11] Patent Number: 6,080,775
[45] Date of Patent: Jun. 27, 2000

[54] SULPHONYL-MERCAPTO-TRIAZOLYL DERIVATIVES AND THEIR USE AS MICROBICIDES

[75] Inventors: Manfred Jautelat, Burscheid; Stefan Dutzmann, Langenfeld; Klaus Stenzel, Düsseldorf, all of Germany

[73] Assignee: Bayer Aktiengesellschaft, Leverkusen, Germany

[21] Appl. No.: 09/194,508

[22] PCT Filed: May 12, 1997

[86] PCT No.: PCT/EP97/02408

§ 371 Date: Nov. 19, 1998

§ 102(e) Date: Nov. 19, 1998

[87] PCT Pub. No.: WO97/44332

PCT Pub. Date: Nov. 27, 1997

[30] Foreign Application Priority Data

May 22, 1996 [DE] Germany ............................ 196 20 590

[51] Int. Cl.$^7$ ...................... A01N 43/653; C07D 249/12
[52] U.S. Cl. ........................ 514/384; 548/263.2
[58] Field of Search ........................ 548/263.2; 514/384

[56] References Cited

U.S. PATENT DOCUMENTS

| | | | |
|---|---|---|---|
| 3,912,752 | 10/1975 | Meiser et al. | 260/308 R |
| 3,952,002 | 4/1976 | Kramer et al. | 260/308 R |
| 4,048,318 | 9/1977 | Meiser et al. | 424/269 |
| 4,079,062 | 3/1978 | Van Reet et al. | 260/308 R |
| 4,147,791 | 4/1979 | Meiser et al. | 424/269 |
| 4,205,075 | 5/1980 | Baldwin et al. | 424/269 |
| 4,243,405 | 1/1981 | Balasubramanyan et al. | 71/76 |
| 4,464,381 | 8/1984 | Janssen et al. | 424/269 |
| 4,532,341 | 7/1985 | Holmwood et al. | 549/559 |
| 4,549,900 | 10/1985 | Krämer et al. | 71/92 |
| 4,598,085 | 7/1986 | Heeres et al. | 514/383 |
| 4,626,595 | 12/1986 | Holmwood et al. | 549/559 |
| 4,652,580 | 3/1987 | Janssen et al. | 514/383 |
| 4,723,984 | 2/1988 | Holmwood et al. | 71/76 |
| 4,729,986 | 3/1988 | Olsen | 514/63 |
| 4,789,672 | 12/1988 | Holmwood et al. | 514/184 |
| 4,871,390 | 10/1989 | Holmwood et al. | 71/92 |
| 4,897,107 | 1/1990 | Holmwood et al. | 71/92 |
| 4,904,297 | 2/1990 | Kramer et al. | 71/92 |
| 4,904,298 | 2/1990 | Holmwood et al. | 71/92 |
| 4,906,652 | 3/1990 | Karbach et al. | 514/383 |
| 4,911,746 | 3/1990 | Holmwood et al. | 71/92 |
| 4,913,727 | 4/1990 | Stroech et al. | 71/92 |
| 4,952,232 | 8/1990 | Cuomo et al. | 71/92 |
| 4,965,280 | 10/1990 | Cuomo et al. | 514/383 |
| 4,965,281 | 10/1990 | Cuomo et al. | 514/399 |
| 4,968,712 | 11/1990 | Elbe et al. | 514/383 |
| 4,980,488 | 12/1990 | Stroech et al. | 549/563 |
| 4,988,819 | 1/1991 | Stroech et al. | 548/267.8 |
| 4,990,677 | 2/1991 | Stroech et al. | 568/29 |
| 5,034,052 | 7/1991 | Stroech et al. | 71/92 |
| 5,081,141 | 1/1992 | Colle et al. | 514/383 |
| 5,084,465 | 1/1992 | Cuomo et al. | 514/341 |
| 5,087,635 | 2/1992 | Shaber | 514/383 |
| 5,097,047 | 3/1992 | Stroech et al. | 549/463 |
| 5,256,683 | 10/1993 | Hutt et al. | 514/383 |
| 5,266,585 | 11/1993 | Hubele et al. | 514/383 |
| 5,308,743 | 5/1994 | Hutt et al. | 514/399 |
| 5,639,918 | 6/1997 | Hutt et al. | 568/329 |

FOREIGN PATENT DOCUMENTS

| | | |
|---|---|---|
| 0 015 756 | 9/1980 | European Pat. Off. . |
| 0 069 442 | 2/1985 | European Pat. Off. . |
| 0 44 605 | 2/1986 | European Pat. Off. . |
| 0 061 835 | 2/1989 | European Pat. Off. . |
| 0 145 294 | 10/1989 | European Pat. Off. . |
| 0 267 778 | 3/1993 | European Pat. Off. . |

*Primary Examiner*—Patricia L. Morris
*Attorney, Agent, or Firm*—Joseph C. Gil; Carol Marmo

[57] ABSTRACT

The present invention relates to novel sulphonyl-mercapto-triazolyl derivatives, their acid addition salts and metal salt complexes; a process for the preparation of the novel compounds; and a method for their use as microbicides.

4 Claims, No Drawings

SULPHONYL-MERCAPTO-TRIAZOLYL DERIVATIVES AND THEIR USE AS MICROBICIDES

TECHNICAL FIELD OF THE INVENTION

The present invention relates to novel sulphonyl-mercapto-triazolyl derivatives, to a process for their preparation and to their use as microbicides.

BACKGROUND OF THE INVENTION

It is already known that a large number of triazolyl derivatives have fungicidal properties (cf. EP-A 0 015 756, EP-A 0 040 345, EP-A 0 052 424, EP-A 0 061 835, EP-A 0 297 345, EP-A 0 094 564, EP-A 0 196 038, EP-A 0 267 778, EP-A 0 378 953, EP-A 0 068 813, EP-A 0 044 605, EP-A 0 069 442, EP-A 0 055 833, EP-A 0 301 393, DE-A 2 324 010, DE-A 2 737 489, DE-A 2 551 560, EP-A 0 065 485, DE-A 2 735 872, EP-A 0 234 242, DE-A 2 201 063, EP-A 0 145 294 and DE-A 3 721 786). The activity of these substances is good, but in some cases leaves something to be desired at low application rates.

DETAILED DESCRIPTION OF THE INVENTION

This invention, accordingly, provides novel sulphonyl-mercapto-triazolyl derivatives of the formula

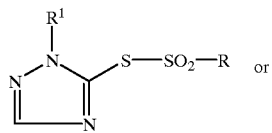

(I-α)

or

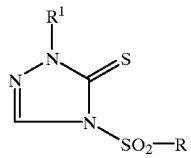

(I-β)

in which
R represents alkyl, optionally substituted aralkyl or represents optionally substituted aryl and
$R^1$ represents a radical of the formula

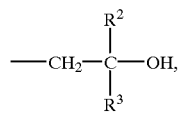

$R^2$ and $R^3$ are identical or different and each represent optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl, or
$R^1$ represents a radical of the formula

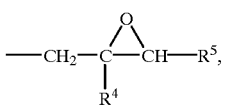

in which
$R^4$ represents alkyl having 1 to 4 carbon atoms, halogenoalkyl having 1 to 4 carbon atoms and 1 to 5 halogen atoms, optionally halogen-substituted cycloalkyl having 3 to 7 carbon atoms, naphthyl or phenyl which is optionally mono- to trisubstituted by identical or different substituents selected from the group consisting of halogen, nitro, phenyl, phenoxy, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms, and $R^5$ represents phenyl which is optionally mono- to trisubstituted by identical or different substituents selected from the group consisting of halogen, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms and halogenoalkylthio having 1 to 4 carbon atoms and 1 to 5 halogen atoms, or
$R^1$ represents a radical of the formula

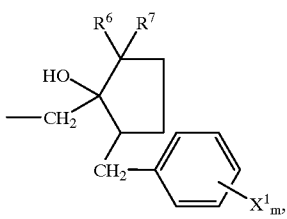

in which
$R^6$ and $R^7$ independently of one another each represent hydrogen or alkyl having 1 to 6 carbon atoms,
$X^1$ represents halogen, alkyl having 1 to 5 carbon atoms, alkoxy having 1 to 4 carbon atoms, phenyl, phenoxy, halogenoalkyl having 1 to 4 carbon atoms and 1 to 5 halogen atoms, halogenoalkoxy having 1 to 4 carbon atoms and 1 to 5 halogen atoms or represents halogenoalkylthio having 1 to 4 carbon atoms and 1 to 5 halogen atoms, and
m represents the numbers 0, 1 or 2,
or $R^1$ represents a radical of the formula

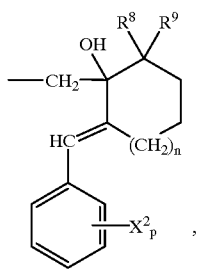

in which
$R^8$ and $R^9$ independently of one another each represent hydrogen or alkyl having 1 to 6 carbon atoms,
$X^2$ represents halogen, cyano, nitro, alkyl having 1 to 4 carbon atoms, alkoxy having 1 to 4 carbon atoms, halogenoalkyl having 1 to 4 carbon atoms and 1 to 5 halogen atoms, halogenoalkoxy having 1 to 4 carbon atoms and 1 to 5 halogen atoms or phenyl,
n represents the numbers 0 or 1 and
p represents the numbers 0, 1 or 2,
or
$R^1$ represents a radical of the formula

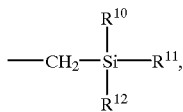

in which
$R^{10}$ represents alkyl having 2 to 18 carbon atoms, cycloalkyl having 3 to 6 carbon atoms, naphthyl or the radical of the formula

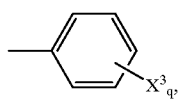

in which
$X^3$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and
q represents the numbers 0, 1 or 2,
$R^{11}$ and $R^{12}$ independently of one another each represent alkyl having 1 to 6 carbon atoms, alkoxy having 1 to 6 carbon atoms, cycloalkyl having 3 to 6 carbon atoms or represent the radical of the formula

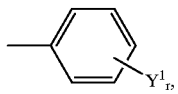

in which
$Y^1$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and
r represents the numbers 0, 1 or 2,
or
$R^1$ represents a radical of the formula

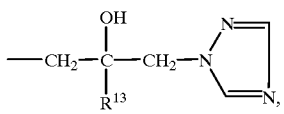

in which
$R^{13}$ represents alkyl having 1 to 6 carbon atoms, halogenoalkyl having 1 to 6 carbon atoms and 1 to 5 halogen atoms, cycloalkyl having 3 to 6 carbon atoms which is optionally substituted by halogen and/or alkyl having 1 to 4 carbon atoms, optionally substituted aryl or represents optionally substituted aralkyl,
or
$R^1$ represents a radical of the formula

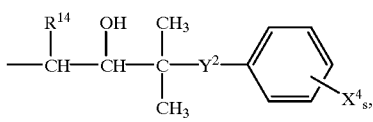

in which
$R^{14}$ represents hydrogen, alkyl or optionally substituted cycloalkyl,
$X^4$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms,
s represents the numbers 0, 1, 2 or 3 and
$Y^2$ represents an oxygen atom, a $CH_2$ group or a direct bond,
or $R^1$ represents a radical of the formula

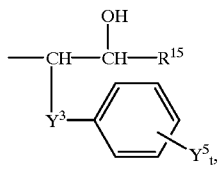

in which
$R^{15}$ represents alkyl having 1 to 6 carbon atoms, halogenoalkyl having 1 to 4 carbon atoms and 1 to 5 halogen atoms, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents optionally halogen-substituted benzyl, $X^5$ represents halogen, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or represents phenoxy which is optionally substituted by halogen and/or alkyl having 1 to 4 carbon atoms, t represents the numbers 0, 1, 2 or 3 and $Y^3$ represents an oxygen atom or represents a $CH_2$ group, or $R^1$ represents a radical of the formula

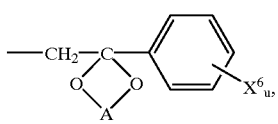

in which
A represents alkanediyl having 2 or 3 carbon atoms which is optionally substituted by halogen and/or alkyl having 1 to 4 carbon atoms, $X^6$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms and
u represents the numbers 0, 1, 2 or 3,
or $R^1$ represents a radical of the formula

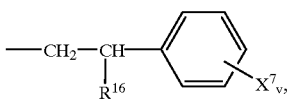

in which
$R^{16}$ represents alkyl having 1 to 10 carbon atoms, halogenoalkyl having 1 to 6 carbon atoms and 1 to 5 halogen atoms, fluoroalkoxyalkyl having 1 to 4 carbon atoms in the fluoroalkoxy moiety and 1 to 4 carbon atoms in the alkyl moiety, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents optionally halogen-substituted phenylalkyl having 1 to 4 carbon atoms in the alkyl moiety, $X^7$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having 1 to 4 carbon atoms, and v represents the numbers 0, 1, 2 or 3,
or $R^1$ represents a radical of the formula

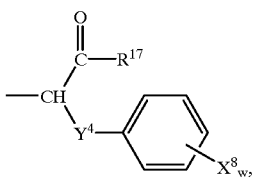

in which
$R^{17}$ represents alkyl having 1 to 6 carbon atoms, halogenoalkyl having 1 to 4 carbon atoms and 1 to 5 halogen atoms, cycloalkyl having 3 to 7 carbon atoms which is optionally substituted by halogen and/or alkyl having 1 to 4 carbon atoms, cycloalkylalkyl having 3 to 7 carbon atoms in the cycloalkyl moiety and 1 to 4 carbon atoms in the alkyl moiety, optionally halogen-substituted phenyl or represents optionally halogen-substituted benzyl, $X^8$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or represents phenoxy which is optionally substituted by halogen and/or alkyl having, 1 to 4 carbon atoms, w represents the numbers 0, 1, 2 or 3 and $Y^4$ represents an oxygen atom or represents a $CH_2$ group, or $R^1$ represents a radical of the formula

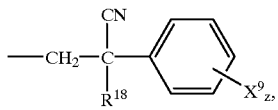

in which $R^{18}$ represents alkyl having 1 to 6 carbon atoms, halogenoalkyl having 1 to 6 carbon atoms and 1 to 5 halogen atoms, optionally substituted aryl or represents optionally substituted aralkyl, $X^9$ represents halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms, or represents phenoxy which is optionally substituted by halogen and/or alkyl having 1 to 4 carbon atoms and z represents the numbers 0, 1, 2 or 3, and acid addition salts and metal salt complexes thereof.

A large number of the substances according to the invention contain one or more asymmetrically substituted carbon atoms. They may therefore be obtained in the form of optical isomers. The present invention relates both to the individual isomers and to mixtures thereof.

Furthermore, it has been found that sulphonyl-mercapto-triazolyl derivatives of the formula (I-α) or (I-β) and acid addition salts and metal salt complexes thereof are obtained when mercapto-triazoles of the formula

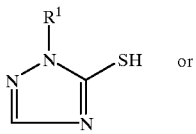 (II-α)

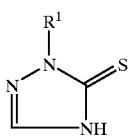 (II-β)

in which $R^1$ is as defined above are reacted with sulphonyl halides of the formula

 R—SO$_2$—Hal    (III)

in which

R is as defined above and

Hal represents chlorine or bromine, if appropriate in the presence of an acid binder and, if appropriate, in the presence of a diluent, and an acid or a metal salt is, if appropriate, subsequently added to the resulting compounds of the formula (I-α) or (I-β).

Finally, it has been found that the novel sulphonyl-mercapto-triazolyl derivatives of the formula (I-α) or (I-β) and acid addition salts and metal salt complexes thereof have very good microbicidal properties and can be used both in crop protection and in the protection of materials for controlling undesirable microorganisms.

Surprisingly, the substances according to the invention have better microbicidal activity, in particular fungicidal activity, than the constitutionally most similar compounds of the prior art of the same direction of action.

The formula (I-α) or (I-β) provides a general definition of the sulphonyl-mercapto-triazolyl derivatives according to the invention.

R preferably represents straight-chain or branched alkyl having 1 to 8 carbon atoms, phenylalkyl having 1 to 4 carbon atoms in the alkyl moiety which is optionally mono- to trisubstituted by identical or different substituents selected from the group consisting of halogen and alkyl having 1 to 4 carbon atoms or represents phenyl which is optionally mono- to trisubstituted by identical or different substituents selected from the group consisting of halogen and alkyl having 1 to 4 carbon atoms.

$R^1$ preferably represents a radical of the formula

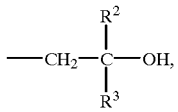

in which $R^2$ preferably represents straight-chain or branched alkyl having 1 to 6 carbon atoms, it being possible for these radicals to be mono- to tetrasubstituted by identical or different substituents selected from the group consisting of halogen, alkoxy having 1 to 4 carbon atoms, alkoximino having 1 to 4 carbon atoms in the alkoxy moiety and cycloalkyl having 3 to 7 carbon atoms, or preferably represents straight-chain or branched alkenyl having 2 to 6 carbon atoms, it being possible for each of these radicals to be mono- to trisubstituted by identical or different substituents selected from the group consisting of halogen, alkoxy having 1 to 4 carbon atoms and cycloalkyl having 3 to 7 carbon atoms, or preferably represents cycloalkyl having 3 to 7 carbon atoms, it being possible for each of these radicals to be mono- to trisubstituted by identical or different substituents selected from the group consisting of halogen, cyano and alkyl having 1 to 4 carbon atoms, or preferably represents aralkyl having 6 to 10 carbon atoms in the aryl moiety and 1 to 4 carbon atoms in the straight-chain or branched alkyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or preferably represents aralkenyl having 6 to 10 carbon atoms in the aryl moiety and 2 to 4 carbon atoms in the alkenyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or preferably represents aroxyalkyl having 6 to 10 carbon atoms in the aryl moiety and 1 to 4 carbon atoms in the straight-chain or branched oxyalkyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or preferably represents aryl having 6 to 10 carbon atoms, it being possible for each of these radicals to mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or preferably represents an optionally benzo-fused five- or six-membered heteroaromatic radical having 1 to 3 hetero atoms, such as nitrogen, sulphur and/or oxygen, it being possible for each of these radicals to be mono- to trisubstituted by identical or different substituents selected from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and cyano, and $R^3$ preferably represents straight-chain or branched alkyl having 1 to 6 carbon atoms, it being possible for these radicals to be mono- to tetrasubstituted by identical or different substituents selected from the group consisting of halogen, alkoxy having 1 to 4 carbon atoms, alkoximino having 1 to 4 carbon atoms in the alkoxy moiety and cycloalkyl having 3 to 7 carbon atoms, or preferably represents straight-chain or branched alkenyl having 2 to 6 carbon atoms, it being possible for each of these radicals to be mono- to trisubstituted by identical or different substituents selected from the group consisting of halogen, alkoxy having 1 to 4 carbon atoms and cycloalkyl having 3 to 7 carbon atoms, or preferably represents cycloalkyl having 3 to 7 carbon atoms, it being possible for each of these radicals to be mono- to trisubstituted by identical or different substituents selected from the group consisting of halogen, cyano and alkyl having 1 to 4 carbon atoms, or preferably represents aralkyl having 6 to 10 carbon atoms in the aryl moiety and 1 to 4 carbon atoms in the straight-chain or branched alkyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or preferably represents aralkenyl having 6 to 10 carbon atoms in the aryl moiety and 2 to 4 carbon atoms in the alkenyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or
preferably represents aroxyalkyl having 6 to 10 carbon atoms in the aryl moiety and 1 to 4 carbon atoms in the straight-chain or branched oxyalkyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or
preferably represents aryl having 6 to 10 carbon atoms, it being possible for each of these radicals to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or
preferably represents an optionally benzo-fused five- or six-membered heteroaromatic radical having 1 to 3 hetero atoms, such as nitrogen, sulphur and/or oxygen, it being possible for each of these radicals to be mono- to trisubstituted by identical or different substituents selected from the group consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and cyano.

$R^1$ furthermore preferably represents a radical of the formula

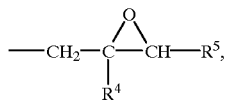

in which
$R^4$ preferably represents methyl, ethyl, n-propyl, isopropyl, n-butyl, sec-butyl, isobutyl, tert-butyl, fluoro-tert-butyl, difluoro-tert-butyl, cycloalkyl having 3 to 6 carbon atoms which is optionally mono- to trisubstituted by identical or different substituents selected from the group consisting of fluorine, chlorine and bromine, represents naphthyl or represents phenyl which may be mono- to trisubstituted by identical or different substituents selected from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and trifluoromethylthio, and $R^5$ preferably represents phenyl which may be mono- to trisubstituted by identical or different substituents selected from the group consisting of fluorine, chlorine, bromine, methyl, ethyl, isopropyl, tert-butyl, methoxy, ethoxy, trifluoromethyl, trichloromethyl, difluoromethyl, difluorochloromethyl, trifluoromethoxy, difluoromethoxy and trifluoromethylthio.

$R^1$ furthermore preferably represents a radical of the formula

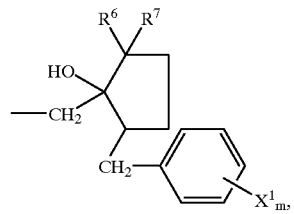

in which
$R^6$ preferably represents hydrogen, methyl, ethyl, n-propyl, isopropyl, n-butyl, isobutyl, sec-butyl, tert-butyl or n-pentyl, $R^7$ preferably represents hydrogen, methyl, ethyl, n-propyl, isopropyl, n-butyl, isobutyl, sec-butyl, tert-butyl or n-pentyl, $X^1$ preferably represents fluorine, chlorine, bromine, methyl, ethyl, n-propyl, isopropyl, n-butyl, isobutyl, sec-butyl, tert-butyl, methoxy, ethoxy, phenyl, phenoxy, trichloromethyl, trifluoromethyl, trifluoromethoxy, difluoromethoxy or trifluoromethylthio and m also preferably represents the numbers 0, 1 or 2, where $X^1$ may represent identical or different radicals if m represents 2.

$R^1$ furthermore preferably represents a radical of the formula

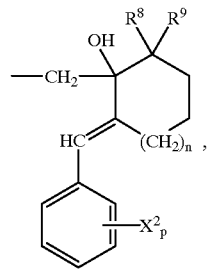

in which
$R^8$ preferably represents hydrogen, methyl, ethyl, n-propyl, isopropyl, n-butyl, isobutyl, sec-butyl, tert-butyl or n-pentyl, $R^9$ preferably represents hydrogen, methyl, ethyl, n-propyl, isopropyl, n-butyl, isobutyl, sec-butyl, tert-butyl or n-pentyl, $X^2$ preferably represents fluorine, chlorine, bromine, cyano, nitro, methyl, ethyl, n-propyl, isopropyl, n-butyl, isobutyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl, n also preferably represents the numbers 0 or 1 and p also preferably represents the numbers 0, 1 or 2,
where $X^2$ may represent identical or different radicals if p represents 2.

$R^1$ furthermore preferably represents a radical of the formula $$-CH_2-\underset{\underset{R^{12}}{|}}{\overset{\overset{R^{10}}{|}}{Si}}-R^{11},$$

in which $R^{10}$ preferably represents alkyl having 2 to 12 carbon atoms, cycloalkyl having 5 or 6 carbon atoms or represents the radical of the formula $$-\!\!\left\langle\!\!\!\begin{array}{c}\\ \\ \end{array}\!\!\!\right\rangle\!\!\!X^3{}_q,$$

in which $X^3$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy and q also preferably represents the numbers 0, 1 or 2, where $X^3$ represents identical or different radicals if q represents 2, $R^{11}$ preferably represents alkyl having 1 to 4 carbon atoms or represents the radical of the formula $$-\!\!\left\langle\!\!\!\begin{array}{c}\\ \\ \end{array}\!\!\!\right\rangle\!\!\!Y^1{}_r,$$

in which $Y^1$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy and r also preferably represents the numbers 0, 1 or 2, where $Y^1$ represents identical or different radicals if r represents 2, and $R^{12}$ preferably represents alkyl having 1 to 4 carbon atoms.

$R^1$ furthermore preferably represents a radical of the formula $$-CH_2-\underset{\underset{R^{13}}{|}}{\overset{\overset{OH}{|}}{C}}-CH_2-N\!\!\left\langle\!\!\!\begin{array}{c}N=\\ \\ =N\end{array}\!\!\!\right.,$$

in which $R^{13}$ preferably represents straight-chain or branched alkyl having 1 to 4 carbon atoms, straight-chain or branched halogenoalkyl having 1 to 4 carbon atoms and 1 to 5 fluorine, chlorine and/or bromine atoms, represents cycloalkyl having 3 to 6 carbon atoms which is optionally mono- to trisubstituted by identical or different substituents selected from the group consisting of fluorine, chlorine, bromine, methyl and ethyl, represents phenyl, benzyl or phenethyl, it being possible for each of the three last-mentioned radicals to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, phenyl which is optionally substituted by halogen and/or alkyl having 1 to 4 carbon atoms or phenoxy which is optionally substituted by halogen and/or alkyl having 1 to 4 carbon atoms.

$R^1$ furthermore preferably represents a radical of the formula $$-\underset{\underset{}{|}}{\overset{\overset{R^{14}}{|}}{CH}}-\underset{\underset{}{|}}{\overset{\overset{OH}{|}}{CH}}-\underset{\underset{CH_3}{|}}{\overset{\overset{CH_3}{|}}{C}}-Y^2-\!\!\left\langle\!\!\!\begin{array}{c}\\ \\ \end{array}\!\!\!\right\rangle\!\!\!X^4{}_s,$$

in which $R^{14}$ preferably represents hydrogen, straight-chain or branched alkyl having 1 to 12 carbon atoms or represents cycloalkyl having 3 to 7 carbon atoms which is optionally mono- to trisubstituted by identical or different substituents selected from the group consisting of halogen and alkyl having 1 to 4 carbon atoms, $X^4$ preferably represents fluorine, chlorine, bromine, methyl, ethyl, methoxy, methylthio, trichloromethyl, trifluoromethyl, trifluoromethoxy, difluoromethoxy, trifluoromethylthio, phenyl or phenoxy, s preferably represents the numbers 0, 1, 2 or 3, where $X^4$ represents identical or different radicals if s represents 2 or 3, and $Y^2$ preferably represents an oxygen atom, a $CH_2$ group or a direct bond.

$R^1$ furthermore preferably represents a radical of the formula $$-\underset{\underset{Y^3-\!\!\left\langle\!\!\!\begin{array}{c}\\ \\ \end{array}\!\!\!\right\rangle\!\!\!X^5{}_t,}{|}}{CH}-\overset{\overset{OH}{|}}{CH}-R^{15}$$

in which $R^{15}$ preferably represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally mono- to trisubstituted by identical or different substituents selected from the group consisting of fluorine, chlorine, bromine, methyl and ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents selected from the group consisting of fluorine, chlorine and bromine or represents benzyl which is optionally mono- to trisubstituted by identical or different substituents selected from the group consisting of fluorine, chlorine and bromine, $X^5$ preferably represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and methyl or represents phenoxy which is optionally mono- or disubstituted by identical or different substituents selected from the group consisting of fluorine, chlorine, bromine and methyl, t preferably represents the numbers 0, 1, 2 or 3, where $X^5$ represents identical or different radicals if t represents 2 or 3 and $Y^3$ preferably represents an oxygen atom or represents a $CH_2$ group.

$R^1$ furthermore preferably represents a radical of the formula

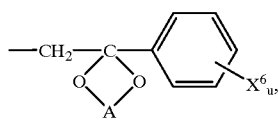

in which

A preferably represents alkanediyl having 2 or 3 carbon atoms which is optionally mono- to trisubstituted by identical or different substituents selected from the group consisting of fluorine, chlorine, bromine, methyl, ethyl, n-propyl, isopropyl, n-butyl, i-butyl, sec-butyl and tert-butyl, $X^6$ preferably represents fluorine, chlorine, bromine, methyl, ethyl, methoxy, methylthio, trichloromethyl, trifluoromethyl, trifluoromethoxy, trifluoromethylthio, difluoromethoxy, phenyl which is optionally mono- to trisubstituted by identical or different substituents selected from the group consisting of fluorine, chlorine and methyl and/or represents phenoxy which is optionally mono- to trisubstituted by identical or different substituents selected from the group consisting of fluorine, chlorine and methyl and u preferably represents the numbers 0, 1, 2 or 3, where $X^6$ represents identical or different radicals if u represents 2 or 3.

$R^1$ furthermore preferably represents a radical of the formula

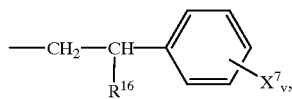

in which $R^{16}$ preferably represents straight-chain or branched alkyl having 1 to 6 carbon atoms, straight-chain or branched halogenoalkyl having 1 to 6 carbon atoms and 1 to 5 fluorine, chlorine and/or bromine atoms, fluoroalkoxyalkyl having 1 to 3 carbon atoms and 1 to 5 fluorine atoms in the fluoroalkoxy moiety and 1 to 3 carbon atoms in the alkyl moiety, cycloalkyl having 3 to 6 carbon atoms which is optionally mono- to trisubstituted by identical or different substituents selected from the group consisting of fluorine, chlorine, bromine, methyl and ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents selected from the group consisting of fluorine, chlorine and bromine or represents phenylalkyl having 1 or 2 carbon atoms in the alkyl moiety which is optionally mono- to trisubstituted by identical or different substituents selected from the group consisting of fluorine, chlorine and bromine, $X^7$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and methyl or represents phenoxy which is optionally mono- or disubstituted by identical or different substituents selected from the group consisting of fluorine, chlorine, bromine and methyl and v preferably represents the numbers 0, 1, 2 or 3, where $X^7$ represents identical or different radicals if v represents 2 or 3.

$R^1$ furthermore preferably represents a radical of the formula

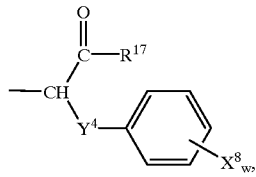

in which $R^{17}$ preferably represents straight-chain or branched alkyl having 1 to 4 carbon atoms, fluoroalkyl having 1 to 4 carbon atoms and 1 to 5 fluorine atoms, cycloalkyl having 3 to 6 carbon atoms which is optionally mono- to trisubstituted by identical or different substituents selected from the group consisting of fluorine, chlorine, bromine, methyl and ethyl, cycloalkylalkyl having 3 to 6 carbon atoms in the cycloalkyl moiety and 1 to 3 carbon atoms in the alkyl moiety, phenyl which is optionally mono- to trisubstituted by identical or different substituents selected from the group consisting of fluorine, chlorine and bromine or represents benzyl which is optionally mono- to trisubstituted by identical or different substituents selected from the group consisting of fluorine, chlorine and bromine, $X^8$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and methyl or represents phenoxy which is optionally mono- or disubstituted by identical or different substituents selected from the group consisting of fluorine, chlorine, bromine and methyl, w preferably represents the numbers 0, 1, 2 or 3, where $X^8$ represents identical or different radicals if w represents 2 or 3, and $Y^4$ preferably represents an oxygen atom or represents a $CH_2$ group.

$R^1$ moreover also preferably represents a radical of the formula

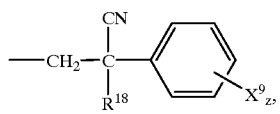

in which

R[18] preferably represents straight-chain or branched alkyl having 1 to 4 carbon atoms, halogenoalkyl having 1 to 4 carbon atoms and 1 to 5 halogen atoms, phenyl which is optionally mono- to trisubstituted by identical or different substituents selected from the group consisting of halogen, alkyl having 1 to 4 carbon atoms, halogenoalkyl having 1 or 2 carbon atoms with 1 to 5 halogen atoms, alkoxy having 1 to 4 carbon atoms and halogenoalkoxy having 1 or 2 carbon atoms and 1 to 5 halogen atoms or represents phenylalkyl having 1 to 4 carbon atoms in the alkyl moiety which is optionally mono- to trisubstituted by identical or different substituents selected from the group consisting of halogen, alkyl having 1 to 4 carbon atoms, halogenoalkyl having 1 or 2 carbon atoms and 1 to 5 halogen atoms, alkoxy having 1 to 4 carbon atoms and halogenoalkoxy having 1 or 2 carbon atoms and 1 to 5 halogen atoms, $X^9$ preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl which is optionally mono- or disubstituted by identical or different substituents selected from the group consisting of fluorine, chlorine, bromine and methyl or represents phenoxy which is optionally mono- or disubstituted by identical or different substituents selected from the group consisting of fluorine, chlorine, bromine and methyl and z preferably represents the numbers 0, 1, 2 or 3, where $X^9$ represents identical or different radicals if z represents 2 or 3.

R particularly preferably represents straight-chain or branched alkyl having 1 to 6 carbon atoms, phenyl which is optionally mono- to trisubstituted by identical or different substituents selected from the group consisting of fluorine, chlorine, bromine, methyl, ethyl, n-propyl, isopropyl, n-butyl and tert-butyl or represents phenylalkyl having 1 or 2 carbon atoms in the alkyl moiety which is optionally mono- to trisubstituted by identical or different substituents selected from the group consisting of fluorine, chlorine, bromine, methyl, ethyl, n-propyl, isopropyl, n-butyl and tert-butyl.

$R^1$ particularly preferably represents a radical of the formula

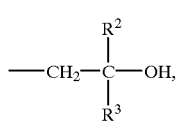

in which $R^2$ particularly preferably represents straight-chain or branched alkyl having 1 to 4 carbon atoms, it being possible for these radicals to be mono- to tetrasubstituted by identical or different substituents selected from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl, or particularly preferably represents straight-chain or branched alkenyl having 2 to 5 carbon atoms, it being possible for each of these radicals to be mono- to trisubstituted by identical or different substituents selected from the group consisting of fluorine, chlorine, bromine, methoxy, ethoxy, propoxy, isopropoxy, cyclopropyl, cyclobutyl, cyclopentyl and cyclohexyl, or particularly preferably represents cycloalkyl having 3 to 6 carbon atoms, it being possible for each of these radicals to mono- to trisubstituted by identical or different substituents selected from the group consisting of fluorine, chlorine, bromine, cyano, methyl, ethyl, propyl, isopropyl and tert-butyl, or particularly preferably represents phenylalkyl having 1 to 4 carbon atoms in the straight-chain or branched alkyl moiety, it being possible for the phenyl moiety to be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or particularly preferably represents phenylalkenyl having 2 to 4 carbon atoms in the alkenyl moiety, it being possible for the phenyl moiety to be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or particularly preferably represents phenoxyalkyl having 1 to 4 carbon atoms in the straight-chain or branched oxyalkyl moiety, it being possible for the phenyl moiety to be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or particularly preferably represents phenyl which may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or particularly preferably represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and propionyl, and $R^3$ particularly preferably represents straight-chain or branched alkyl having 1 to 4 carbon atoms, it being possible for these radicals to be mono- to tetrasubstituted by identical or different substituents selected from the group consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and cyclohexyl, or particularly preferably represents straight-chain or branched alkenyl having 2 to 5 carbon atoms, it being possible for each of these radicals to be mono- to trisubstituted by identical or different substituents selected from the group consisting of fluorine, chlorine, bromine, methoxy, ethoxy, propoxy, isopropoxy, cyclopropyl, cyclobutyl, cyclopentyl and cyclohexyl, or particularly preferably represents cycloalkyl having 3 to 6 carbon atoms, it being possible for each of these radicals to be mono- to trisubstituted by identical or different substituents selected from the group consisting of fluorine, chlorine, bromine, cyano, methyl, ethyl, propyl, isopropyl and tert-butyl, or particularly preferably represents phenylalkyl having 1 to 4 carbon atoms in the straight-chain or branched alkyl moiety, it being possible for the phenyl moiety to be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or particularly preferably represents phenylalkenyl having 2 to 4 carbon atoms in the alkenyl moiety, it being possible for the phenyl moiety to be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or particularly preferably represents phenoxyalkyl having 1 to 4 carbon atoms in the straight-chain or branched oxyalkyl moiety, it being possible for the phenyl moiety to be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifuoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or particularly preferably represents phenyl which may be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano, or particularly preferably represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be mono- to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and propionyl.

$R^1$ furthermore particularly preferably represents a radical of the formula

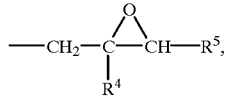

in which $R^4$ particularly preferably represents methyl, ethyl, n-propyl, isopropyl, n-butyl, sec-butyl, isobutyl, tert-butyl, fluoro-tert-butyl, difluoro-tert-butyl, cycloalkyl having 3 to 6 carbon atoms which is optionally mono- to trisubstituted by identical or different substituents selected from the group consisting of fluorine, chlorine and bromine, represents naphthyl or represents phenyl which may be mono- to trisubstituted by identical or different substituents selected from the group consisting of fluorine, chlorine, bromine, nitro, phenyl, phenoxy, methyl, ethyl, tert-butyl, methoxy, ethoxy, trifluoromethyl, trichloromethyl, difluoromethyl, difluorochloromethyl, trifluoromethoxy, difluoromethoxy and trifluoromethylthio, and $R^5$ particularly preferably represents phenyl which may be mono- to trisubstituted by identical or different substituents selected from the group consisting of fluorine, chlorine, bromine, methyl, ethyl, isopropyl, tert-butyl, methoxy, ethoxy, trifluoromethyl, trichloromethyl, difluoromethyl, difluorochloromethyl, trifluoromethoxy, difluoromethoxy and trifluoromethylthio.

$R^1$ furthermore particularly preferably represents a radical of the formula

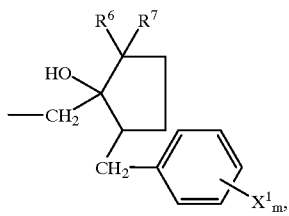

in which
$R^6$ particularly preferably represents hydrogen, methyl, ethyl, n-propyl, isopropyl, n-butyl, isobutyl, sec-butyl, tert-butyl or n-pentyl, $R^7$ particularly preferably represents hydrogen, methyl, ethyl, n-propyl, isopropyl, n-butyl, isobutyl, sec-butyl, tert-butyl or n-pentyl, $X^1$ particularly preferably represents fluorine, chlorine, bromine, methyl, ethyl, n-propyl, isopropyl, n-butyl, isobutyl, sec-butyl, tert-butyl, methoxy, ethoxy, phenyl, phenoxy, trichloromethyl, trifluoromethyl, trifluoromethoxy, difluoromethoxy or trifluoromethylthio and m also particularly preferably represents the numbers 0, 1 or 2, it being possible for $X^1$ to represent identical or different radicals if m represents 2.

$R^1$ furthermore particularly preferably represents a radical of the formula

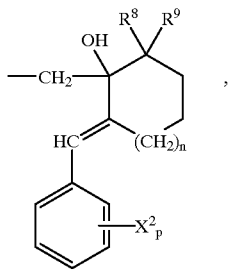

in which
$R^8$ particularly preferably represents hydrogen, methyl, ethyl, n-propyl, isopropyl, n-butyl, isobutyl, sec-butyl, tert-butyl or n-pentyl, $R^9$ particularly preferably represents hydrogen, methyl, ethyl, n-propyl, isopropyl, n-butyl, isobutyl, sec-butyl, tert-butyl or n-pentyl, $X^2$ particularly preferably represents fluorine, chlorine, bromine, cyano, nitro, methyl, ethyl, n-propyl, isopropyl, n-butyl, isobutyl, sec-butyl, tert-butyl, methoxy, ethoxy, trifluoromethyl, trichloromethyl, difluoromethyl, trichloromethoxy, trifluoromethoxy, difluoromethoxy, difluorochloromethoxy or phenyl, n also particularly preferably represents the numbers 0 or 1 and p also particularly preferably represents the numbers 0, 1 or 2, it being possible for $X^2$ to represent identical or different radicals if p represents 2.

$R^1$ furthermore particularly preferably represents a radical of the formula

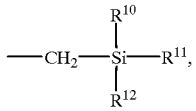

in which
$R^{10}$ particularly preferably represents the radical of the formula

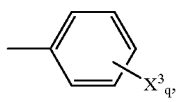

in which
$X^3$ particularly preferably represents fluorine, chlorine, bromine, methyl, methoxy, methylthio, trichloromethyl, trifluoromethyl, trifluoromethoxy, difluoromethoxy or phenyl and q also particularly preferably represents the numbers 0, 1 or 2, it being possible for $X^3$ to represent identical or different radicals if Q represents 2, $R^{11}$ particularly preferably represents methyl, ethyl, n-propyl, n-butyl or represents the radical of the formula

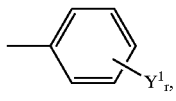

in which
$Y^1$ particularly preferably represents fluorine, chlorine, bromine, methyl, ethyl, methoxy, trichloromethyl, trifluoromethyl, trifluoromethoxy, difluoromethoxy or phenyl, and r also particularly preferably represents the numbers 0, 1 or 2, it being possible for $Y^1$ to represent identical or different radicals if r represents 2, and $R^{12}$ particularly preferably represents methyl, ethyl, n-propyl or n-butyl.

$R^1$ furthermore particularly preferably represents a radical of the formula

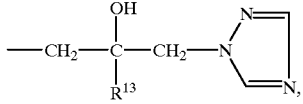

in which
$R^{13}$ particularly preferably represents methyl, ethyl, n-propyl, isopropyl, n-butyl, sec-butyl, isobutyl, tert-butyl, halogenoalkyl having 1 to 4 carbon atoms and 1 to 3 fluorine, chlorine and/or bromine atoms, cyclopropyl, cyclopentyl or cyclohexyl, each of which is optionally mono- to trisubstituted by identical or different substituents selected from the group consisting of fluorine, chlorine, bromine, methyl and ethyl, and also represents phenyl, benzyl or phenethyl, it being possible for each of the three last-mentioned radicals to be mono- to trisubstituted in the phenyl moiety by identical or different substituents selected from the group consisting of fluorine, chlorine, bromine, methyl, ethyl, methoxy, methylthio, trichloromethyl, trifluoromethyl, trifluoromethoxy, difluoromethoxy, trifluoromethylthio, phenyl and phenoxy.

$R^1$ furthermore particularly preferably represents a radical of the formula

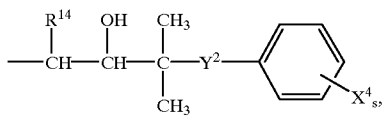

in which $R^{14}$ particularly preferably represents hydrogen, straight-chain or branched alkyl having 1 to 6 carbon atoms or represents cyclopropyl, cyclopentyl or cyclohexyl, each of which is optionally mono- to trisubstituted by identical or different substituents selected from the group consisting of fluorine, chlorine, bromine, methyl and ethyl, $X^4$ particularly preferably represents fluorine, chlorine, bromine, methyl, methoxy, methylthio, trichloromethyl, trifluoromethyl, trifluoromethoxy, difluoromethoxy, trifluoromethylthio, phenyl or phenoxy, s also particularly preferably represents the numbers 0, 1, 2 or 3, it being possible for $X^4$ to represent identical or different radicals if s represents 2 or 3 and $Y^2$ also particularly preferably represents an oxygen atom, a $CH_2$ group or a direct bond.

$R^1$ furthermore particularly preferably represents a radical of the formula

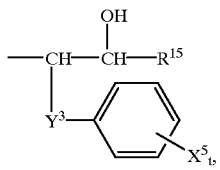

in which $R^{15}$ particularly preferably represents methyl, isopropyl, tert-butyl, fluoro-tert-butyl, difluoro-tert-butyl, represents cyclopropyl, cyclopentyl or cyclohexyl, each of which is optionally mono- to trisubstituted by identical or different substituents selected from the group consisting of fluorine, chlorine and methyl, represents cycloalkylalkyl having 3 to 6 carbon atoms in the cycloalkyl moiety and 1 or 2 carbon atoms in the alkyl moiety, represents phenyl which is optionally mono- or disubstituted by identical or different substituents selected from the group consisting of fluorine, chlorine and bromine or represents benzyl which is optionally mono- or disubstituted by identical or different substituents selected from the group consisting of fluorine, chlorine and bromine, $X^5$ particularly preferably represents fluorine, chlorine, bromine, nitro, methyl, ethyl, tert-butyl, methoxy, methylthio, trichloromethyl, trifluoromethyl, trifluoromethoxy, difluoromethoxy, trifluoromethylthio, phenyl or phenoxy, t also particularly preferably represents the numbers 0, 1, 2 or 3, it being possible for $X^5$ to represent identical or different radicals if t represents 2 or 3 and $Y^3$ also particularly preferably represents an oxygen atom or represents a $CH_2$ group.

$R^1$ furthermore particularly preferably represents a radical of the formula

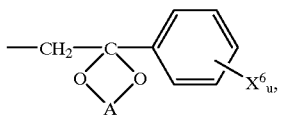

in which

A particularly preferably represents alkanediyl having 2 or 3 carbon atoms which is optionally mono- to trisubstituted by identical or different substituents selected from the group consisting of fluorine, chlorine, bromine, methyl, ethyl, n-propyl, isopropyl, n-butyl, i-butyl, sec-butyl and tert-butyl, $X^6$ particularly preferably represents fluorine, chlorine, bromine, methyl, ethyl, methoxy, methylthio, trichloromethyl, trifluoromethyl, trifluoromethoxy, trifluoromethylthio, difluoromethoxy, phenyl which is optionally mono- to trisubstituted by identical or different substituents selected from the group consisting of fluorine, chlorine and methyl and/or represents phenoxy which is optionally mono- to trisubstituted by identical or different substituents selected from the group consisting of fluorine, chlorine and methyl and u also particularly preferably represents the numbers 0, 1, 2 or 3, it being possible for $X^6$ to represent identical or different radicals if u represents 2 or 3.

$R^1$ furthermore particularly preferably represents a radical of the formula

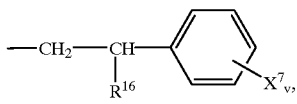

in which $R^{16}$ particularly preferably represents methyl, ethyl, n-propyl, isopropyl, n-butyl, isobutyl, sec-butyl, tert-butyl, halogenoalkyl having 1 to 4 carbon atoms and 1 to 5 fluorine, chlorine and/or bromine atoms, fluoroalkoxyalkyl having 1 or 2 carbon atoms and 1 to 5 fluorine atoms in the fluoroalkoxy moiety and 1 or 2 carbon atoms in the alkyl moiety, cyclopropyl, cyclopentyl or cyclohexyl, each of which is optionally mono- to trisubstituted by identical or different substituents selected from the group consisting of fluorine, chlorine and methyl, represents cycloalkylalkyl having 3 to 6 carbon atoms in the cycloalkyl moiety and 1 or 2 carbon atoms in the alkyl moiety, phenyl which is optionally mono- or disubstituted by identical or different substituents selected from the group consisting of fluorine, chlorine and bromine or represents benzyl which is optionally mono- or disubstituted by identical or different substituents selected from the group consisting of fluorine, chlorine and bromine, $X^7$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy and v also particularly preferably represents the numbers 0, 1, 2 or 3, it being possible for $X^7$ to represent identical or different radicals if v represents 2 or 3.

$R^1$ furthermore particularly preferably represents a radical of the formula

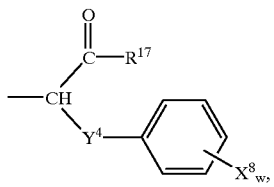

in which $R^{17}$ particularly preferably represents methyl, isopropyl, tert-butyl, fluoro-tert-butyl, difluoro-tert-butyl, cyclopropyl, cyclopentyl or cyclohexyl, each of which is optionally mono- to trisubstituted by identical or different substituents selected from the group consisting of fluorine, chlorine and methyl, represents cycloalkylalkyl having 3 to 6 carbon atoms in the cycloalkyl moiety and 1 or 2 carbon atoms in the alkyl moiety, phenyl which is optionally mono- or disubstituted by identical or different substituents selected from the group consisting of fluorine, chlorine and bromine or represents benzyl which is optionally mono- or disubstituted by identical or different substituents selected from the group consisting of fluorine, chlorine and bromine, $X^8$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy, $Y^4$ also particularly preferably represents an oxygen atom or represents a $CH_2$ group, and w also particularly preferably represents the numbers 0, 1, 2 or 3, where $X^8$ represents identical or different radicals if w represents 2 or 3.

$R^1$ moreover also preferably represents a radical of the formula

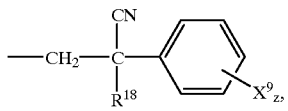

in which $R^{18}$ particularly preferably represents methyl, ethyl, n-propyl, isopropyl, n-butyl, sec-butyl, isobutyl, tert-butyl, fluoro-tert-butyl, difluoro-tert-butyl, phenyl which is optionally mono- or disubstituted by identical or different substituents selected from the group consisting of fluorine, chlorine, methyl, ethyl, trifluoromethyl, trichloromethyl, methoxy, ethoxy, trifluoromethoxy and difluoromethoxy or represents phenylalkyl having 1 or 2 carbon atoms in the alkyl moiety which is optionally mono- or disubstituted in the phenyl moiety by identical or different substituents selected from the group consisting of fluorine, chlorine, bromine, methyl, ethyl, trifluomethyl, trichloromethyl, methoxy, ethoxy, trifluoromethoxy and difluoromethoxy, $X^9$ particularly preferably represents fluorine, chlorine, bromine, methyl, ethyl, tert-butyl, methoxy, methylthio, trichloromethyl, trifluoromethyl, trifluoromethoxy, difluoromethoxy, trifluoromethylthio, phenyl or phenoxy, and z also particularly preferably represents the numbers 0, 1, 2 or 3, it being possible for $X^9$ to represent identical or different radicals if z represents 2 or 3.

Preferred compounds according to the invention are also addition products of acids and those sulphonyl-mercapto-triazolyl derivatives of the formula (I-α) or (I-β) in which R and $R^1$ have those meanings which have been mentioned as being particularly preferred for these substituents.

The acids which can be added preferably include hydrohalic acids, such as, for example, hydrochloric acid and hydrobromic acid, in particular hydrochloric acid, furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid and 1,5-naphthalenedisulphonic acid, and also saccharin and thiosaccharin.

Preferred compounds according to the invention are moreover addition products of salts of metals of main groups II to IV and sub-groups I and II and also IV to VIII of the Periodic Table of the Elements and those sulphonyl-mercapto-triazolyl derivatives of the formula (I-α) or (I-β) in which R and $R^1$ have those meanings which have been mentioned as being preferred for these substituents.

Particular preference is given here to salts of copper, zinc, manganese, magnesium, tin, iron and nickel. Suitable anions of these salts are those which are derived from those acids which lead to physiologically acceptable addition products. Acids of this kind which are particularly preferred in this context are hydrohalic acids, such as, for example, hydrochloric acid and hydrobromic acid, furthermore phosphoric acid, nitric acid and sulphuric acid.

The mercapto-triazoles required as starting materials in the preparation of the substances according to the invention may be present in the "mercapto" form of the formula

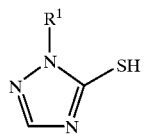
(II-α)

or in the tautomeric "thiono" form of the formula

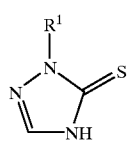
(II-β)

The substances according to the invention are therefore derived from the "mercapto" form or from the "thiono"

form. This means that the substances according to the invention are present either as substances of the formula

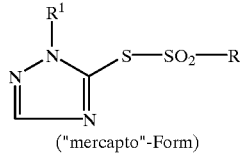
("mercapto"-Form) (I-α)

or the formula

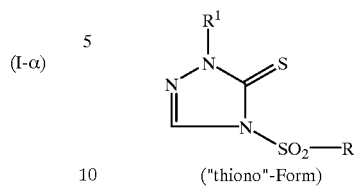
("thiono"-Form) (I-β)

or as mixtures of substances of the formulae (I-α) and (I-β).

Examples of substances according to the invention include the sulphonyl-mercapto-triazolyl derivatives listed in the tables below.

TABLE 1

| $R^2$ | $R^3$ | R |
|---|---|---|
| Cl—C₆H₄—CH₂—CH₂— | —C(CH₃)₃ | —CH₃ |
| Cl—C₆H₄—CH₂—CH₂— | —C(CH₃)₃ | —C₂H₅ |
| Cl—C₆H₄—CH₂—CH₂— | —C(CH₃)₃ | —C₆H₄—CH₃ |
| Cl—C₆H₄—CH₂—CH₂— | —C(CH₃)₃ | —CH₂—C₆H₅ |
| Cl—C₆H₄—CH₂— | —C(CH₃)₃ | —CH₃ |
| Cl—C₆H₄—CH₂— | —C(CH₃)₃ | —C₂H₅ |
| Cl—C₆H₄—CH₂— | —C(CH₃)₃ | —C₆H₄—CH₃ |

TABLE 1-continued
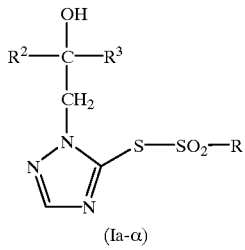
| R² | R³ | R |
|---|---|---|
| 4-Cl-C₆H₄-CH₂- | -C(CH₃)₃ | -CH₂-C₆H₅ |
| 4-Cl-C₆H₄-CH(CH₃)- | -C(CH₃)₃ | -CH₃ |
| 4-Cl-C₆H₄-CH(CH₃)- | -C(CH₃)₃ | -C₂H₅ |
| 4-Cl-C₆H₄-CH(CH₃)- | -C(CH₃)₃ | -CH₂-C₆H₅ |
| 4-F-C₆H₄- | 2-F-C₆H₄- | -C₂H₅ |
| 4-F-C₆H₄- | 2-F-C₆H₄- | -CH₂-C₆H₅ |
| 4-F-C₆H₄- | 2-F-C₆H₄- | 4-CH₃-C₆H₄- |
| 2,4-Cl₂-C₆H₃- | -C₄H₉-n | -CH₃ |
| 2,4-Cl₂-C₆H₃- | -C₄H₉-n | -C₂H₅ |

TABLE 1-continued

| | OH |   |
|---|---|---|
| | R²—C—R³ | |
| | \| | |
| | CH₂ | |
| (structure Ia-α: triazole with -S-SO₂-R) | and | (structure Ia-β: triazole-thione with -SO₂-R) |
| (Ia-α) | | (Ia-β) |

| R² | R³ | R |
|---|---|---|
| 2,4-dichlorophenyl | —C₄H₉-n | —CH₂-phenyl |
| 2,4-dichlorophenyl | —C₄H₉-n | —C₆H₄-CH₃ (p-tolyl) |
| 4-chlorophenyl | —CH(CH₃)-cyclopropyl | —CH₃ |
| 4-chlorophenyl | —CH(CH₃)-cyclopropyl | —C₆H₄-CH₃ (p-tolyl) |
| 4-chlorophenyl | —CH(CH₃)-cyclopropyl | —CH₂-phenyl |
| 4-chlorophenoxymethyl | —C(CH₃)₃ | —CH₃ |
| 4-chlorophenoxymethyl | —C(CH₃)₃ | —C₂H₅ |
| 4-chloropyridyloxymethyl | —C(CH₃)₃ | —CH₂-phenyl |
| 4-chlorophenoxymethyl | —C(CH₃)₃ | —C₆H₄-CH₃ (p-tolyl) |
| Cl₂CH—CCl₂—CH₂— | —C(CH₃)₃ | —CH₃ |
| Cl₂CH—CCl₂—CH₂— | —C(CH₃)₃ | —C₂H₅ |
| Cl₂CH—CCl₂—CH₂— | 1-chlorocyclopropyl | —CH₃ |

TABLE 1-continued

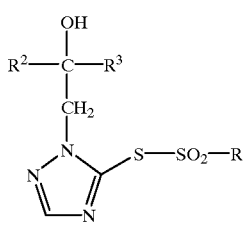

| R² | R³ | R |
|---|---|---|
| Cl₂CH—CCl₂—CH₂— | cyclopropyl-Cl | —C₂H₅ |
| Cl₂CH—CCl₂—CH₂— | cyclopropyl-F | —CH₃ |
| Cl₂CH—CCl₂—CH₂— | cyclopropyl-F | -C₆H₄-CH₃ (p-tolyl) |
| 4-Cl-C₆H₄-CH=CH— | —C(CH₃)₃ | —CH₃ |
| 4-Cl-C₆H₄-CH=CH— | —C(CH₃)₃ | —C₂H₅ |
| 4-Cl-C₆H₄-CH=CH— | cyclopropyl-Cl | —CH₃ |
| 4-Cl-C₆H₄-CH₂-CH₂— | cyclopropyl-Cl | —C₂H₅ |
| 4-Cl-C₆H₄-CH₂— | cyclopropyl-Cl | —C₂H₅ |
| 4-Cl-C₆H₄-CH(CH₃)— | cyclopropyl-Cl | —C₂H₅ |
| 4-Cl-C₆H₄-O-CH₂— | cyclopropyl-Cl | —CH₃ |
| Cl₂CH—CCl₂— | cyclopropyl-Cl | —CH₃ |
| 2-furyl-CH₂-CH₂— | —C(CH₃)₃ | —CH₃ |

TABLE 1-continued
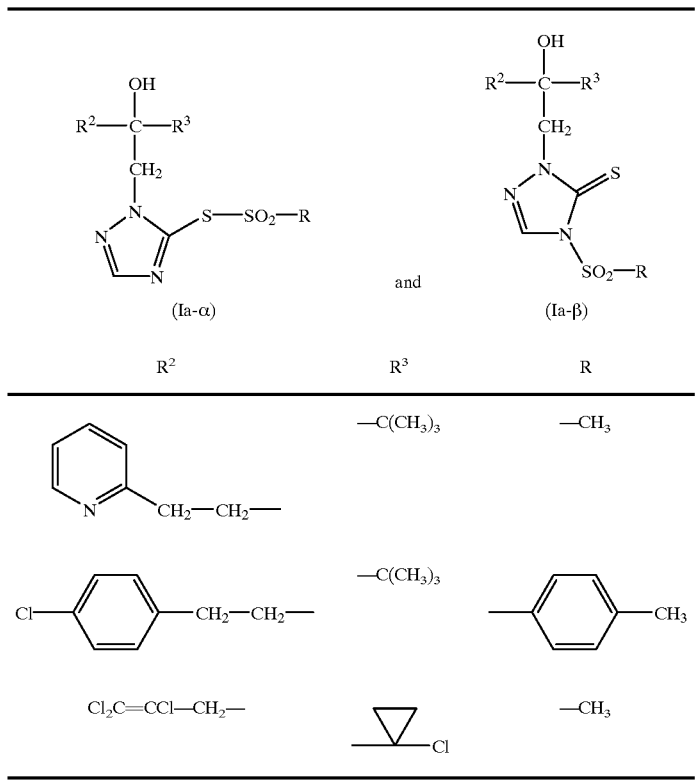
TABLE 2
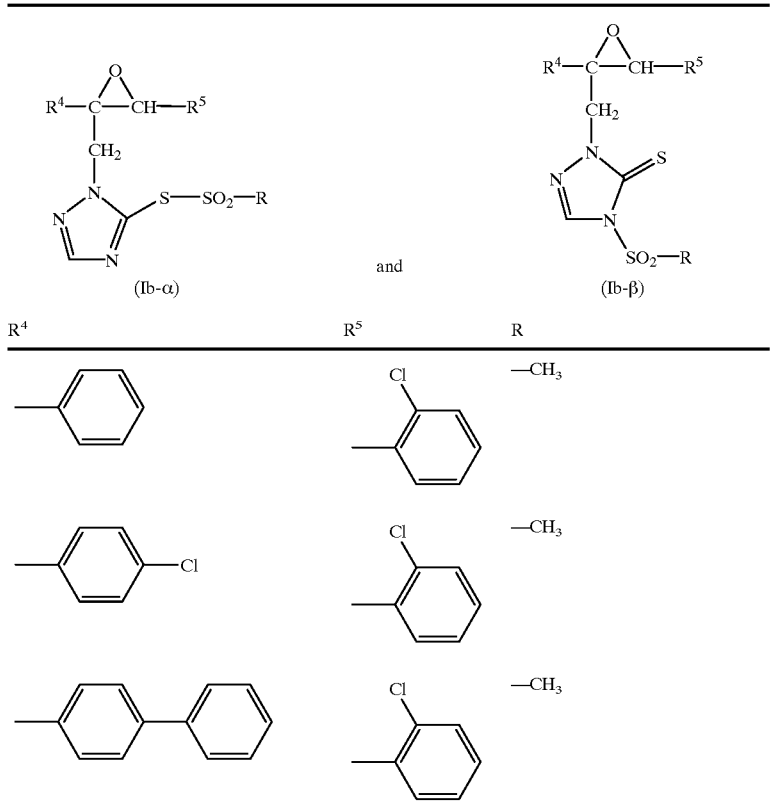

TABLE 2-continued
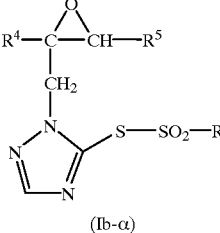
| R⁴ | R⁵ | R |
|---|---|---|
| 2,4-dichlorophenyl | 2-chlorophenyl | —CH₃ |
| 2-chlorophenyl | 2-chlorophenyl | —CH₃ |
| 2-fluorophenyl | 2-chlorophenyl | —CH₃ |
| 4-methylphenyl | 2-chlorophenyl | —CH₃ |
| —C(CH₃)₂CH₂F | 2-chlorophenyl | —CH₃ |
| 2-bromo-4-fluorophenyl | 2-chlorophenyl | —CH₃ |
| 4-bromophenyl | 2-chlorophenyl | —CH₃ |
| 3,4-dichlorophenyl | 2-chlorophenyl | —CH₃ |

TABLE 2-continued
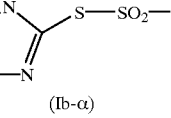
(Ib-α)
and
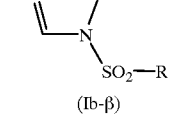
(Ib-β)
| R⁴ | R⁵ | R |
|---|---|---|
| 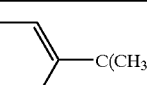 | 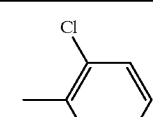 | —CH₃ |
| 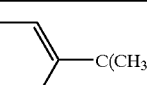 | 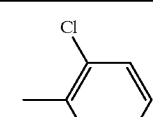 | —CH₃ |
| 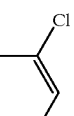 | 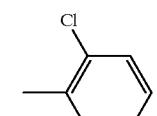 | —CH₃ |
| 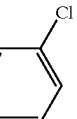 | 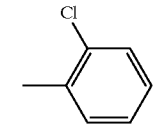 | —CH₃ |
| 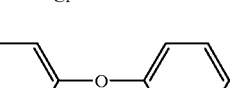 | 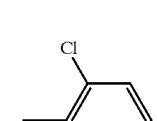 | —CH₃ |
| 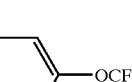 | 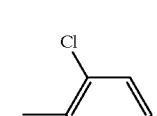 | —CH₃ |
| 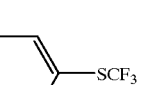 | 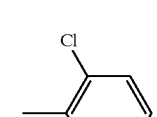 | —CH₃ |
|  | 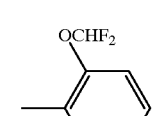 | —CH₃ |

TABLE 2-continued
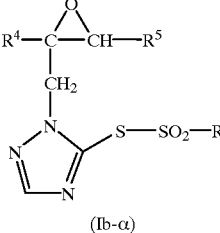
(Ib-α)   and   (Ib-β)
| R⁴ | R⁵ | R |
|---|---|---|
| 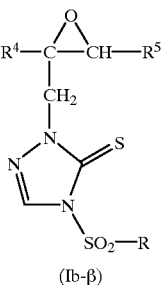 | 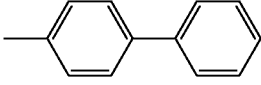 | —CH₃ |
| 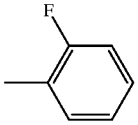 | 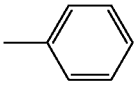 | —CH₃ |
| 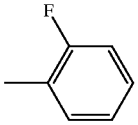 | 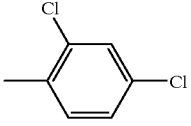 | —CH₃ |
| 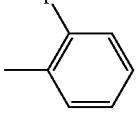 | 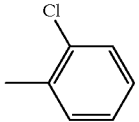 | —CH₃ |
| 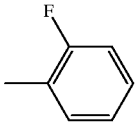 | 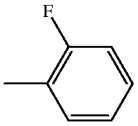 | —CH₃ |
| 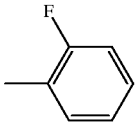 | 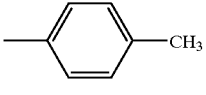 | —CH₃ |
| 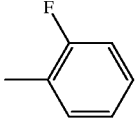 | 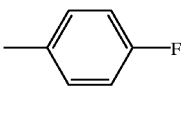 | —CH₃ |
| 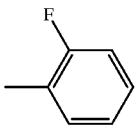 | 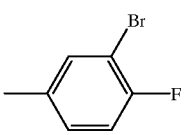 | —CH₃ |

TABLE 2-continued
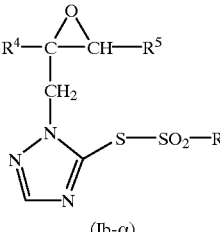
| R⁴ | R⁵ | R |
|---|---|---|
| 4-Br-C₆H₄— | 2-F-C₆H₄— | —CH₃ |
| 3,4-Cl₂-C₆H₃— | 2-F-C₆H₄— | —CH₃ |
| 4-C(CH₃)₃-C₆H₄— | 2-F-C₆H₄— | —CH₃ |
| 3-Cl-C₆H₄— | 2-F-C₆H₄— | —CH₃ |
| 3,5-Cl₂-C₆H₃— | 2-F-C₆H₄— | —CH₃ |
| 4-PhO-C₆H₄— | 2-F-C₆H₄— | —CH₃ |
| 4-Cl-C₆H₄— | 2-Br-C₆H₄— | —CH₃ |
| C₆H₅— | 2-Br-C₆H₄— | —CH₃ |

TABLE 2-continued
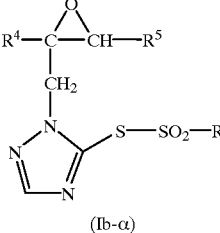
| R⁴ | R⁵ | R |
|---|---|---|
| 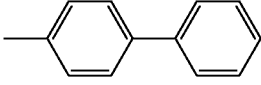 | 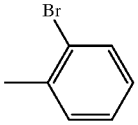 | —CH₃ |
| 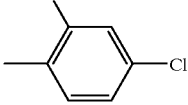 | 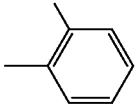 | —CH₃ |
| 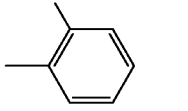 | 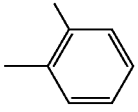 | —CH₃ |
| 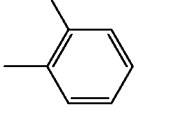 | 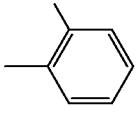 | —CH₃ |
| 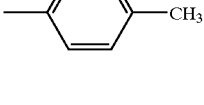 | 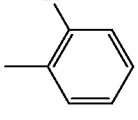 | —CH₃ |
| 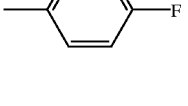 | 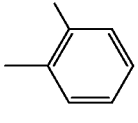 | —CH₃ |
| 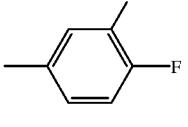 | 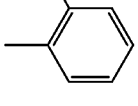 | —CH₃ |
| 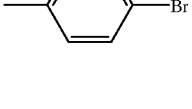 | 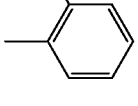 | —CH₃ |

TABLE 2-continued

|  | | |
|---|---|---|
| R⁴—C(—O—CH—R⁵)—CH₂—N(triazole)—S—SO₂—R (Ib-α) | and | R⁴—C(—O—CH—R⁵)—CH₂—N(triazole-thione)—SO₂—R (Ib-β) |

| R⁴ | R⁵ | R |
|---|---|---|
| 3,4-dichlorophenyl | 2-bromophenyl | —CH₃ |
| 4-tert-butylphenyl | 2-bromophenyl | —CH₃ |
| 3-chlorophenyl | 2-bromophenyl | —CH₃ |
| 3,5-dichlorophenyl | 2-bromophenyl | —CH₃ |
| 4-phenoxyphenyl | 2-bromophenyl | —CH₃ |
| —CH₃ | 2-chlorophenyl | —CH₃ |
| —CH₃ | 2-fluorophenyl | —CH₃ |
| —CH₃ | 2-bromophenyl | —CH₃ |

TABLE 2-continued
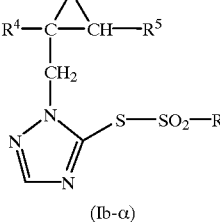
(Ib-α) and (Ib-β)
| R⁴ | R⁵ | R |
|---|---|---|
| —C(CH₃)₃ | 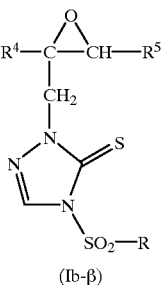 | —CH₃ |
|  | 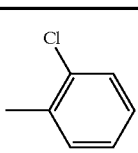 | —CH₃ |
|  |  | 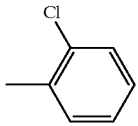 |
|  | 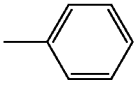 | 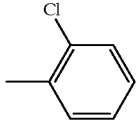 |
| 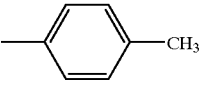 |  | 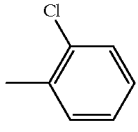 |
| 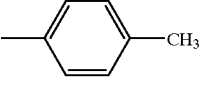 | 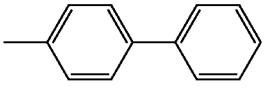 | 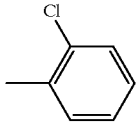 |
| 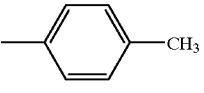 | 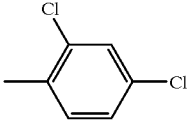 | 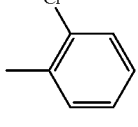 |
| 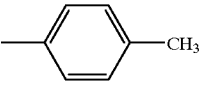 | 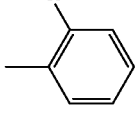 | 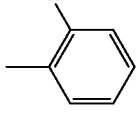 |

TABLE 2-continued
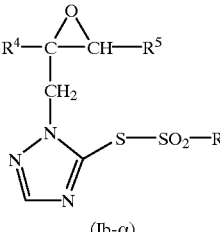
| R⁴ | R⁵ | R |
|---|---|---|
| 4-CH₃-C₆H₄- | 2-Cl-C₆H₄- | 4-CH₃-C₆H₄- |
| 3-Br-4-F-C₆H₃- | 2-Cl-C₆H₄- | 4-CH₃-C₆H₄- |
| 4-Br-C₆H₄- | 2-Cl-C₆H₄- | 4-CH₃-C₆H₄- |
| 3,4-Cl₂-C₆H₃- | 2-Cl-C₆H₄- | 4-CH₃-C₆H₄- |
| 4-F-C₆H₄- | 2-Cl-C₆H₄- | 4-CH₃-C₆H₄- |
| 4-C(CH₃)₃-C₆H₄- | 2-Cl-C₆H₄- | 4-CH₃-C₆H₄- |
| 3-Cl-C₆H₄- | 2-Cl-C₆H₄- | 4-CH₃-C₆H₄- |
| 3,5-Cl₂-C₆H₃- | 2-Cl-C₆H₄- | 4-CH₃-C₆H₄- |

TABLE 2-continued

| R⁴ | R⁵ | R |
|---|---|---|
| 4-phenoxyphenyl | 2-chlorophenyl | 4-methylphenyl |
| 4-(trifluoromethoxy)phenyl | 2-chlorophenyl | 4-methylphenyl |
| 4-(trifluoromethylthio)phenyl | 2-chlorophenyl | 4-methylphenyl |
| 4-fluorophenyl | 2-(difluoromethoxy)phenyl | 4-methylphenyl |
| 4-chlorophenyl | 2-fluorophenyl | 4-methylphenyl |
| 4-biphenyl | 2-fluorophenyl | 4-methylphenyl |
| phenyl | 2-fluorophenyl | 4-methylphenyl |
| 2,4-dichlorophenyl | 2-fluorophenyl | 4-methylphenyl |

TABLE 2-continued

| | | |
|---|---|---|
| \\ / (Ib-α) structure | and | \\ / (Ib-β) structure |

| $R^4$ | $R^5$ | R |
|---|---|---|
| 2-Cl-phenyl | 2-F-phenyl | 4-CH₃-phenyl |
| 2-F-phenyl | 2-F-phenyl | 4-CH₃-phenyl |
| 4-CH₃-phenyl | 2-F-phenyl | 4-CH₃-phenyl |
| 4-F-phenyl | 2-F-phenyl | 4-CH₃-phenyl |
| 3-Br-4-F-phenyl | 2-F-phenyl | 4-CH₃-phenyl |
| 4-Br-phenyl | 2-F-phenyl | 4-CH₃-phenyl |
| 3,4-diCl-phenyl | 2-F-phenyl | 4-CH₃-phenyl |
| 4-C(CH₃)₃-phenyl | 2-F-phenyl | 4-CH₃-phenyl |

TABLE 2-continued

| | | |
|---|---|---|
| (Ib-α) structure | and | (Ib-β) structure |

| R⁴ | R⁵ | R |
|---|---|---|
| 3-Cl-phenyl | 2-F-phenyl | 4-CH₃-phenyl |
| 3,5-diCl-phenyl | 2-F-phenyl | 4-CH₃-phenyl |
| 4-phenoxyphenyl | 2-F-phenyl | 4-CH₃-phenyl |
| 4-Cl-phenyl | 2-Br-phenyl | 4-CH₃-phenyl |
| phenyl | 2-Br-phenyl | 4-CH₃-phenyl |
| 4-biphenyl | 2-Br-phenyl | 4-CH₃-phenyl |
| 2,4-diCl-phenyl | 2-Br-phenyl | 4-CH₃-phenyl |

TABLE 2-continued
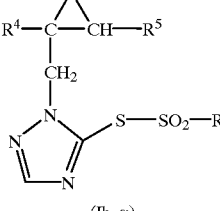
| R⁴ | R⁵ | R |
|---|---|---|
| 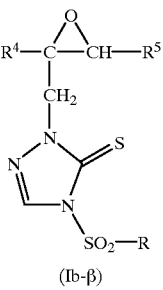 | 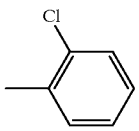 | 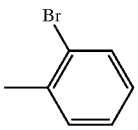 |
| 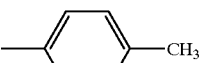 | 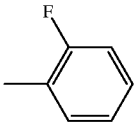 | 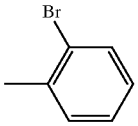 |
| 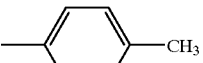 | 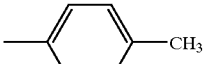 | 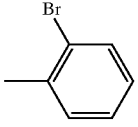 |
| 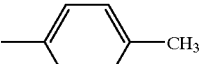 |  | 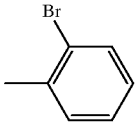 |
| 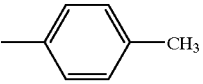 | 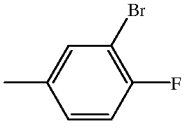 | 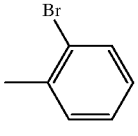 |
| 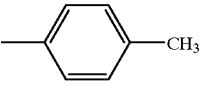 |  | 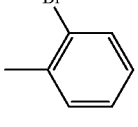 |
| 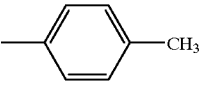 | 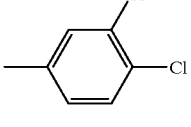 | 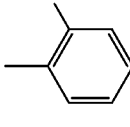 |
| 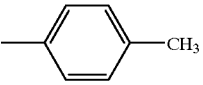 | 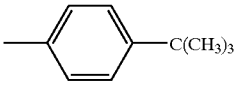 | 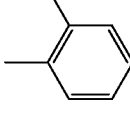 |

TABLE 2-continued

| | | |
|---|---|---|
| R⁴-C(O-CH)-CH₂-N(triazole)-S-SO₂-R with R⁵ (Ib-α) | and | R⁴-C(O-CH-R⁵)-CH₂-N(triazole-thione)-SO₂-R (Ib-β) |

| R⁴ | R⁵ | R |
|---|---|---|
| 3-chlorophenyl | 2-bromophenyl | 4-methylphenyl |
| —C(CH₃)₂CH₂F | 2-chlorophenyl | 4-methylphenyl |
| 3,5-dichlorophenyl | 2-bromophenyl | 4-methylphenyl |
| 4-phenoxyphenyl | 2-bromophenyl | 4-methylphenyl |
| —CH₃ | 2-chlorophenyl | 4-methylphenyl |
| —CH₃ | 2-fluorophenyl | 4-methylphenyl |
| —CH₃ | 2-bromophenyl | 4-methylphenyl |
| —C(CH₃)₃ | 2-chlorophenyl | 4-methylphenyl |

TABLE 2-continued

Structures (Ib-α) and (Ib-β):

(Ib-α): 1H-1,2,4-triazole with N1 substituted by –CH$_2$–C(R$^4$)(epoxide)–CH–R$^5$, and 5-position bearing –S–SO$_2$–R (Ib-β): 2,4-dihydro-3H-1,2,4-triazole-3-thione with N1 substituted by –CH$_2$–C(R$^4$)(epoxide)–CH–R$^5$, and N4 substituted by –SO$_2$–R

| R$^4$ | R$^5$ | R |
|---|---|---|
| 1-chlorocyclopropyl | 2-chlorophenyl | 4-methylphenyl |

TABLE 3

Structures (Ic-α) and (Ic-β):

(Ic-α): cyclopentane bearing R$^6$, R$^7$ geminal substituents, OH, –CH$_2$–(1,2,4-triazol-1-yl with 5-S–SO$_2$–R), and –CH$_2$–(phenyl with X$^1_m$)

(Ic-β): cyclopentane bearing R$^6$, R$^7$, OH, –CH$_2$–(1,2,4-triazole-3-thione, N4–SO$_2$–R), and –CH$_2$–(phenyl with X$^1_m$)

| R$^6$ | R$^7$ | R | X$^1_m$ |
|---|---|---|---|
| —CH$_3$ | —CH$_3$ | —CH$_3$ | 4-Br |
| —CH$_3$ | —CH$_3$ | —CH$_3$ | 4-F |
| —CH$_3$ | —CH$_3$ | —CH$_3$ | 2,4-Cl$_2$ |
| —CH$_3$ | H | —CH$_3$ | 4-Cl |
| —CH$_3$ | —CH$_3$ | —CH$_3$ | — |
| —CH$_3$ | —CH$_3$ | —CH$_3$ | 4-CH$_3$ |
| —CH$_3$ | —CH$_3$ | —CH$_3$ | 2-F, 4-Cl |
| —C$_2$H$_5$ | H | —CH$_3$ | 4-Cl |
| —C$_2$H$_5$ | —C$_2$H$_5$ | —CH$_3$ | 4-Cl |
| —C$_3$H$_7$-n | H | —CH$_3$ | 4-Cl |
| —C$_2$H$_5$ | H | —CH$_3$ | 2,4-Cl$_2$ |
| —C$_2$H$_5$ | H | —CH$_3$ | 4-F |
| —C$_2$H$_5$ | H | —CH$_3$ | 4-Br |
| —C$_2$H$_5$ | H | —CH$_3$ | 4-phenyl |
| —C$_2$H$_5$ | H | —CH$_3$ | 4-C$_4$H$_9$-t |
| —C$_3$H$_7$-i | H | —CH$_3$ | 4-Cl |
| —C$_5$H$_{11}$-n | H | —CH$_3$ | 4-Cl |
| —CH$_3$ | —CH$_3$ | —CH$_3$ | 4-phenyl |
| —CH$_3$ | —CH$_3$ | —CH$_3$ | 4-C$_4$H$_9$-t |
| —C$_4$H$_9$-n | H | —CH$_3$ | 4-Cl |
| —C$_4$H$_9$-i | H | —CH$_3$ | 4-Cl |
| —CH$_3$ | —C$_2$H$_5$ | —CH$_3$ | 4-Cl |
| —CH$_3$ | —CH$_3$ | 4-methylphenyl | 4-Cl |

TABLE 3-continued (Ic-α)

(Ic-β)

and

| R⁶ | R⁷ | R | X¹ₘ |
|---|---|---|---|
| —CH₃ | —CH₃ | 4-CH₃-C₆H₄— | 4-Br |
| —CH₃ | —CH₃ | 4-CH₃-C₆H₄— | 4-F |
| —CH₃ | —CH₃ | 4-CH₃-C₆H₄— | 2,4-Cl₂ |
| —CH₃ | H | 4-CH₃-C₆H₄— | 4-Cl |
| —CH₃ | —CH₃ | 4-CH₃-C₆H₄— | — |
| —CH₃ | —CH₃ | 4-CH₃-C₆H₄— | 4-CH₃ |
| —CH₃ | —CH₃ | 4-CH₃-C₆H₄— | 2-F, 4-Cl |
| —C₂H₅ | H | 4-CH₃-C₆H₄— | 4-Cl |
| —C₂H₅ | —C₂H₅ | 4-CH₃-C₆H₄— | 4-Cl |
| —C₃H₇-n | H | 4-CH₃-C₆H₄— | 4-Cl |
| —C₂H₅ | H | 4-CH₃-C₆H₄— | 2,4-Cl₂ |
| —C₂H₅ | H | 4-CH₃-C₆H₄— | 4-F |
| —C₂H₅ | H | 4-CH₃-C₆H₄— | 4-Br |
| —C₂H₅ | H | 4-CH₃-C₆H₄— | 4-C₆H₅ |
| —C₂H₅ | H | 4-CH₃-C₆H₄— | 4-C₄H₉-t |
| —C₃H₇-i | H | 4-CH₃-C₆H₄— | 4-Cl |

TABLE 3-continued

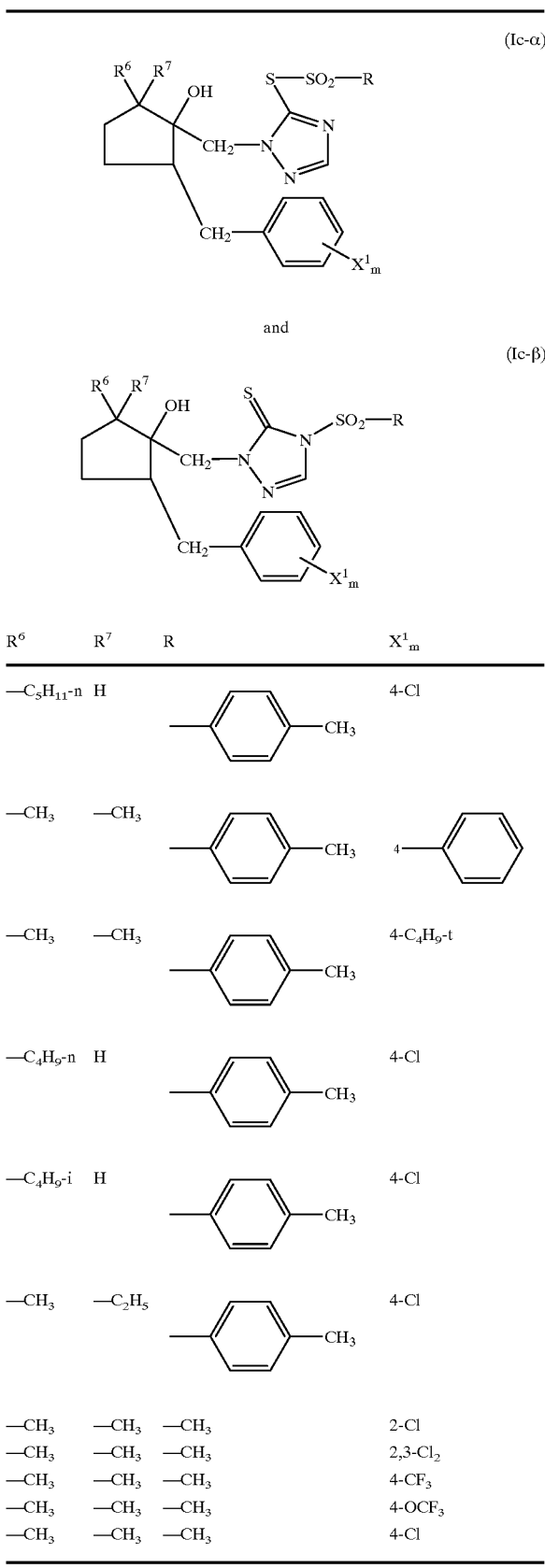

(Ic-α)

and (Ic-β)

| R[6] | R[7] | R | X[1]$_m$ |
|---|---|---|---|
| —C$_5$H$_{11}$-n | H | | 4-Cl |
| —CH$_3$ | —CH$_3$ | | 4- |
| —CH$_3$ | —CH$_3$ | | 4-C$_4$H$_9$-t |
| —C$_4$H$_9$-n | H | | 4-Cl |
| —C$_4$H$_9$-i | H | | 4-Cl |
| —CH$_3$ | —C$_2$H$_5$ | | 4-Cl |
| —CH$_3$ | —CH$_3$ | —CH$_3$ | 2-Cl |
| —CH$_3$ | —CH$_3$ | —CH$_3$ | 2,3-Cl$_2$ |
| —CH$_3$ | —CH$_3$ | —CH$_3$ | 4-CF$_3$ |
| —CH$_3$ | —CH$_3$ | —CH$_3$ | 4-OCF$_3$ |
| —CH$_3$ | —CH$_3$ | —CH$_3$ | 4-Cl |

TABLE 4

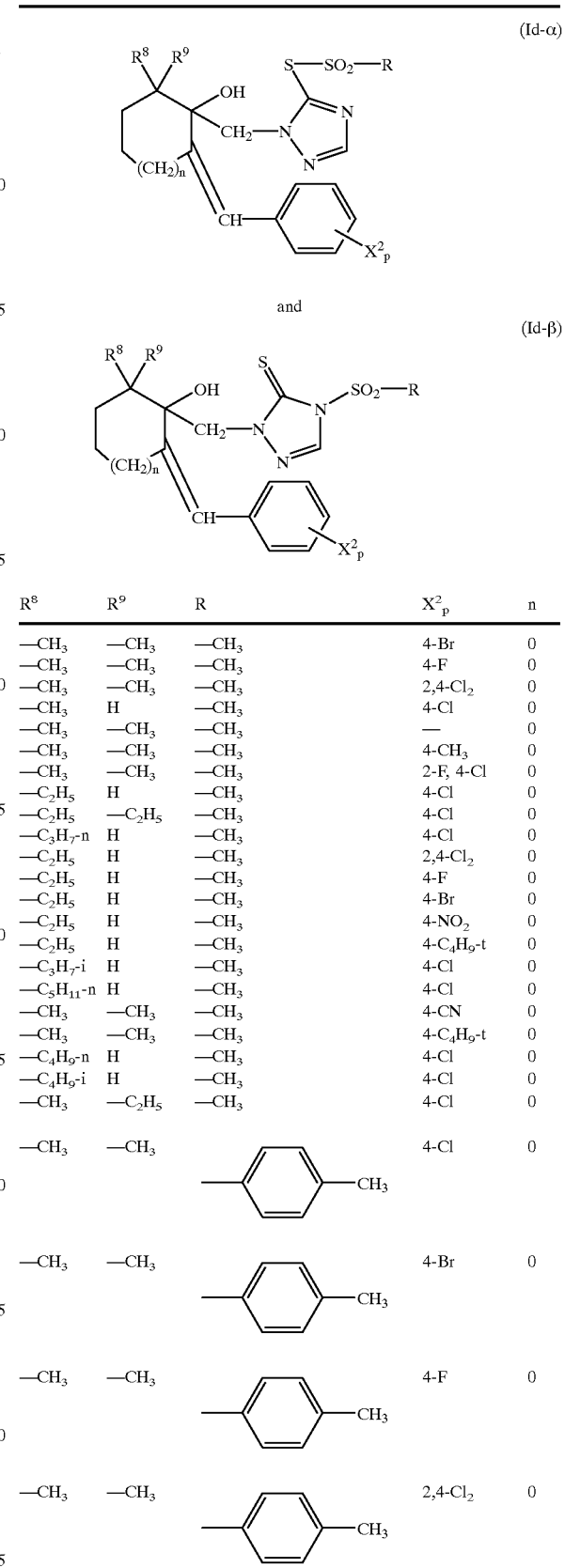

(Id-α)

and (Id-β)

| R[8] | R[9] | R | X[2]$_p$ | n |
|---|---|---|---|---|
| —CH$_3$ | —CH$_3$ | —CH$_3$ | 4-Br | 0 |
| —CH$_3$ | —CH$_3$ | —CH$_3$ | 4-F | 0 |
| —CH$_3$ | —CH$_3$ | —CH$_3$ | 2,4-Cl$_2$ | 0 |
| —CH$_3$ | H | —CH$_3$ | 4-Cl | 0 |
| —CH$_3$ | —CH$_3$ | —CH$_3$ | — | 0 |
| —CH$_3$ | —CH$_3$ | —CH$_3$ | 4-CH$_3$ | 0 |
| —CH$_3$ | —CH$_3$ | —CH$_3$ | 2-F, 4-Cl | 0 |
| —C$_2$H$_5$ | H | —CH$_3$ | 4-Cl | 0 |
| —C$_2$H$_5$ | —C$_2$H$_5$ | —CH$_3$ | 4-Cl | 0 |
| —C$_3$H$_7$-n | H | —CH$_3$ | 4-Cl | 0 |
| —C$_2$H$_5$ | H | —CH$_3$ | 2,4-Cl$_2$ | 0 |
| —C$_2$H$_5$ | H | —CH$_3$ | 4-F | 0 |
| —C$_2$H$_5$ | H | —CH$_3$ | 4-Br | 0 |
| —C$_2$H$_5$ | H | —CH$_3$ | 4-NO$_2$ | 0 |
| —C$_2$H$_5$ | H | —CH$_3$ | 4-C$_4$H$_9$-t | 0 |
| —C$_3$H$_7$-i | H | —CH$_3$ | 4-Cl | 0 |
| —C$_5$H$_{11}$-n | H | —CH$_3$ | 4-Cl | 0 |
| —CH$_3$ | —CH$_3$ | —CH$_3$ | 4-CN | 0 |
| —CH$_3$ | —CH$_3$ | —CH$_3$ | 4-C$_4$H$_9$-t | 0 |
| —C$_4$H$_9$-n | H | —CH$_3$ | 4-Cl | 0 |
| —C$_4$H$_9$-i | H | —CH$_3$ | 4-Cl | 0 |
| —CH$_3$ | —C$_2$H$_5$ | —CH$_3$ | 4-Cl | 0 |
| —CH$_3$ | —CH$_3$ | | 4-Cl | 0 |
| —CH$_3$ | —CH$_3$ | | 4-Br | 0 |
| —CH$_3$ | —CH$_3$ | | 4-F | 0 |
| —CH$_3$ | —CH$_3$ | | 2,4-Cl$_2$ | 0 |

TABLE 4-continued $$\begin{array}{c}\text{(Id-}\alpha\text{)}\end{array}$$

[Structure Id-α: cycloalkane with R8, R9, OH, CH2 linked to triazole bearing S—SO2—R, with (CH2)n and =CH-phenyl-X²p]

and $$\begin{array}{c}\text{(Id-}\beta\text{)}\end{array}$$

[Structure Id-β: cycloalkane with R8, R9, OH, CH2 linked to thione-triazole bearing N—SO2—R, with (CH2)n and =CH-phenyl-X²p]

| $R^8$ | $R^9$ | R | $X^2_p$ | n |
|---|---|---|---|---|
| —CH$_3$ | H | -C$_6$H$_4$-CH$_3$ (p) | 4-Cl | 0 |
| —CH$_3$ | —CH$_3$ | -C$_6$H$_4$-CH$_3$ (p) | — | 0 |
| —CH$_3$ | —CH$_3$ | -C$_6$H$_4$-CH$_3$ (p) | 4-CH$_3$ | 0 |
| —CH$_3$ | —CH$_3$ | -C$_6$H$_4$-CH$_3$ (p) | 2-F, 4-Cl | 0 |
| —C$_2$H$_5$ | H | -C$_6$H$_4$-CH$_3$ (p) | 4-Cl | 0 |
| —C$_2$H$_5$ | —C$_2$H$_5$ | -C$_6$H$_4$-CH$_3$ (p) | 4-Cl | 0 |
| —C$_3$H$_7$-n | H | -C$_6$H$_4$-CH$_3$ (p) | 4-Cl | 0 |
| —C$_2$H$_5$ | H | -C$_6$H$_4$-CH$_3$ (p) | 2,4-Cl$_2$ | 0 |
| —C$_2$H$_5$ | H | -C$_6$H$_4$-CH$_3$ (p) | 4-F | 0 |
| —C$_2$H$_5$ | H | -C$_6$H$_4$-CH$_3$ (p) | 4-Br | 0 |
| —C$_2$H$_5$ | H | -C$_6$H$_4$-CH$_3$ (p) | 4-NO$_2$ | 0 |
| —C$_2$H$_5$ | H | -C$_6$H$_4$-CH$_3$ (p) | 4-C$_4$H$_9$-t | 0 |
| —C$_3$H$_7$-i | H | -C$_6$H$_4$-CH$_3$ (p) | 4-Cl | 0 |
| —C$_5$H$_{11}$-n | H | -C$_6$H$_4$-CH$_3$ (p) | 4-Cl | 0 |
| —CH$_3$ | —CH$_3$ | -C$_6$H$_4$-CH$_3$ (p) | 4-CN | 0 |
| —CH$_3$ | —CH$_3$ | -C$_6$H$_4$-CH$_3$ (p) | 4-C$_4$H$_9$-t | 0 |
| —C$_4$H$_9$-n | H | -C$_6$H$_4$-CH$_3$ (p) | 4-Cl | 0 |
| —C$_4$H$_9$-i | H | -C$_6$H$_4$-CH$_3$ (p) | 4-Cl | 0 |

TABLE 4-continued (Id-α)

$$\text{Structure (Id-α): cyclohexane ring with } R^8, R^9 \text{ substituents, OH, CH}_2\text{-triazole linked to S-SO}_2\text{-R, and (CH}_2)_n\text{-CH=aryl with } X^2_p$$

and (Id-β)

$$\text{Structure (Id-β): cyclohexane ring with } R^8, R^9, \text{OH, CH}_2\text{-triazole (C=S) with N-SO}_2\text{-R, and (CH}_2)_n\text{-CH=aryl with } X^2_p$$

| $R^8$ | $R^9$ | R | $X^2_p$ | n |
|---|---|---|---|---|
| —CH$_3$ | —C$_2$H$_5$ | ⟨4-CH$_3$-phenyl⟩ | 4-Cl | 0 |
| —CH$_3$ | —CH$_3$ | —CH$_3$ | 4-OCH$_3$ | 0 |
| —CH$_3$ | —CH$_3$ | —CH$_3$ | 2-OCH$_3$ | 0 |
| —CH$_3$ | —CH$_3$ | —CH$_3$ | 2-CF$_3$ | 0 |
| —CH$_3$ | —CH$_3$ | —CH$_3$ | 4-CF$_3$ | 0 |
| —CH$_3$ | —CH$_3$ | —CH$_3$ | 2-OCF$_3$ | 0 |
| —CH$_3$ | —CH$_3$ | —CH$_3$ | 2-OCHF$_2$ | 0 |
| —CH$_3$ | —CH$_3$ | —CH$_3$ | 4-OCF$_3$ | 0 |
| —CH$_3$ | —CH$_3$ | ⟨4-CH$_3$-phenyl⟩ | 4-OCH$_3$ | 0 |
| —CH$_3$ | —CH$_3$ | ⟨4-CH$_3$-phenyl⟩ | 2-OCH$_3$ | 0 |
| —CH$_3$ | —CH$_3$ | ⟨4-CH$_3$-phenyl⟩ | 2-CF$_3$ | 0 |
| —CH$_3$ | —CH$_3$ | ⟨4-CH$_3$-phenyl⟩ | 4-CF$_3$ | 0 |
| —CH$_3$ | —CH$_3$ | ⟨4-CH$_3$-phenyl⟩ | 2-OCF$_3$ | 0 |
| —CH$_3$ | —CH$_3$ | ⟨4-CH$_3$-phenyl⟩ | 2-OCHF$_2$ | 0 |

| $R^8$ | $R^9$ | R | $X^2_p$ | n |
|---|---|---|---|---|
| —CH$_3$ | —CH$_3$ | ⟨4-CH$_3$-phenyl⟩ | 4-OCF$_3$ | 0 |
| —CH$_3$ | —CH$_3$ | —CH$_3$ | 4-Br | 1 |
| —CH$_3$ | —CH$_3$ | —CH$_3$ | 4-F | 1 |
| —CH$_3$ | —CH$_3$ | —CH$_3$ | 2,4-Cl$_2$ | 1 |
| —CH$_3$ | H | —CH$_3$ | 4-Cl | 1 |
| —CH$_3$ | —CH$_3$ | —CH$_3$ | — | 1 |
| —CH$_3$ | —CH$_3$ | —CH$_3$ | 4-CH$_3$ | 1 |
| —CH$_3$ | —CH$_3$ | —CH$_3$ | 2-F, 4-Cl | 1 |
| —C$_2$H$_5$ | H | —CH$_3$ | 4-Cl | 1 |
| —C$_2$H$_5$ | —C$_2$H$_5$ | —CH$_3$ | 4-Cl | 1 |
| —C$_3$H$_7$-n | H | —CH$_3$ | 4-Cl | 1 |
| —C$_2$H$_5$ | H | —CH$_3$ | 2,4-Cl$_2$ | 1 |
| —C$_2$H$_5$ | H | —CH$_3$ | 4-F | 1 |
| —C$_2$H$_5$ | H | —CH$_3$ | 4-Br | 1 |
| —C$_2$H$_5$ | H | —CH$_3$ | 4-NO$_2$ | 1 |
| —C$_2$H$_5$ | H | —CH$_3$ | 4-C$_4$H$_9$-t | 1 |
| —C$_3$H$_7$-i | H | —CH$_3$ | 4-Cl | 1 |
| —C$_5$H$_{11}$-n | H | —CH$_3$ | 4-Cl | 1 |
| —CH$_3$ | —CH$_3$ | —CH$_3$ | 4-CN | 1 |
| —CH$_3$ | —CH$_3$ | —CH$_3$ | 4-C$_4$H$_9$-t | 1 |
| —C$_4$H$_9$-n | H | —CH$_3$ | 4-Cl | 1 |
| —CH$_3$ | —CH$_3$ | —CH$_3$ | 4-Cl | 1 |
| —CH$_3$ | —CH$_3$ | ⟨4-CH$_3$-phenyl⟩ | 4-Cl | 1 |
| —C$_4$H$_9$-i | H | —CH$_3$ | 4-Cl | 1 |
| —CH$_3$ | —C$_2$H$_5$ | —CH$_3$ | 4-Cl | 1 |
| —CH$_3$ | —CH$_3$ | ⟨4-CH$_3$-phenyl⟩ | 4-Cl | 1 |
| —CH$_3$ | —CH$_3$ | ⟨4-CH$_3$-phenyl⟩ | 4-Br | 1 |

TABLE 4-continued (Id-α)

$$\text{structure with } R^8, R^9, OH, CH_2, (CH_2)_n, \text{triazole with } S\text{-}SO_2\text{-}R, \text{ and } CH\text{=}C_6H_4\text{-}X^2_p$$

and (Id-β)

$$\text{structure with } R^8, R^9, OH, CH_2, (CH_2)_n, \text{triazole-thione with } N\text{-}SO_2\text{-}R, \text{ and } CH\text{=}C_6H_4\text{-}X^2_p$$

| $R^8$ | $R^9$ | R | $X^2_p$ | n |
|---|---|---|---|---|
| —CH$_3$ | —CH$_3$ | 4-CH$_3$-C$_6$H$_4$— | 4-F | 1 |
| —CH$_3$ | —CH$_3$ | 4-CH$_3$-C$_6$H$_4$— | 2,4-Cl$_2$ | 1 |
| —CH$_3$ | H | 4-CH$_3$-C$_6$H$_4$— | 4-Cl | 1 |
| —CH$_3$ | —CH$_3$ | 4-CH$_3$-C$_6$H$_4$— | — | 1 |
| —CH$_3$ | —CH$_3$ | 4-CH$_3$-C$_6$H$_4$— | 4-CH$_3$ | 1 |
| —CH$_3$ | —CH$_3$ | 4-CH$_3$-C$_6$H$_4$— | 2-F, 4-Cl | 1 |
| —C$_2$H$_5$ | H | 4-CH$_3$-C$_6$H$_4$— | 4-Cl | 1 |
| —C$_2$H$_5$ | —C$_2$H$_5$ | 4-CH$_3$-C$_6$H$_4$— | 4-Cl | 1 |
| —C$_3$H$_7$-n | H | 4-CH$_3$-C$_6$H$_4$— | 4-Cl | 1 |
| —C$_2$H$_5$ | H | 4-CH$_3$-C$_6$H$_4$— | 2,4-Cl$_2$ | 1 |
| —C$_2$H$_5$ | H | 4-CH$_3$-C$_6$H$_4$— | 4-F | 1 |
| —C$_2$H$_5$ | H | 4-CH$_3$-C$_6$H$_4$— | 4-Br | 1 |
| —C$_2$H$_5$ | H | 4-CH$_3$-C$_6$H$_4$— | 4-NO$_2$ | 1 |
| —C$_2$H$_5$ | H | 4-CH$_3$-C$_6$H$_4$— | 4-C$_4$H$_9$-t | 1 |
| —C$_3$H$_7$-i | H | 4-CH$_3$-C$_6$H$_4$— | 4-Cl | 1 |
| —C$_5$H$_{11}$-n | H | 4-CH$_3$-C$_6$H$_4$— | 4-Cl | 1 |

TABLE 4-continued (Id-α)

[Structure: cycloalkane ring with R8, R9 substituents, OH, CH2 linked to 1,2,4-triazole bearing S-SO2-R, and (CH2)n=CH-phenyl-X²p]

and (Id-β)

[Structure: cycloalkane ring with R8, R9 substituents, OH, CH2 linked to 1,2,4-triazole-3-thione bearing N-SO2-R, and (CH2)n=CH-phenyl-X²p]

| R⁸ | R⁹ | R | X²p | n |
|---|---|---|---|---|
| —CH₃ | —CH₃ | ―⟨C₆H₄⟩―CH₃ | 4-CN | 1 |
| —CH₃ | —CH₃ | ―⟨C₆H₄⟩―CH₃ | 4-C₄H₉-t | 1 |
| —C₄H₉-n | H | ―⟨C₆H₄⟩―CH₃ | 4-Cl | 1 |
| —C₄H₉-i | H | ―⟨C₆H₄⟩―CH₃ | 4-Cl | 1 |
| —CH₃ | —C₂H₅ | ―⟨C₆H₄⟩―CH₃ | 4-Cl | 1 |
| —CH₃ | —CH₃ | —CH₃ | 4-OCH₃ | 1 |
| —CH₃ | —CH₃ | —CH₃ | 2-OCH₃ | 1 |
| —CH₃ | —CH₃ | —CH₃ | 2-CF₃ | 1 |
| —CH₃ | —CH₃ | —CH₃ | 4-CF₃ | 1 |
| —CH₃ | —CH₃ | —CH₃ | 2-OCF₃ | 1 |
| —CH₃ | —CH₃ | —CH₃ | 2-OCHF₂ | 1 |
| —CH₃ | —CH₃ | —CH₃ | 4-OCF₃ | 1 |
| —CH₃ | —CH₃ | ―⟨C₆H₄⟩―CH₃ | 4-OCH₃ | 1 |
| —CH₃ | —CH₃ | ―⟨C₆H₄⟩―CH₃ | 2-OCH₃ | 1 |
| —CH₃ | —CH₃ | ―⟨C₆H₄⟩―CH₃ | 2-CF₃ | 1 |
| —CH₃ | —CH₃ | ―⟨C₆H₄⟩―CH₃ | 4-CF₃ | 1 |
| —CH₃ | —CH₃ | ―⟨C₆H₄⟩―CH₃ | 2-OCF₃ | 1 |
| —CH₃ | —CH₃ | ―⟨C₆H₄⟩―CH₃ | 2-OCHF₂ | 1 |
| —CH₃ | —CH₃ | ―⟨C₆H₄⟩―CH₃ | 4-OCF₃ | 1 |
| —CH₃ | —CH₃ | —CH₃ | 2-Cl | 0 |
| —CH₃ | —CH₃ | —CH₃ | 2,3-Cl₂ | 0 |
| —CH₃ | —CH₃ | —CH₃ | 2-Cl | 1 |
| —CH₃ | —CH₃ | —CH₃ | 4-Cl | 0 |

TABLE 5
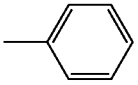
(Ie-α)
and
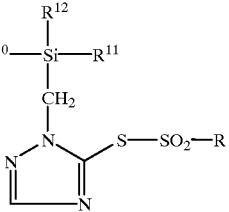
(Ie-β)
| R[10] | R[11] | R[12] | R |
|---|---|---|---|
| 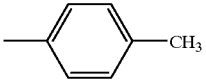 | —CH$_3$ | —CH$_3$ | —CH$_3$ |
| 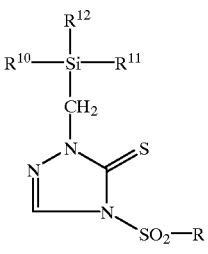 | —CH$_3$ | —CH$_3$ | —CH$_3$ |
|  | —CH$_3$ | —CH$_3$ | —CH$_3$ |
| 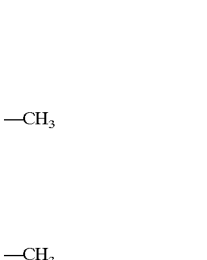 | —CH$_3$ | —CH$_3$ | —CH$_3$ |
| 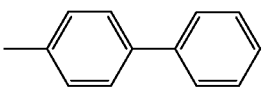 | —CH$_3$ | —CH$_3$ | —CH$_3$ |
| 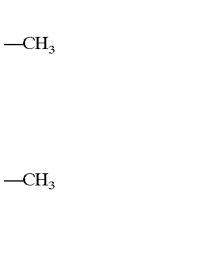 | —CH$_3$ | —CH$_3$ | —CH$_3$ |
|  | —C$_4$H$_9$-n | —CH$_3$ | —CH$_3$ |

TABLE 5-continued
(Ie-α)
and
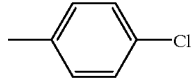
(Ie-β)
| R¹⁰ | R¹¹ | R¹² | R |
|---|---|---|---|
| 4-Cl-C₆H₄ | 4-Cl-C₆H₄ | —CH₃ | —CH₃ |
| C₆H₅ | C₆H₅ | —CH₃ | —CH₃ |
| 4-F-C₆H₄ | —CH₃ | —CH₃ | —CH₃ |
| 2,4-Cl₂-C₆H₃ | —C₄H₉-n | —CH₃ | —CH₃ |
| 2,4-Cl₂-C₆H₃ | 2,4-Cl₂-C₆H₃ | —CH₃ | —CH₃ |
| 2,4-Cl₂-C₆H₃ | C₆H₅ | —CH₃ | —CH₃ |
| 4-Cl-C₆H₄ | C₆H₅ | —CH₃ | —CH₃ |

TABLE 5-continued (Ie-α)

$$\begin{array}{c} R^{12} \\ | \\ R^{10}-Si-R^{11} \\ | \\ CH_2 \\ | \\ \text{[1,2,4-triazole ring]}-S-SO_2-R \end{array}$$

and (Ie-β)

$$\begin{array}{c} R^{12} \\ | \\ R^{10}-Si-R^{11} \\ | \\ CH_2 \\ | \\ \text{[1,2,4-triazole-3-thione]}-N-SO_2-R \end{array}$$

| $R^{10}$ | $R^{11}$ | $R^{12}$ | R |
|---|---|---|---|
| 4-F-C$_6$H$_4$– | C$_6$H$_5$– | –CH$_3$ | –CH$_3$ |
| C$_6$H$_5$– | –C$_4$H$_9$-n | –CH$_3$ | –CH$_3$ |
| 4-F-C$_6$H$_4$– | –C$_4$H$_9$-n | –CH$_3$ | –CH$_3$ |
| 4-biphenylyl | 4-biphenylyl | –CH$_3$ | –CH$_3$ |
| 4-biphenylyl | –C$_4$H$_9$-n | –CH$_3$ | –CH$_3$ |
| 4-biphenylyl | pyridyl | –CH$_3$ | –CH$_3$ |
| C$_6$H$_5$– | –CH$_3$ | –CH$_3$ | 4-CH$_3$-C$_6$H$_4$– |
| 4-CH$_3$-C$_6$H$_4$– | –CH$_3$ | –CH$_3$ | 4-CH$_3$-C$_6$H$_4$– |

TABLE 5-continued
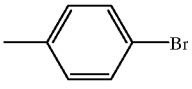
(Ie-α)
and
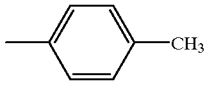
(Ie-β)
| R[10] | R[11] | R[12] | R |
|---|---|---|---|
| 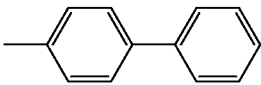 | —CH$_3$ | —CH$_3$ | 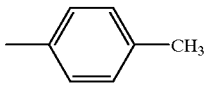 |
| 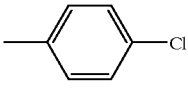 | —CH$_3$ | —CH$_3$ | 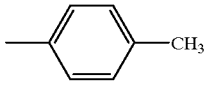 |
| 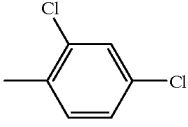 | —CH$_3$ | —CH$_3$ | 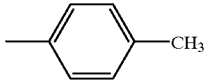 |
| 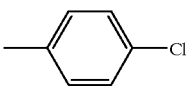 | —CH$_3$ | —CH$_3$ | 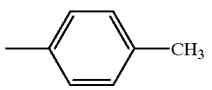 |
| 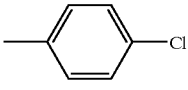 | —C$_4$H$_9$-n | —CH$_3$ | 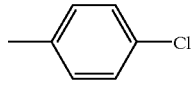 |
| 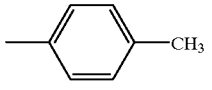 | 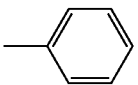 | —CH$_3$ | 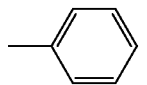 |
| 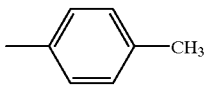 | | —CH$_3$ | |

TABLE 5-continued
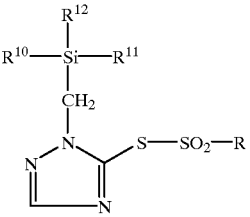
(Ie-α)
and
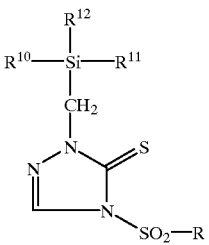
(Ie-β)
| $R^{10}$ | $R^{11}$ | $R^{12}$ | R |
|---|---|---|---|
|  | —CH$_3$ | —CH$_3$ | 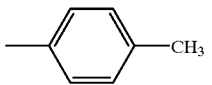 |
| 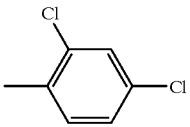 | —C$_4$H$_9$-n | —CH$_3$ | 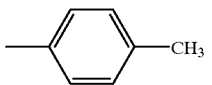 |
| 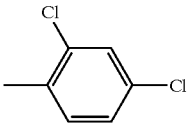 | 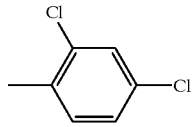 | —CH$_3$ | 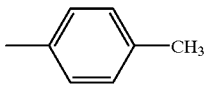 |
| 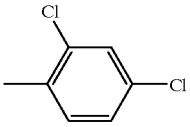 | 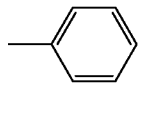 | —CH$_3$ | 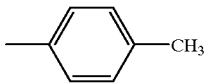 |
|  | 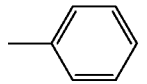 | —CH$_3$ | 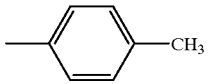 |
|  | 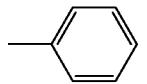 | —CH$_3$ | 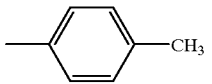 |
| 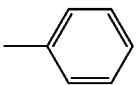 | —C$_4$H$_9$-n | —CH$_3$ | 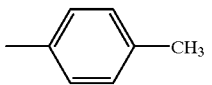 |

TABLE 5-continued
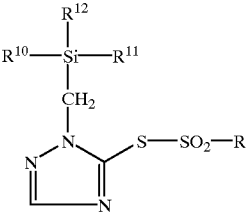
(Ie-α)
and
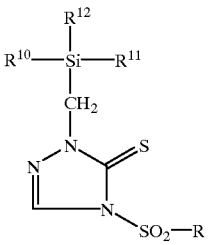
(Ie-β)
| R$^{10}$ | R$^{11}$ | R$^{12}$ | R |
|---|---|---|---|
| 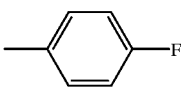 | —C$_4$H$_9$-n | —CH$_3$ |  |
|  | 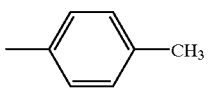 | —CH$_3$ | 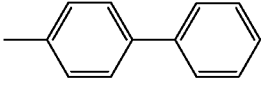 |
| 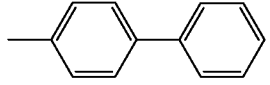 | —C$_4$H$_9$-n | —CH$_3$ |  |
| 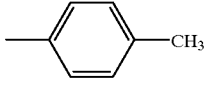 | 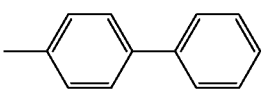 | —CH$_3$ |  |
|  | 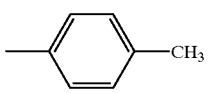 | —CH$_3$ CH$_3$ | |
| 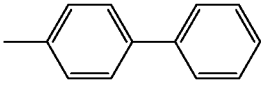 | 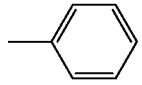 | —CH$_3$ |  |

TABLE 6

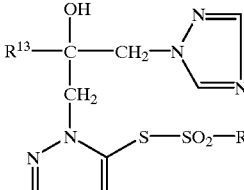 (If-α)

and

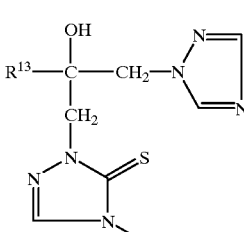 (If-β)

| $R^{13}$ | R |
|---|---|
| 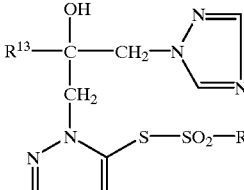 4-Cl-phenyl | —CH$_3$ |
| 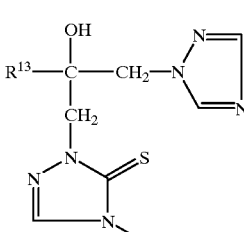 phenyl | —CH$_3$ |
| 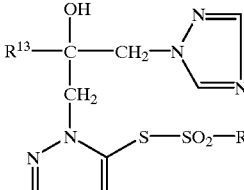 4-F-phenyl | —CH$_3$ |
| 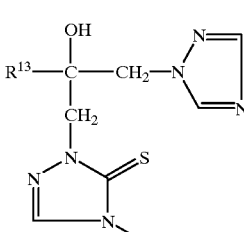 2,4-diCl-phenyl | —CH$_3$ |
| 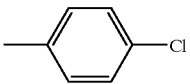 4-CH$_3$-phenyl | —CH$_3$ |
|  4-pyridyl-phenyl | —CH$_3$ |
| 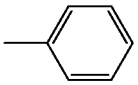 4-OCH$_3$-phenyl | —CH$_3$ |
|  4-phenoxy-phenyl | —CH$_3$ |
|  2-CF$_3$-phenyl | —CH$_3$ |
| —C$_4$H$_9$-n | —CH$_3$ |
| —C(CH$_3$)$_3$ | —CH$_3$ |
| —CH(CH$_3$)$_2$ | —CH$_3$ |
|  —C(CH$_2$Cl)$_2$CH$_3$ | —CH$_3$ |
| 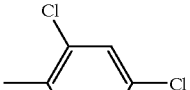 —C(CH$_2$F)$_2$CH$_3$ | —CH$_3$ |
| —CH$_2$—CH(CH$_3$)$_2$ | —CH$_3$ |
|  cyclopropyl | —CH$_3$ |
| 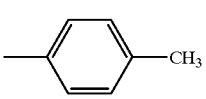 cyclopentyl | —CH$_3$ |
|  cyclohexyl | —CH$_3$ |
| 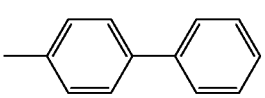 1-methylcyclopropyl | —CH$_3$ |
|  1-chlorocyclopropyl | —CH$_3$ |

TABLE 6-continued $$\text{R}^{13}-\underset{\underset{CH_2}{|}}{\overset{\overset{OH}{|}}{C}}-CH_2-N\underset{N}{\overset{N}{\diagdown}}\underset{}{\diagup} \quad \text{(If-α)}$$

$$\underset{N\diagdown_N\diagup}{|}$$
$$\text{S}-SO_2-R$$

and $$\text{R}^{13}-\underset{\underset{CH_2}{|}}{\overset{\overset{OH}{|}}{C}}-CH_2-N\underset{N}{\overset{N}{\diagdown}}\underset{}{\diagup} \quad \text{(If-β)}$$

$$\underset{N\diagdown_N\diagup\text{S}}{|}$$
$$\underset{SO_2-R}{|}$$

| $R^{13}$ | R |
|---|---|
| —CH(CH₃)—C₂H₅ | —CH₃ |
| —CH₂—C₆H₄—F (4-) | —CH₃ |
| —CH(CH₃)—C₆H₅ | —CH₃ |
| —CH(CH₃)—C₆H₄—Cl (4-) | —CH₃ |
| —CH(CH₃)—C₆H₄—F (4-) | —CH₃ |
| —CH(CH₃)—C₆H₄—CF₃ (4-) | —CH₃ |
| —CH(CH₃)—C₆H₄—OCH₃ (4-) | —CH₃ |
| —CH(CH₃)—C₆H₄—OCF₃ (4-) | —CH₃ |

TABLE 6-continued (If-α)

$$R^{13}-\underset{\underset{CH_2}{\overset{OH}{|}}}{\overset{OH}{\underset{|}{C}}}-CH_2-N\diagup\text{triazole}$$
with S—SO$_2$—R substituent and (If-β)

$$R^{13}-\underset{\underset{CH_2}{\overset{OH}{|}}}{\overset{OH}{\underset{|}{C}}}-CH_2-N\diagup\text{triazole-thione}$$
with SO$_2$—R on N

| R$^{13}$ | R |
|---|---|
| 2,6-dichlorophenyl | —CH$_3$ |
| 4-(OCF$_3$)phenyl | —CH$_3$ |
| 2,4,5-trichlorophenyl | —CH$_3$ |
| 3,4-dichlorophenyl | —CH$_3$ |
| 4-chlorophenyl | 4-methylphenyl |
| phenyl | 4-methylphenyl |
| 4-fluorophenyl | 4-methylphenyl |
| 2,4-dichlorophenyl | 4-methylphenyl |
| 4-methylphenyl | 4-methylphenyl |
| 4-biphenyl | 4-methylphenyl |
| 4-methoxyphenyl | 4-methylphenyl |
| 4-phenoxyphenyl | 4-methylphenyl |
| 2-(CF$_3$)phenyl | 4-methylphenyl |
| —C$_4$H$_9$-n | 4-methylphenyl |
| —C(CH$_3$)$_3$ | 4-methylphenyl |

TABLE 6-continued

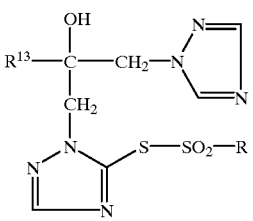 (If-α)

and

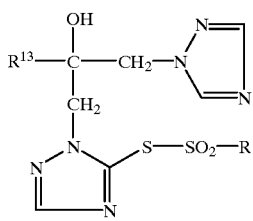 (If-β)

| R¹³ | R |
|---|---|
| —CH(CH₃)₂ | 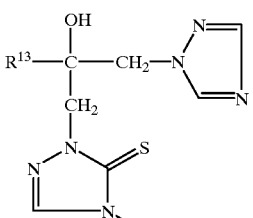—C₆H₄—CH₃ |
| 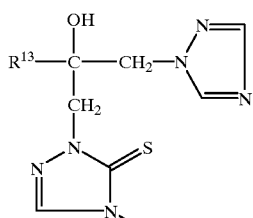 (C(CH₂Cl)₂CH₃) | 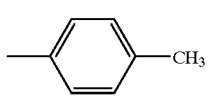—C₆H₄—CH₃ |
|  (C(CH₃)₂CH₂F) | 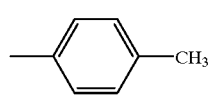—C₆H₄—CH₃ |
| —CH₂—CH(CH₃)₂ | 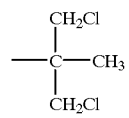—C₆H₄—CH₃ |
| 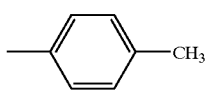 cyclopropyl | —C₆H₄—CH₃ |
| 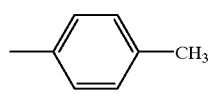 cyclopentyl | 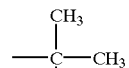—C₆H₄—CH₃ |
| 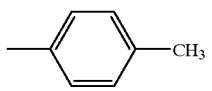 cyclohexyl | 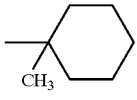—C₆H₄—CH₃ |
| 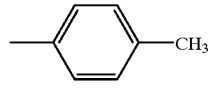 cyclopropyl-CH₃ | 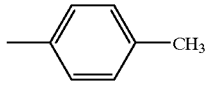—C₆H₄—CH₃ |

TABLE 6-continued

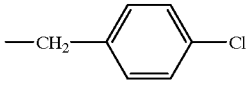 (If-α)

and

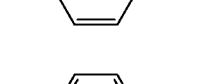 (If-β)

| R¹³ | R |
|---|---|
|  cyclopropyl-Cl | 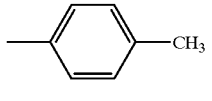—C₆H₄—CH₃ |
| 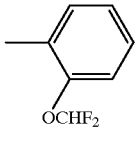 cyclopropyl-F | 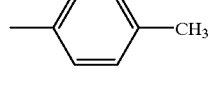—C₆H₄—CH₃ |
| 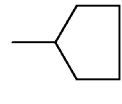 1-methylcyclohexyl | 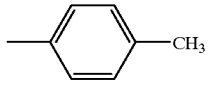—C₆H₄—CH₃ |
| —CH₂—C₆H₄—Cl | 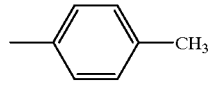—C₆H₄—CH₃ |
| 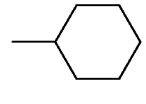 (2-OCHF₂-phenyl) | 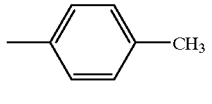—C₆H₄—CH₃ |
| —CH₂—C₆H₄—Cl (2-Cl) | 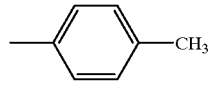—C₆H₄—CH₃ |
| —CH₂—C₆H₃(Cl)₂ (2,6-diCl) | 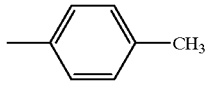—C₆H₄—CH₃ |

TABLE 6-continued
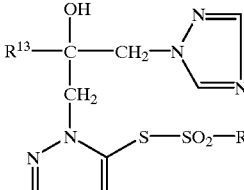 (If-α)
and
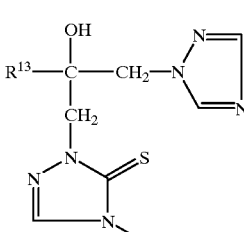 (If-β)
| R[13] | R |
|---|---|
| 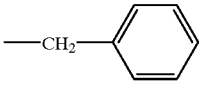 | 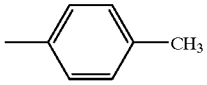 |
| 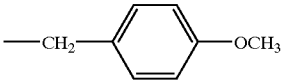 | 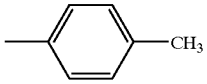 |
| 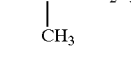 | 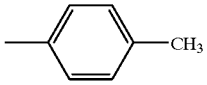 |
| 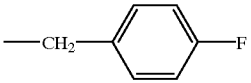 | 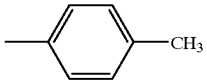 |
| 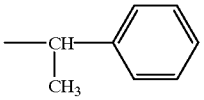 | 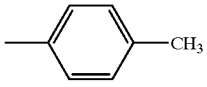 |
| 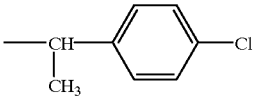 | 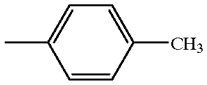 |
| 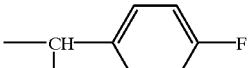 | 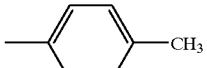 |
| 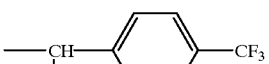 | 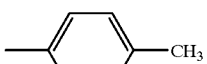 |
TABLE 6-continued
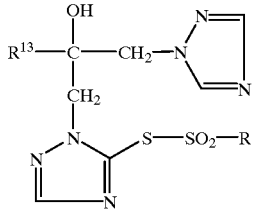 (If-α)
and
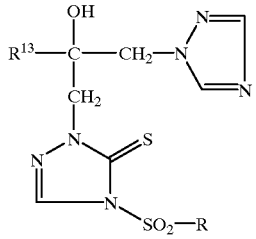 (If-β)
| R[13] | R |
|---|---|
|  | 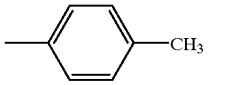 |
|  | 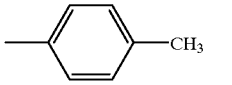 |
| 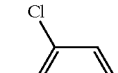 | 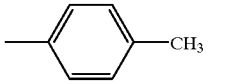 |
| 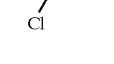 |  |
| 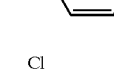 | 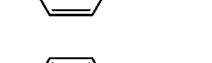 |
| 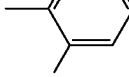 |  |
| 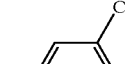 | 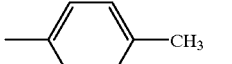 |

TABLE 6-continued (If-α)

[Structure: R¹³—C(OH)(CH₂-triazole-N-CH₂)(CH₂-N-triazole with S-SO₂-R)]

and (If-β)

[Structure: R¹³—C(OH)(CH₂-triazole)(CH₂-N-triazole-thione with N-SO₂-R)]

| R¹³ | R |
|---|---|
| 2,4-difluorophenyl | 4-methylphenyl (—CH₃) |

TABLE 7

[Structure (Ig-α): $X^4_s$-phenyl-$Y^2$-C(CH₃)₂-CH(OH)-CH(R¹⁴)-N-triazole-S-SO₂-R]

(Ig-α)

and

[Structure (Ig-β): $X^4_s$-pyridyl-$Y^2$-C(CH₃)₂-CH(OH)-CH(R¹⁴)-N-triazole-thione-N-SO₂-R]

(Ig-β)

| $X^4_s$ | $Y^2$ | $R^{14}$ | R |
|---|---|---|---|
| 4-Cl | CH₂ | H | —CH₃ |
| 4-CF₃ | CH₂ | H | —CH₃ |
| 4-OCF₃ | CH₂ | H | —CH₃ |
| 2,4-Cl₂ | CH₂ | H | —CH₃ |

TABLE 7-continued

(Ig-α)

and (Ig-β)

| $X^4_s$ | $Y^2$ | $R^{14}$ | R |
|---|---|---|---|
| 4-CH₃ | CH₂ | H | —CH₃ |
| 2-Cl | CH₂ | H | —CH₃ |
| 2-F | CH₂ | H | —CH₃ |
| 4-F | CH₂ | H | —CH₃ |
| 2-OCHF₂ | CH₂ | H | —CH₃ |
| 4-Cl | O | H | —CH₃ |
| 4-CF₃ | O | H | —CH₃ |
| 4-OCF₃ | O | H | —CH₃ |
| 2,4-Cl₂ | O | H | —CH₃ |
| 4-CH₃ | O | H | —CH₃ |
| 2-Cl | O | H | —CH₃ |
| 2-F | O | H | —CH₃ |
| 4-F | O | H | —CH₃ |
| 2-OCHF₂ | O | H | —CH₃ |
| 4-Cl | — | H | —CH₃ |
| 4-CF₃ | — | H | —CH₃ |
| 4-OCF₃ | — | H | —CH₃ |
| 2,4-Cl₂ | — | H | —CH₃ |
| 4-CH₃ | — | H | —CH₃ |
| 2-Cl | — | H | —CH₃ |
| 2-F | — | H | —CH₃ |
| 4-F | — | H | —CH₃ |
| 2-OCHF₂ | — | H | —CH₃ |
| 4-Cl | CH₂ | —CH₃ | —CH₃ |
| 4-CF₃ | CH₂ | —CH₃ | —CH₃ |
| 4-OCF₃ | CH₂ | —CH₃ | —CH₃ |
| 2,4-Cl₂ | CH₂ | —CH₃ | —CH₃ |
| 4-CH₃ | CH₂ | —CH₃ | —CH₃ |
| 2-Cl | CH₂ | —CH₃ | —CH₃ |
| 2-F | CH₂ | —CH₃ | —CH₃ |
| 4-F | CH₂ | —CH₃ | —CH₃ |
| 2-OCHF₂ | CH₂ | —CH₃ | —CH₃ |
| 4-Cl | O | —CH₃ | —CH₃ |
| 4-CF₃ | O | —CH₃ | —CH₃ |
| 2,4-Cl₂ | O | —CH₃ | —CH₃ |
| 4-OCF₃ | O | —CH₃ | —CH₃ |
| 2-F | O | —CH₃ | —CH₃ |
| 2-OCHF₂ | O | —CH₃ | —CH₃ |
| 4-Cl | — | —CH₃ | —CH₃ |
| 4-CF₃ | — | —CH₃ | —CH₃ |
| 2,4-Cl₂ | — | —CH₃ | —CH₃ |
| 4-OCF₃ | — | —CH₃ | —CH₃ |
| 2-F | — | —CH₃ | —CH₃ |
| 2-OCHF₂ | — | —CH₃ | —CH₃ |
| 4-Cl | CH₂ | C₄H₉-n | —CH₃ |
| 2,4-Cl₂ | CH₂ | —CH(CH₃)₂ | —CH₃ |
| 4-OCF₃ | CH₂ | —C(CH₃)₃ | —CH₃ |
| 4-Cl | CH₂ | ▷ | —CH₃ |

TABLE 7-continued $$\text{(Ig-}\alpha\text{)}$$

[Structure showing phenyl ring with $X_s^4$ substituent connected via $Y^2$ to C(CH$_3$)$_2$-CH(OH)-CH(R$^{14}$)-N of a 1,2,4-triazole ring bearing S-SO$_2$-R at the 5-position]

and $$\text{(Ig-}\beta\text{)}$$

[Structure showing phenyl ring with $X_s^4$ substituent connected via $Y^2$ to C(CH$_3$)$_2$-CH(OH)-CH(R$^{14}$)-N of a 1,2,4-triazole-3-thione ring with SO$_2$-R on the 4-N]

| $X_s^4$ | $Y^2$ | $R^{14}$ | R |
|---|---|---|---|
| 4-Cl | CH$_2$ | cyclopropyl-Cl | —CH$_3$ |
| 4-Cl | CH$_2$ | cyclopentyl | —CH$_3$ |
| 4-Cl | CH$_2$ | cyclohexyl | —CH$_3$ |
| 2,4,6-Cl$_3$ | CH$_2$ | —CH$_3$ | —CH$_3$ |
| 4-phenyl- | CH$_2$ | —CH$_3$ | —CH$_3$ |
| 4-O-phenyl- | CH$_2$ | —CH$_3$ | —CH$_3$ |
| 4-Cl | CH$_2$ | H | 4-methylphenyl |
| 4-CF$_3$ | CH$_2$ | H | 4-methylphenyl |
| 4-OCF$_3$ | CH$_2$ | H | 4-methylphenyl |
| 2,4-Cl$_2$ | CH$_2$ | H | 4-methylphenyl |

TABLE 7-continued
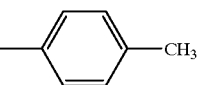
(Ig-α)
and
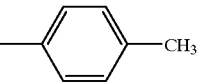
(Ig-β)
| $X^4_s$ | $Y^2$ | $R^{14}$ | R |
|---|---|---|---|
| 4-CH$_3$ | CH$_2$ | H | 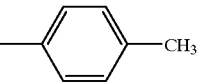 |
| 2-Cl | CH$_2$ | H | 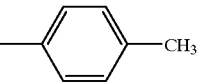 |
| 2-F | CH$_2$ | H | 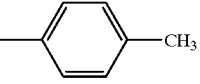 |
| 4-F | CH$_2$ | H | 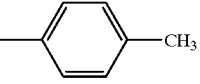 |
| 2-OCHF$_2$ | CH$_2$ | H | 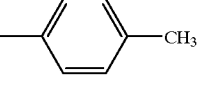 |
| 4-Cl | O | H | 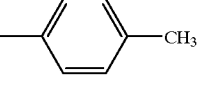 |
| 4-CF$_3$ | O | H | 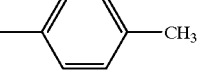 |
| 4-OCF$_3$ | O | H | 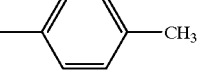 |
| 2,4-Cl$_2$ | O | H | 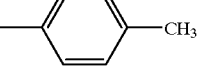 |

TABLE 7-continued
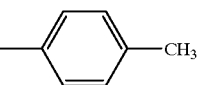
(Ig-α)
and
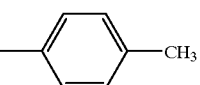
(Ig-β)
| $X^4_s$ | $Y^2$ | $R^{14}$ | R |
|---|---|---|---|
| 4-CH$_3$ | O | H | 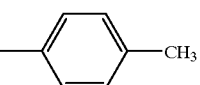 |
| 2-Cl | O | H | 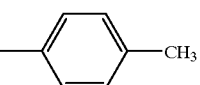 |
| 2-F | O | H | 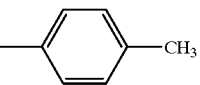 |
| 4-F | O | H | 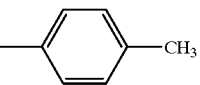 |
| 2-OCHF$_2$ | O | H | 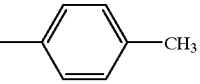 |
| 4-Cl | — | H | 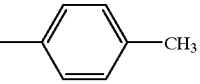 |
| 4-CF$_3$ | — | H | 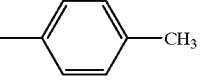 |
| 4-OCF$_3$ | — | H | 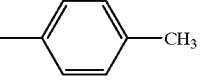 |
| 2,4-Cl$_2$ | — | H | 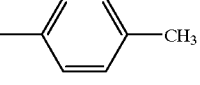 |

TABLE 7-continued
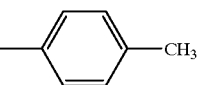
(Ig-α)
and
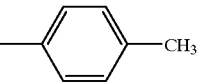
(Ig-β)
| $X^4_s$ | $Y^2$ | $R^{14}$ | R |
|---|---|---|---|
| 4-CH₃ | — | H | 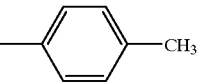 |
| 2-Cl | — | H | 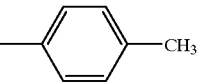 |
| 2-F | — | H | 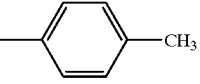 |
| 4-F | — | H | 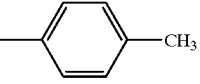 |
| 2-OCHF₂ | — | H | 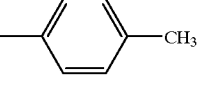 |
| 4-Cl | CH₂ | —CH₃ | 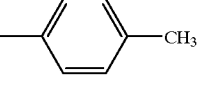 |
| 4-CF₃ | CH₂ | —CH₃ | 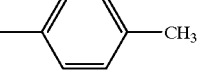 |
| 4-OCF₃ | CH₂ | —CH₃ | 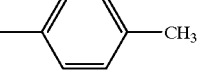 |
| 2,4-Cl₂ | CH₂ | —CH₃ | 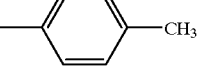 |

TABLE 7-continued
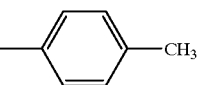
(Ig-α)
and
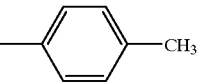
(Ig-β)
| $X^4{}_s$ | $Y^2$ | $R^{14}$ | R |
|---|---|---|---|
| 4-CH$_3$ | CH$_2$ | —CH$_3$ | 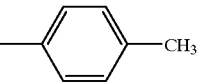 |
| 2-Cl | CH$_2$ | —CH$_3$ | 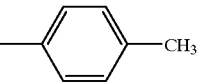 |
| 2-F | CH$_2$ | —CH$_3$ | 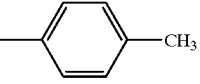 |
| 4-F | CH$_2$ | —CH$_3$ | 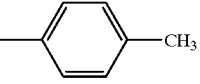 |
| 2-OCHF$_2$ | CH$_2$ | —CH$_3$ | 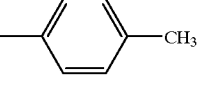 |
| 4-Cl | O | —CH$_3$ | 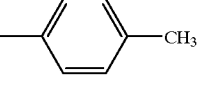 |
| 4-CF$_3$ | O | —CH$_3$ | 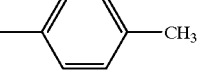 |
| 2,4-Cl$_2$ | O | —CH$_3$ | 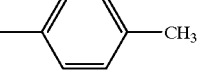 |
| 4-OCF$_3$ | O | —CH$_3$ | 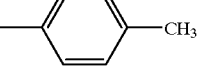 |

TABLE 7-continued
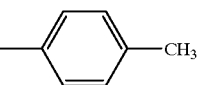
(Ig-α)
and
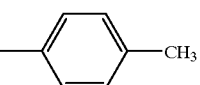
(Ig-β)
| $X^4_s$ | $Y^2$ | $R^{14}$ | R |
|---|---|---|---|
| 2-F | O | —CH$_3$ | 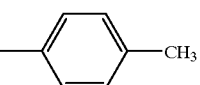 |
| 2-OCHF$_2$ | O | —CH$_3$ | 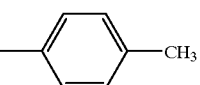 |
| 4-Cl | — | —CH$_3$ | 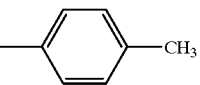 |
| 2,4-Cl$_2$ | — | —CH$_3$ | 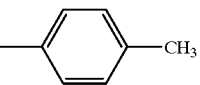 |
| 4-OCF$_3$ | — | —CH$_3$ | 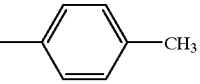 |
| 2-F | — | —CH$_3$ | 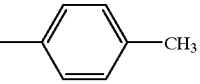 |
| 2-OCHF$_2$ | — | —CH$_3$ | 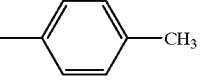 |
| 4-Cl | CH$_2$ | —C$_4$H$_9$-n | 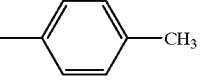 |
| 2,4-Cl$_2$ | CH$_2$ | —CH(CH$_3$)$_2$ | 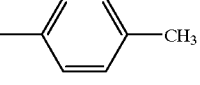 |

TABLE 7-continued
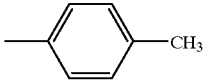
(Ig-α)
and
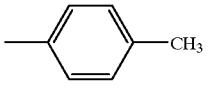
(Ig-β)
| $X^4_s$ | $Y^2$ | $R^{14}$ | R |
|---|---|---|---|
| 4-OCF₃ | CH₂ | —C(CH₃)₃ |  |
| 4-Cl | CH₂ | 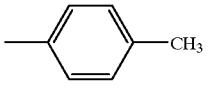 | 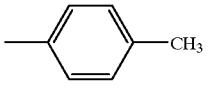 |
| 4-Cl | CH₂ | —Cl | 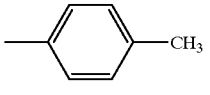 |
| 4-Cl | CH₂ | 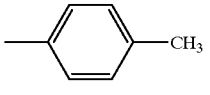 |  |
| 4-Cl | CH₂ | 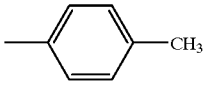 | 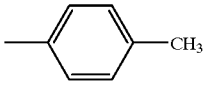 |
| 2,4,6-Cl₃ | CH₂ | —CH₃ |  |
| 4-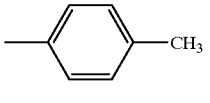 | CH₂ | —CH₃ | 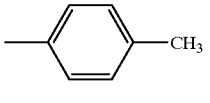 |
| 4-O-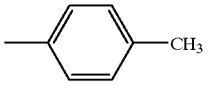 | CH₂ | —CH₃ | 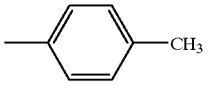 |
| 4-OCF₃ | CH₂ | —CH₃ | 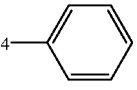 |

TABLE 8

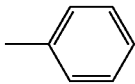

(Ih-α)
and

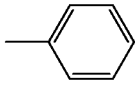

(Ih-β)

| $X^5_t$ | $R^{15}$ | R | $Y^3$ |
|---|---|---|---|
| 2,4-Cl$_2$ | 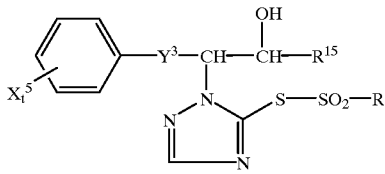 | —CH$_3$ | O |
| 4-Cl | 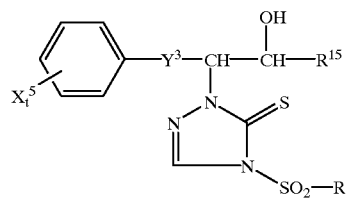 | —CH$_3$ | O |
| 4-Br | —C(CH$_3$)$_3$ | —CH$_3$ | O |
| — | —C(CH$_3$)$_3$ | —CH$_3$ | O |
| 4-C(CH$_3$)$_3$ | —C(CH$_3$)$_3$ | —CH$_3$ | O |
| 2-Cl | —C(CH$_3$)$_3$ | —CH$_3$ | O |
| 3-Cl | —C(CH$_3$)$_3$ | —CH$_3$ | O |
| 4-F | —C(CH$_3$)$_3$ | —CH$_3$ | O |
| 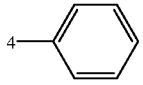 | —C(CH$_3$)$_3$ | —CH$_3$ | O |
| 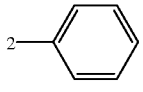 | —C(CH$_3$)$_3$ | —CH$_3$ | O |
| 2,4-Cl$_2$ | —C(CH$_3$)$_3$ | —CH$_3$ | O |
| 2-CH$_3$, 4-Cl | —C(CH$_3$)$_3$ | —CH$_3$ | O |
| 3,4-(CH$_3$)$_2$ | —C(CH$_3$)$_3$ | —CH$_3$ | O |
| 2,4,5-Cl$_3$ | —C(CH$_3$)$_3$ | —CH$_3$ | O |
| 4-Cl | —CH$_3$ | —CH$_3$ | O |
| 4-Cl | 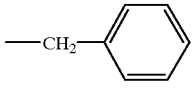 | —CH$_3$ | O |
| 4-CF$_3$ | —C(CH$_3$)$_3$ | —CH$_3$ | O |
| 4-OCF$_3$ | —C(CH$_3$)$_3$ | —CH$_3$ | O |
| 2-OCHF$_2$ | —C(CH$_3$)$_3$ | —CH$_3$ | O |
| 4-OCH$_3$ | —C(CH$_3$)$_3$ | —CH$_3$ | O |
| 2,4-Cl$_2$ | 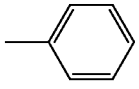 | 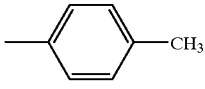 | O |

TABLE 8-continued (Ih-α)
and (Ih-β)

| $X^5_t$ | $R^{15}$ | R | $Y^3$ |
|---|---|---|---|
| 4-Cl | —C₆H₅ | 4-CH₃-C₆H₄— | O |
| 4-Br | —C(CH₃)₃ | 4-CH₃-C₆H₄— | O |
| — | —C(CH₃)₃ | 4-CH₃-C₆H₄— | O |
| 4-C(CH₃)₃ | —C(CH₃)₃ | 4-CH₃-C₆H₄— | O |
| 2-Cl | —C(CH₃)₃ | 4-CH₃-C₆H₄— | O |
| 3-Cl | —C(CH₃)₃ | 4-CH₃-C₆H₄— | O |
| 4-F | —C(CH₃)₃ | 4-CH₃-C₆H₄— | O |
| 4-C₆H₅ | —C(CH₃)₃ | 4-CH₃-C₆H₄— | O |
| 2-C₆H₅ | —C(CH₃)₃ | 4-CH₃-C₆H₄— | O |

TABLE 8-continued
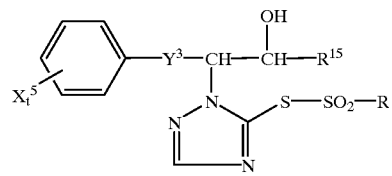
(Ih-α)
and
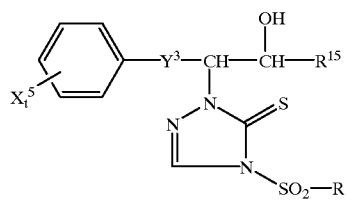
(Ih-β)
| $X^5_t$ | $R^{15}$ | R | $Y^3$ |
|---|---|---|---|
| 2,4-Cl$_2$ | —C(CH$_3$)$_3$ | ⏤⟨C$_6$H$_4$⟩—CH$_3$ | O |
| 2-CH$_3$, 4-Cl | —C(CH$_3$)$_3$ | ⏤⟨C$_6$H$_4$⟩—CH$_3$ | O |
| 3,4-(CH$_3$)$_2$ | —C(CH$_3$)$_3$ | ⏤⟨C$_6$H$_4$⟩—CH$_3$ | O |
| 2,4,5-Cl$_3$ | —C(CH$_3$)$_3$ | ⏤⟨C$_6$H$_4$⟩—CH$_3$ | O |
| 4-Cl | —CH$_3$ | ⏤⟨C$_6$H$_4$⟩—CH$_3$ | O |
| 4-Cl | —CH$_2$—⟨pyridyl⟩ | ⏤⟨C$_6$H$_4$⟩—CH$_3$ | O |
| 4-CF$_3$ | —C(CH$_3$)$_3$ | ⏤⟨C$_6$H$_4$⟩—CH$_3$ | O |
| 4-OCF$_3$ | —C(CH$_3$)$_3$ | ⏤⟨C$_6$H$_4$⟩—CH$_3$ | O |
| 2-OCHF$_2$ | —C(CH$_3$)$_3$ | ⏤⟨C$_6$H$_4$⟩—CH$_3$ | O |

TABLE 8-continued
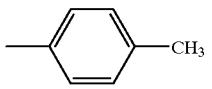
(Ih-α)
and
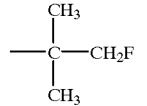
(Ih-β)
| $X^5_t$ | $R^{15}$ | R | $Y^3$ |
|---|---|---|---|
| 4-OCH₃ | —C(CH₃)₃ | 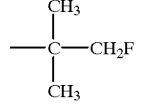 | O |
| 4-Cl | 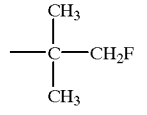 | —CH₃ | O |
| 4-Cl | 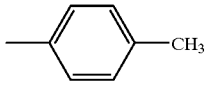 | —CH₃ | O |
| 4-Cl | 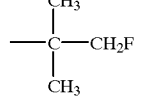 | 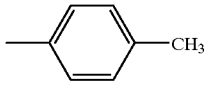 | O |
| 4-Cl | 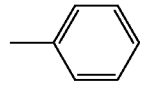 | 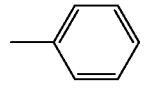 | O |
| 2,4-Cl₂ |  | —CH₃ | CH₂ |
| 4-Cl |  | —CH₃ | CH₂ |
| 4-Br | —C(CH₃)₃ | —CH₃ | CH₂ |
| — | —C(CH₃)₃ | —CH₃ | CH₂ |
| 4-C(CH₃)₃ | —C(CH₃)₃ | —CH₃ | CH₂ |
| 2-Cl | —C(CH₃)₃ | —CH₃ | CH₂ |
| 3-Cl | —C(CH₃)₃ | —CH₃ | CH₂ |
| 4-F | —C(CH₃)₃ | —CH₃ | CH₂ |

TABLE 8-continued
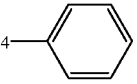
(Ih-α)
and
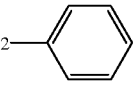
(Ih-β)
| $X^5_t$ | $R^{15}$ | R | $Y^3$ |
|---|---|---|---|
| 4-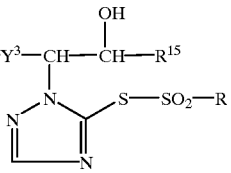 | —C(CH$_3$)$_3$ | —CH$_3$ | CH$_2$ |
| 2-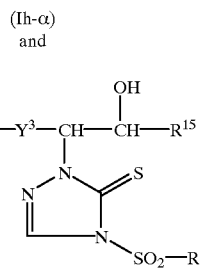 | —C(CH$_3$)$_3$ | —CH$_3$ | CH$_2$ |
| 2,4-Cl$_2$ | —C(CH$_3$)$_3$ | —CH$_3$ | CH$_2$ |
| 2-CH$_3$, 4-Cl | —C(CH$_3$)$_3$ | —CH$_3$ | CH$_2$ |
| 3,4-(CH$_3$)$_2$ | —C(CH$_3$)$_3$ | —CH$_3$ | CH$_2$ |
| 2,4,5-Cl$_3$ | —C(CH$_3$)$_3$ | —CH$_3$ | CH$_2$ |
| 4-Cl | —C(CH$_3$)$_3$ | —CH$_3$ | CH$_2$ |
| 4-Cl | 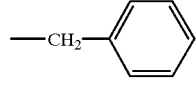 | —CH$_3$ | CH$_2$ |
| 4-CF$_3$ | —C(CH$_3$)$_3$ | —CH$_3$ | CH$_2$ |
| 4-OCF$_3$ | —C(CH$_3$)$_3$ | —CH$_3$ | CH$_2$ |
| 2-OCHF$_2$ | —C(CH$_3$)$_3$ | —CH$_3$ | CH$_2$ |
| 4-OCH$_3$ | —C(CH$_3$)$_3$ | —CH$_3$ | CH$_2$ |
| 2,4-Cl$_2$ | 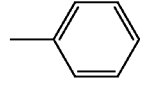 | 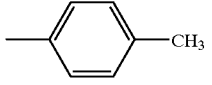 | CH$_2$ |
| 4-Cl | 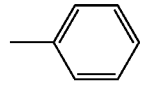 | 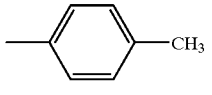 | CH$_2$ |
| 4-Br | —C(CH$_3$)$_3$ | 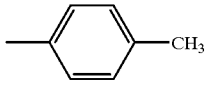 | CH$_2$ |
| — | —C(CH$_3$)$_3$ | 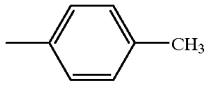 | CH$_2$ |

TABLE 8-continued
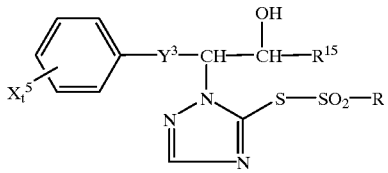
(Ih-α)
and
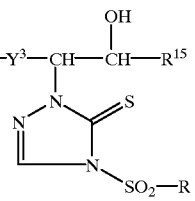
(Ih-β)
| $X^5_t$ | $R^{15}$ | R | $Y^3$ |
|---|---|---|---|
| 4-C(CH$_3$)$_3$ | —C(CH$_3$)$_3$ | 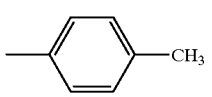 | CH$_2$ |
| 2-Cl | —C(CH$_3$)$_3$ | 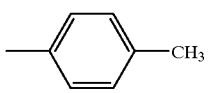 | CH$_2$ |
| 3-Cl | —C(CH$_3$)$_3$ | 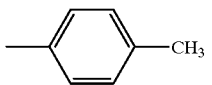 | CH$_2$ |
| 4-F | —C(CH$_3$)$_3$ | 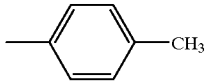 | CH$_2$ |
| 4-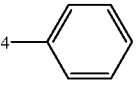 | —C(CH$_3$)$_3$ | 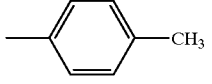 | CH$_2$ |
| 2-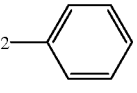 | —C(CH$_3$)$_3$ | 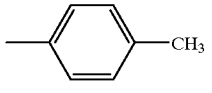 | CH$_2$ |
| 2,4-Cl$_2$ | —C(CH$_3$)$_3$ | 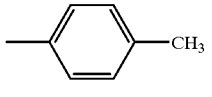 | CH$_2$ |
| 2-CH$_3$, 4-Cl | —C(CH$_3$)$_3$ | 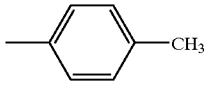 | CH$_2$ |
| 3,4-(CH$_3$)$_2$ | —C(CH$_3$)$_3$ | 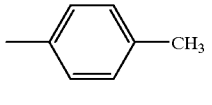 | CH$_2$ |

TABLE 8-continued
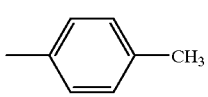
(Ih-α)
and
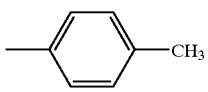
(Ih-β)
| $X^5_t$ | $R^{15}$ | R | $Y^3$ |
|---|---|---|---|
| 2,4,5-Cl$_3$ | —C(CH$_3$)$_3$ | | CH$_2$ |
| 4-Cl | —CH$_3$ | | CH$_2$ |
| 4-Cl | —CH$_2$—C$_6$H$_5$ | | CH$_2$ |
| 4-CF$_3$ | —C(CH$_3$)$_3$ | | CH$_2$ |
| 4-OCF$_3$ | —C(CH$_3$)$_3$ | | CH$_2$ |
| 2-OCHF$_2$ | —C(CH$_3$)$_3$ | | CH$_2$ |
| 4-OCH$_3$ | —C(CH$_3$)$_3$ | | CH$_2$ |
| 4-Cl | —C(CH$_3$)$_2$CH$_2$F | —CH$_3$ | CH$_2$ |
| 4-Cl | —C(CH$_3$)$_2$CH$_2$F | —CH$_3$ | CH$_2$ |

TABLE 8-continued
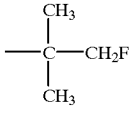
(Ih-α)
and
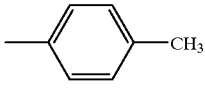
(Ih-β)
| $X_t^5$ | $R^{15}$ | R | $Y^3$ |
|---|---|---|---|
| 4-Cl | 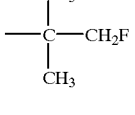 | 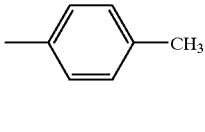 | $CH_2$ |
| 4-Cl | 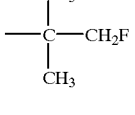 | 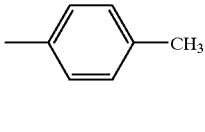 | $CH_2$ |
| 4-Cl | —C(CH$_3$)$_3$ | —CH$_3$ | O |
| 4-Cl | —C(CH$_3$)$_3$ | 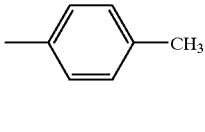 | O |
TABLE 9
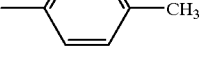
(Ii-α)         and         (Ii-β)
| $X_u^6$ | A | R |
|---|---|---|
| 2,4-Cl$_2$ | —(CH$_2$)$_3$— | —CH$_3$ |
| 2,4-Cl$_2$ | —(CH$_2$)$_2$— | —CH$_3$ |
| 4-Cl | 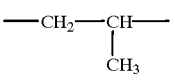 | —CH$_3$ |
| 4-CF$_3$ | 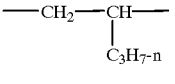 | —CH$_3$ |

TABLE 9-continued
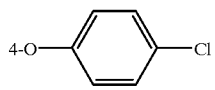
| $X_u^6$ | A | R |
|---|---|---|
| 2-Cl, 4-O-(4-chlorophenyl) | —CH₂—CH₂— | —CH₃ |
| 2-Cl, 4-O-(4-chlorophenyl) | —CH₂—CH(C₂H₅)— | —CH₃ |
| 4-F | —CH₂—CH(C₃H₇-n)— | —CH₃ |
| 4-OCF₃ | —CH₂—CH(C₃H₇-n)— | —CH₃ |
| 2,4-F₂ | —CH₂—CH(C₃H₇-n)— | —CH₃ |
| 2-OCHF₂ | —CH₂—CH(C₃H₇-n)— | —CH₃ |
| 2-Cl, 4-O-(4-chlorophenyl) | —(CH₂)₃— | —CH₃ |
| 2,4,6-Cl₃ | —CH₂—CH(C₃H₇-n)— | —CH₃ |
| — | —CH₂—CH(C₃H₇-n)— | —CH₃ |
| 2,4-F₂ | —CH₂—CH(CH₃)— | —CH₃ |
| 2-Cl, 4-O-(4-chlorophenyl) | —CH₂—CH(CH₃)— | —CH₃ |
| 2,4-Cl₂ | —CH(CH₃)—CH(CH₃)— | —CH₃ |

TABLE 9-continued

Structures (Ii-α) and (Ii-β)

| $X_u^6$ | A | R |
|---|---|---|
| 2-Cl, 4-O-C$_6$H$_4$-Cl | —CH(CH$_3$)—CH(CH$_3$)— | —CH$_3$ |
| 2,4-Cl$_2$ | —CH$_2$—CHF— | —CH$_3$ |
| 2-Cl, 4-O-C$_6$H$_4$-Cl | —CH$_2$—CH(C$_4$H$_9$-n)— | —CH$_3$ |
| 2,4-Cl$_2$ | —CH$_2$—CH(C$_2$H$_5$)— | —CH$_3$ |
| 2,4-Cl$_2$ | —(CH$_2$)$_3$— | —C$_6$H$_4$-CH$_3$ |
| 2,4-Cl$_2$ | —(CH$_2$)$_2$— | —C$_6$H$_4$-CH$_3$ |
| 4-Cl | —CH$_2$—CH(CH$_3$)— | —C$_6$H$_4$-CH$_3$ |
| 4-CF$_3$ | —CH$_2$—CH(C$_3$H$_7$-n)— | —C$_6$H$_4$-CH$_3$ |
| 2-Cl, 4-O-C$_6$H$_4$-Cl | —CH$_2$—CH$_2$— | —C$_6$H$_4$-CH$_3$ |
| 2-Cl, 4-O-C$_6$H$_4$-Cl | —CH$_2$—CH(C$_2$H$_5$)— | —C$_6$H$_4$-CH$_3$ |
| 4-F | —CH$_2$—CH(C$_3$H$_7$-n)— | —C$_6$H$_4$-CH$_3$ |

TABLE 9-continued

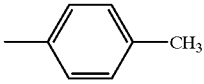

| $X_u^6$ | A | R |
|---|---|---|
| 4-OCF$_3$ | —CH$_2$—CH(C$_3$H$_7$-n)— | -C$_6$H$_4$-CH$_3$ (p) |
| 2,4-F$_2$ | —CH$_2$—CH(C$_3$H$_7$-n)— | -C$_6$H$_4$-CH$_3$ (p) |
| 2-OCHF$_2$ | —CH$_2$—CH(C$_3$H$_7$-n)— | -C$_6$H$_4$-CH$_3$ (p) |
| 2-Cl, 4-O-C$_6$H$_4$-Cl | —(CH$_2$)$_3$— | -C$_6$H$_4$-CH$_3$ (p) |
| 2,4,6-Cl$_3$ | —CH$_2$—CH(C$_3$H$_7$-n)— | -C$_6$H$_4$-CH$_3$ (p) |
| — | —CH$_2$—CH(C$_3$H$_7$-n)— | -C$_6$H$_4$-CH$_3$ (p) |
| 2,4-F$_2$ | —CH$_2$—CH(CH$_3$)— | -C$_6$H$_4$-CH$_3$ (p) |
| 2-Cl, 4-O-C$_6$H$_4$-Cl | —CH$_2$—CH(CH$_3$)— | -C$_6$H$_4$-CH$_3$ (p) |
| 2,4-Cl$_2$ | —CH(CH$_3$)—CH(CH$_3$)— | -C$_6$H$_4$-CH$_3$ (p) |
| 2-Cl, 4-O-C$_6$H$_4$-Cl | —CH(CH$_3$)—CH(CH$_3$)— | -C$_6$H$_4$-CH$_3$ (p) |
| 2,4-Cl$_2$ | —CH$_2$—CH(F)— | -C$_6$H$_4$-CH$_3$ (p) |

TABLE 9-continued (Ii-α) and (Ii-β)

| $X_u^6$ | A | R |
|---|---|---|
| 2-Cl, 4-O-(4-chlorophenyl) | —CH$_2$—CH(C$_4$H$_9$-n)— | 4-CH$_3$-phenyl |
| 2,4-Cl$_2$ | —CH$_2$—CH(C$_2$H$_5$)— | 4-CH$_3$-phenyl |
| 2,4-Cl$_2$ | —CH$_2$—CH(C$_3$H$_7$-n)— | —CH$_3$ |
| 2,4-Cl$_2$ | —CH$_2$—CH(C$_3$H$_7$-n)— | 4-CH$_3$-phenyl |

TABLE 10

(Ik-α) and (Ik-β)

| $X_v^7$ | $R^{16}$ | R |
|---|---|---|
| 2,4-Cl$_2$ | —CH$_3$ | —CH$_3$ |
| 2,4-Cl$_2$ | —C$_2$H$_5$ | —CH$_3$ |
| 2,4-Cl$_2$ | —CH(CH$_3$)$_2$ | —CH$_3$ |
| 4-Cl | —C$_3$H$_7$-n | —CH$_3$ |
| 2,4-Cl$_2$ | —C$_4$H$_9$-n | —CH$_3$ |
| 2,4-Cl$_2$ | —CH(CH$_3$)—C$_2$H$_5$ | —CH$_3$ |
| 2,4-Cl$_2$ | —C(CH$_3$)$_3$ | —CH$_3$ |
| 2-Cl | —C$_3$H$_7$-n | —CH$_3$ |
| 2-OCF$_3$ | —C$_3$H$_7$-n | —CH$_3$ |
| 4-CF$_3$ | —C$_3$H$_7$-n | —CH$_3$ |
| 4-CH$_3$ | —C$_3$H$_7$-n | —CH$_3$ |
| 2,4,6-Cl$_3$ | —C$_3$H$_7$-n | —CH$_3$ |
| 2,4-Cl$_2$ | (chlorocyclopropyl) | —CH$_3$ |
| 4-F | —C$_3$H$_7$-n | —CH$_3$ |

TABLE 10-continued

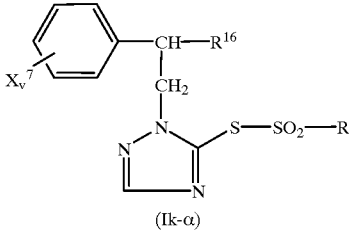

| $X_v^7$ | $R^{16}$ | R |
|---|---|---|
| 2,4-Cl$_2$ | cyclopropyl-F | —CH$_3$ |
| 2,4-Cl$_2$ | cyclopropyl | —CH$_3$ |
| 2,4-Cl$_2$ | cyclopentyl | —CH$_3$ |
| 2,4-Cl$_2$ | cyclohexyl | —CH$_3$ |
| 2,4-Cl$_2$ | —CH$_2$—cyclohexyl | —CH$_3$ |
| 2,4-Cl$_2$ | —CH(CH$_3$)-cyclopropyl | —CH$_3$ |
| 2,4-Cl$_2$ | —C$_6$H$_4$-Cl (4-Cl-phenyl) | —CH$_3$ |
| 2,4-Cl$_2$ | —C$_6$H$_4$-F (4-F-phenyl) | —CH$_3$ |
| 2,4-Cl$_2$ | —CH$_2$—C$_6$H$_4$-Cl | —CH$_3$ |
| 2,4-Cl$_2$ | —CH$_2$—C$_6$H$_4$-F | —CH$_3$ |
| 2,4-Cl$_2$ | —CH$_2$—O—CF$_2$—CHF$_2$ | —CH$_3$ |
| 2,4-Cl$_2$ | —CH$_2$—O—CF$_2$—CH$_3$ | —CH$_3$ |
| 4-Cl | —CH$_2$—O—CF$_2$—CHF$_2$ | —CH$_3$ |
| 2,4-Cl$_2$ | —CH$_2$—O—CF$_3$ | —CH$_3$ |
| 4-F | —CH$_2$—O—CF$_2$—CHF$_2$ | —CH$_3$ |
| 2-Cl | —CH$_2$—O—CF$_2$—CHF$_2$ | —CH$_3$ |
| 2,4-Cl$_2$ | —CH$_3$ | —C$_6$H$_4$—CH$_3$ |

TABLE 10-continued
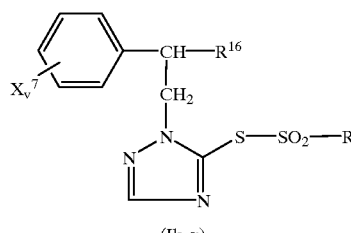
(Ik-α) and (Ik-β)
| $X_v^7$ | $R^{16}$ | R |
|---|---|---|
| 2,4-Cl$_2$ | —C$_2$H$_5$ | 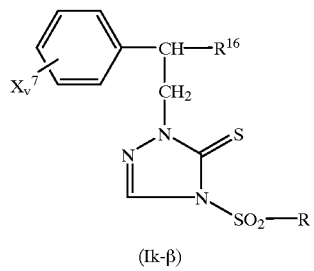 —CH$_3$ |
| 2,4-Cl$_2$ | —CH(CH$_3$)$_2$ |  —CH$_3$ |
| 4-Cl | —C$_3$H$_7$-n | 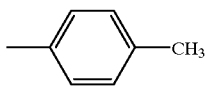 —CH$_3$ |
| 2,4-Cl$_2$ | —C$_4$H$_9$-n | 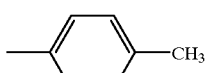 —CH$_3$ |
| 2,4-Cl$_2$ | —CH(CH$_3$)—C$_2$H$_5$ | 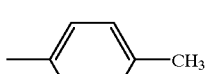 —CH$_3$ |
| 2,4-Cl$_2$ | —C(CH$_3$)$_3$ | 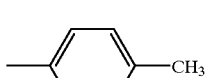 —CH$_3$ |
| 2-Cl | —C$_3$H$_7$-n | 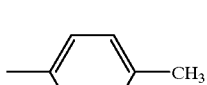 —CH$_3$ |
| 2-OCF$_3$ | —C$_3$H$_7$-n | 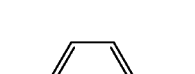 —CH$_3$ |
| 4-CF$_3$ | —C$_3$H$_7$-n | 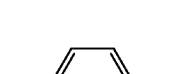 —CH$_3$ |
| 4-CH$_3$ | —C$_3$H$_7$-n | 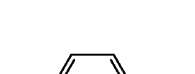 —CH$_3$ |

TABLE 10-continued
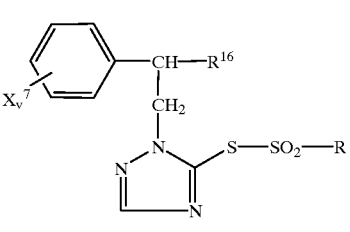
| $X_v^7$ | $R^{16}$ | R |
|---|---|---|
| 2,4,6-Cl$_3$ | —C$_3$H$_7$-n | 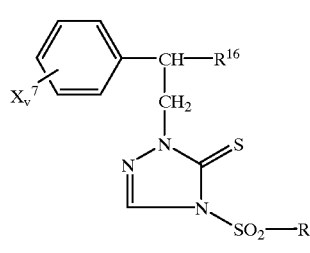 |
| 2,4-Cl$_2$ | 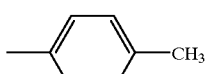 |  |
| 4-F | —C$_3$H$_7$-n | 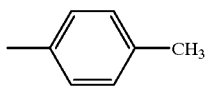 |
| 2,4-Cl$_2$ |  |  |
| 2,4-Cl$_2$ | 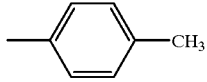 |  |
| 2,4-Cl$_2$ |  | 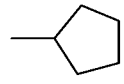 |
| 2,4-Cl$_2$ |  | 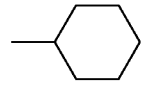 |
| 2,4-Cl$_2$ | 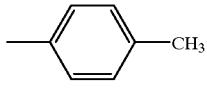 | 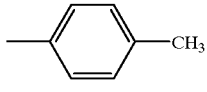 |
| 2,4-Cl$_2$ | 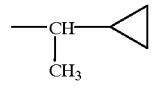 | 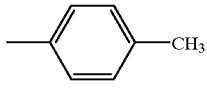 |
| 2,4-Cl$_2$ | 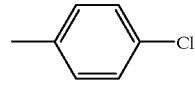 | 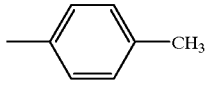 |
| 2,4-Cl$_2$ | 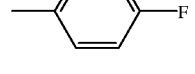 | 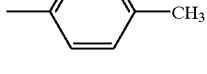 |

TABLE 10-continued
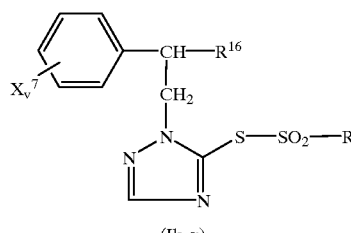
| $X_v^7$ | $R^{16}$ | R |
|---|---|---|
| 2,4-Cl$_2$ | —CH$_2$—⬡—Cl | —⬡—CH$_3$ |
| 2,4-Cl$_2$ | —CH$_2$—⬡—F | —⬡—CH$_3$ |
| 2,4-Cl$_2$ | —CH$_2$—O—CF$_2$—CHF$_2$ | —⬡—CH$_3$ |
| 2,4-Cl$_2$ | —CH$_2$—O—CF$_2$—CH$_3$ | —⬡—CH$_3$ |
| 4-Cl | —CH$_2$—O—CF$_2$—CHF$_2$ | —⬡—CH$_3$ |
| 2,4-Cl$_2$ | —CH$_2$—O—CF$_3$ | —⬡—CH$_3$ |
| 4-F | —CH$_2$—O—CF$_2$—CHF$_2$ | —⬡—CH$_3$ |
| 2-Cl | —CH$_2$—O—CF$_2$—CHF$_2$ | —⬡—CH$_3$ |
| 2,4-Cl$_2$ | —CH$_2$—CF$_3$ | —CH$_3$ |
| 2,4-Cl$_2$ | —CF$_2$—CF$_3$ | —CH$_3$ |
| 2,4-Cl$_2$ | —C$_3$H$_7$-n | —CH$_3$ |
| 2,4-Cl$_2$ | —C$_3$H$_7$-n | —⬡—CH$_3$ |

TABLE 11

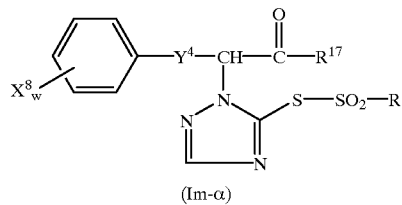

(Im-α)

and

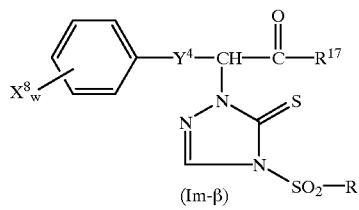

(Im-β)

| $X^8_w$ | $R^{17}$ | R | $Y^4$ |
|---|---|---|---|
| 2,4-Cl$_2$ | ![phenyl] | —CH$_3$ | O |
| 4-Cl | ![phenyl] | —CH$_3$ | O |
| 4-Br | —C(CH$_3$)$_3$ | —CH$_3$ | O |
| — | —C(CH$_3$)$_3$ | —CH$_3$ | O |
| 4-C(CH$_3$)$_3$ | —C(CH$_3$)$_3$ | —CH$_3$ | O |
| 2-Cl | —C(CH$_3$)$_3$ | —CH$_3$ | O |
| 3-Cl | —C(CH$_3$)$_3$ | —CH$_3$ | O |
| 4-F | —C(CH$_3$)$_3$ | —CH$_3$ | O |
| 4-phenyl | —C(CH$_3$)$_3$ | —CH$_3$ | O |
| 2-phenyl | —C(CH$_3$)$_3$ | —CH$_3$ | O |
| 2,4-Cl$_2$ | —C(CH$_3$)$_3$ | —CH$_3$ | O |
| 2-CH$_3$, 4-Cl | —C(CH$_3$)$_3$ | —CH$_3$ | O |
| 3,4-(CH$_3$)$_2$ | —C(CH$_3$)$_3$ | —CH$_3$ | O |
| 2,4,5-Cl$_3$ | —C(CH$_3$)$_3$ | —CH$_3$ | O |
| 4-Cl | —CH$_3$ | —CH$_3$ | O |
| 4-Cl | —CH$_2$-phenyl | —CH$_3$ | O |
| 4-CF$_3$ | —C(CH$_3$)$_3$ | —CH$_3$ | O |
| 4-OCF$_3$ | —C(CH$_3$)$_3$ | —CH$_3$ | O |
| 2-OCHF$_2$ | —C(CH$_3$)$_3$ | —CH$_3$ | O |
| 4-OCH$_3$ | —C(CH$_3$)$_3$ | —CH$_3$ | O |

TABLE 11-continued
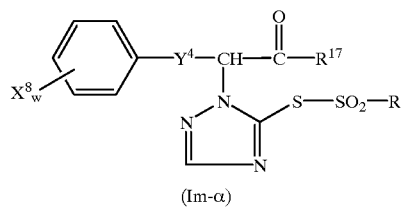
(Im-α)
and
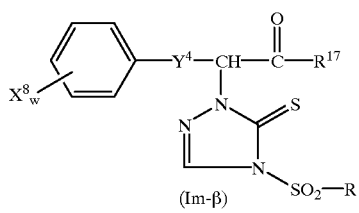
(Im-β)
| $X^8_w$ | $R^{17}$ | R | $Y^4$ |
|---|---|---|---|
| 2,4-Cl$_2$ | —C$_6$H$_5$ | 4-CH$_3$-C$_6$H$_4$ | O |
| 4-Cl | —C$_6$H$_5$ | 4-CH$_3$-C$_6$H$_4$ | O |
| 4-Br | —C(CH$_3$)$_3$ | 4-CH$_3$-C$_6$H$_4$ | O |
| — | —C(CH$_3$)$_3$ | 4-CH$_3$-C$_6$H$_4$ | O |
| 4-C(CH$_3$)$_3$ | —C(CH$_3$)$_3$ | 4-CH$_3$-C$_6$H$_4$ | O |
| 2-Cl | —C(CH$_3$)$_3$ | 4-CH$_3$-C$_6$H$_4$ | O |
| 3-Cl | —C(CH$_3$)$_3$ | 4-CH$_3$-C$_6$H$_4$ | O |
| 4-F | —C(CH$_3$)$_3$ | 4-CH$_3$-C$_6$H$_4$ | O |

TABLE 11-continued
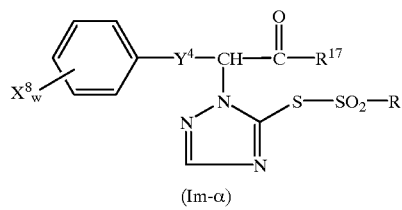
(Im-α)
and
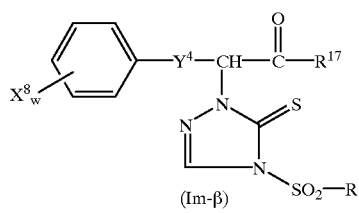
(Im-β)
| $X^8_w$ | $R^{17}$ | R | $Y^4$ |
|---|---|---|---|
| 4-[phenyl] | —C(CH₃)₃ | [4-CH₃-phenyl] | O |
| 2-[phenyl] | —C(CH₃)₃ | [4-CH₃-phenyl] | O |
| 2,4-Cl₂ | —C(CH₃)₃ | [4-CH₃-phenyl] | O |
| 2-CH₃, 4-Cl | —C(CH₃)₃ | [4-CH₃-phenyl] | O |
| 3,4-(CH₃)₂ | —C(CH₃)₃ | [4-CH₃-phenyl] | O |
| 2,4,5-Cl₃ | —C(CH₃)₃ | [4-CH₃-phenyl] | O |
| 4-Cl | —CH₃ | [4-CH₃-phenyl] | O |
| 4-Cl | —CH₂—[phenyl] | [4-CH₃-phenyl] | O |

TABLE 11-continued
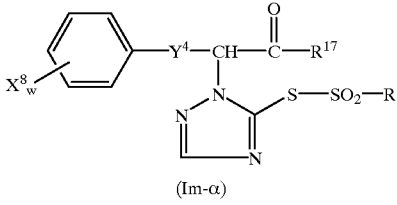
(Im-α)
and
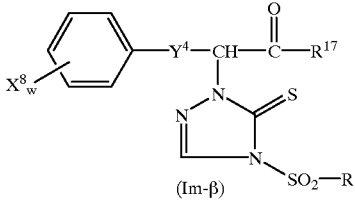
(Im-β)
| $X^8_w$ | $R^{17}$ | R | $Y^4$ |
|---|---|---|---|
| 4-CF$_3$ | —C(CH$_3$)$_3$ | 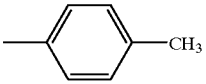 | O |
| 4-OCF$_3$ | —C(CH$_3$)$_3$ | 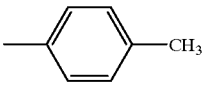 | O |
| 2-OCHF$_2$ | —C(CH$_3$)$_3$ | 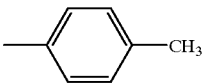 | O |
| 4-OCH$_3$ | —C(CH$_3$)$_3$ | 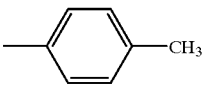 | O |
| 4-Cl | 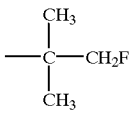 | —CH$_3$ | O |
| 4-Cl | 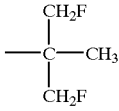 | —CH$_3$ | O |
| 4-Cl | 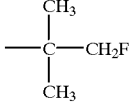 | 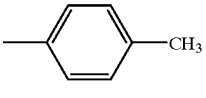 | O |
| 4-Cl | 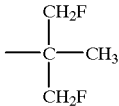 | 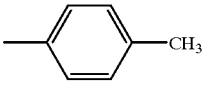 | O |

TABLE 11-continued

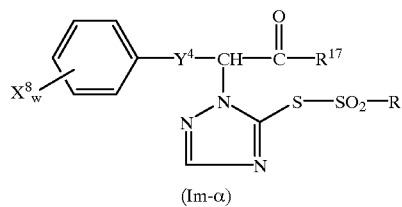

(Im-α)

and

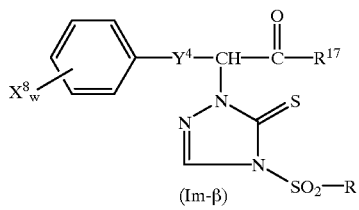

(Im-β)

| $X^8_w$ | $R^{17}$ | R | $Y^4$ |
|---|---|---|---|
| 2,4-Cl$_2$ | ![phenyl] | —CH$_3$ | CH$_2$ |
| 4-Cl | ![phenyl] | —CH$_3$ | CH$_2$ |
| 4-Br | —C(CH$_3$)$_3$ | —CH$_3$ | CH$_2$ |
| — | —C(CH$_3$)$_3$ | —CH$_3$ | CH$_2$ |
| 4-C(CH$_3$)$_3$ | —C(CH$_3$)$_3$ | —CH$_3$ | CH$_2$ |
| 2-Cl | —C(CH$_3$)$_3$ | —CH$_3$ | CH$_2$ |
| 3-Cl | —C(CH$_3$)$_3$ | —CH$_3$ | CH$_2$ |
| 4-F | —C(CH$_3$)$_3$ | —CH$_3$ | CH$_2$ |
| 4-phenyl | —C(CH$_3$)$_3$ | —CH$_3$ | CH$_2$ |
| 2-phenyl | —C(CH$_3$)$_3$ | —CH$_3$ | CH$_2$ |
| 2,4-Cl$_2$ | —C(CH$_3$)$_3$ | —CH$_3$ | CH$_2$ |
| 2-CH$_3$, 4-Cl | —C(CH$_3$)$_3$ | —CH$_3$ | CH$_2$ |
| 3,4-(CH$_3$)$_2$ | —C(CH$_3$)$_3$ | —CH$_3$ | CH$_2$ |
| 2,4,5-Cl$_3$ | —C(CH$_3$)$_3$ | —CH$_3$ | CH$_2$ |
| 4-Cl | —CH$_3$ | —CH$_3$ | CH$_2$ |
| 4-Cl | —CH$_2$-phenyl | —CH$_3$ | CH$_2$ |
| 4-CF$_3$ | —C(CH$_3$)$_3$ | —CH$_3$ | CH$_2$ |
| 4-OCF$_3$ | —C(CH$_3$)$_3$ | —CH$_3$ | CH$_2$ |
| 2-OCHF$_2$ | —C(CH$_3$)$_3$ | —CH$_3$ | CH$_2$ |
| 4-OCH$_3$ | —C(CH$_3$)$_3$ | —CH$_3$ | CH$_2$ |

TABLE 11-continued
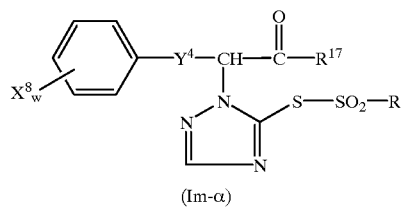
(Im-α)
and
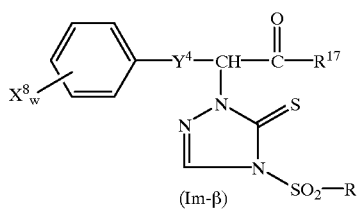
(Im-β)
| $X^8_w$ | $R^{17}$ | R | $Y^4$ |
|---|---|---|---|
| 2,4-Cl$_2$ | —C$_6$H$_5$ | 4-CH$_3$-C$_6$H$_4$ | CH$_2$ |
| 4-Cl | —C$_6$H$_5$ | 4-CH$_3$-C$_6$H$_4$ | CH$_2$ |
| 4-Br | —C(CH$_3$)$_3$ | 4-CH$_3$-C$_6$H$_4$ | CH$_2$ |
| — | —C(CH$_3$)$_3$ | 4-CH$_3$-C$_6$H$_4$ | CH$_2$ |
| 4-C(CH$_3$)$_3$ | —C(CH$_3$)$_3$ | 4-CH$_3$-C$_6$H$_4$ | CH$_2$ |
| 2-Cl | —C(CH$_3$)$_3$ | 4-CH$_3$-C$_6$H$_4$ | CH$_2$ |
| 3-Cl | —C(CH$_3$)$_3$ | 4-CH$_3$-C$_6$H$_4$ | CH$_2$ |
| 4-F | —C(CH$_3$)$_3$ | 4-CH$_3$-C$_6$H$_4$ | CH$_2$ |

TABLE 11-continued (Im-α)

and (Im-β)

| $X^8_w$ | $R^{17}$ | R | $Y^4$ |
|---|---|---|---|
| 4-phenyl | —C(CH$_3$)$_3$ | 4-CH$_3$-phenyl | CH$_2$ |
| 2-phenyl | —C(CH$_3$)$_3$ | 4-CH$_3$-phenyl | CH$_2$ |
| 2,4-Cl$_2$ | —C(CH$_3$)$_3$ | 4-CH$_3$-phenyl | CH$_2$ |
| 2-CH$_3$, 4-Cl | —C(CH$_3$)$_3$ | 4-CH$_3$-phenyl | CH$_2$ |
| 3,4-(CH$_3$)$_2$ | —C(CH$_3$)$_3$ | 4-CH$_3$-phenyl | CH$_2$ |
| 2,4,5-Cl$_3$ | —C(CH$_3$)$_3$ | 4-CH$_3$-phenyl | CH$_2$ |
| 4-Cl | —CH$_3$ | 4-CH$_3$-phenyl | CH$_2$ |
| 4-Cl | —CH$_2$-phenyl | 4-CH$_3$-phenyl | CH$_2$ |
| 4-CF$_3$ | —C(CH$_3$)$_3$ | 4-CH$_3$-phenyl | CH$_2$ |

TABLE 11-continued
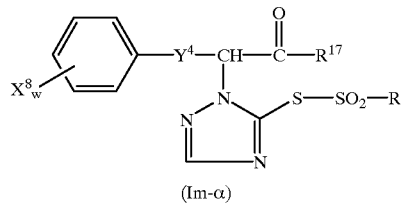
(Im-α)
and
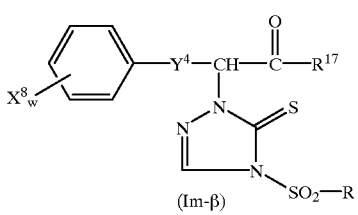
(Im-β)
| $X^8_w$ | $R^{17}$ | R | $Y^4$ |
|---|---|---|---|
| 4-OCF$_3$ | —C(CH$_3$)$_3$ | 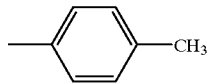 4-methylphenyl | CH$_2$ |
| 2-OCHF$_2$ | —C(CH$_3$)$_3$ | 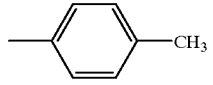 4-methylphenyl | CH$_2$ |
| 4-OCH$_3$ | —C(CH$_3$)$_3$ | 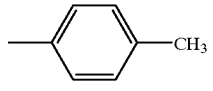 4-methylphenyl | CH$_2$ |
| 4-Cl | —C(CH$_3$)$_2$CH$_2$F | —CH$_3$ | CH$_2$ |
| 4-Cl | —C(CH$_2$F)$_2$CH$_3$ | —CH$_3$ | CH$_2$ |
| 4-Cl | —C(CH$_3$)$_2$CH$_2$F | 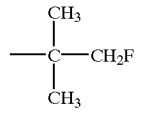 4-methylphenyl | CH$_2$ |
| 4-Cl | —C(CH$_2$F)$_2$CH$_3$ | 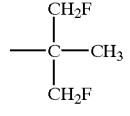 4-methylphenyl | CH$_2$ |
| 4-Cl | —C(CH$_3$)$_3$ | —CH$_3$ | O |
| 4-Cl | —C(CH$_3$)$_3$ | 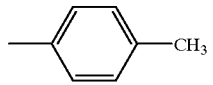 4-methylphenyl | O |

TABLE 12

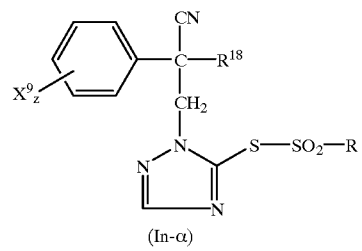
(In-α)

and

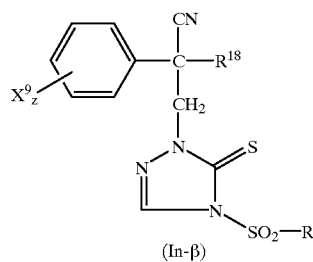
(In-β)

| $X^9_z$ | $R^{18}$ | R |
|---|---|---|
| 4-Cl | —C$_4$H$_9$-n | —CH$_3$ |
| 2-Cl | —C$_4$H$_9$-n | —CH$_3$ |
| 2,4-Cl$_2$ | —C$_4$H$_9$-n | —CH$_3$ |
| 4-Br | —C$_4$H$_9$-n | —CH$_3$ |
| 4-F | —C$_4$H$_9$-n | —CH$_3$ |
| 4-C(CH$_3$)$_3$ | —C$_4$H$_9$-n | —CH$_3$ |
| 4-C$_6$H$_5$ | —C$_4$H$_9$-n | —CH$_3$ |
| 4-Cl | —C(CH$_3$)$_3$ | —CH$_3$ |
| 2-Cl | —C(CH$_3$)$_3$ | —CH$_3$ |
| 2,4-Cl$_2$ | —C(CH$_3$)$_3$ | —CH$_3$ |
| 2,4,6-Cl$_3$ | —C(CH$_3$)$_3$ | —CH$_3$ |
| 4-CF$_3$ | —C(CH$_3$)$_3$ | —CH$_3$ |
| 2-OCHF$_2$ | —C(CH$_3$)$_3$ | —CH$_3$ |
| 4-Cl | —C(CH$_3$)$_2$CH$_2$F | —CH$_3$ |
| 4-Cl | —C(CH$_3$)$_2$CH$_2$F | —CH$_3$ |
| 4-Cl | —CH$_2$-C$_6$H$_4$-4-Cl | —CH$_3$ |
| 4-Cl | —CH(CH$_3$)-C$_6$H$_4$-4-Cl | —CH$_3$ |
| 4-Cl | —CH$_2$-C$_6$H$_4$-4-Cl | —CH$_3$ |

TABLE 12-continued $$\text{(In-}\alpha\text{)}$$

structure: X⁹_z-substituted phenyl-C(CN)(R¹⁸)-CH₂-N(triazole with S-SO₂-R)

and $$\text{(In-}\beta\text{)}$$

structure: X⁹_z-substituted phenyl-C(CN)(R¹⁸)-CH₂-N(triazole-thione with N-SO₂-R)

| X⁹_z | R¹⁸ | R |
|---|---|---|
| 4-Cl | —CH₂—CH₂—(4-Cl-C₆H₄) | —CH₃ |
| — | —CH₂—CH₂—(4-F-C₆H₄) | —CH₃ |
| 4-Cl | —C₄H₉-n | 4-CH₃-C₆H₄— |
| 2-Cl | —C₄H₉-n | 4-CH₃-C₆H₄— |
| 2,4-Cl₂ | —C₄H₉-n | 4-CH₃-C₆H₄— |
| 4-Br | —C₄H₉-n | 4-CH₃-C₆H₄— |
| 4-F | —C₄H₉-n | 4-CH₃-C₆H₄— |
| 4-C(CH₃)₃ | —C₄H₉-n | 4-CH₃-C₆H₄— |
| 4-C₆H₅ | —C₄H₉-n | 4-CH₃-C₆H₄— |

TABLE 12-continued
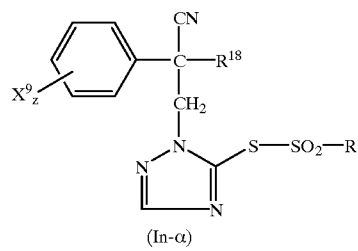
(In-α)
and
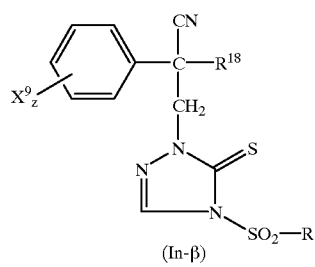
(In-β)
| $X^9_z$ | $R^{18}$ | R |
|---|---|---|
| 4-Cl | —C(CH₃)₃ | —C₆H₄—CH₃ |
| 2-Cl | —C(CH₃)₃ | —C₆H₄—CH₃ |
| 2,4-Cl₂ | —C(CH₃)₃ | —C₆H₄—CH₃ |
| 2,4,6-Cl₃ | —C(CH₃)₃ | —C₆H₄—CH₃ |
| 4-CF₃ | —C(CH₃)₃ | —C₆H₄—CH₃ |
| 2-OCHF₂ | —C(CH₃)₃ | —C₆H₄—CH₃ |
| 4-Cl | —C(CH₃)(CH₃)(CH₂F) | —C₆H₄—CH₃ |
| 4-Cl | —C(CH₂F)(CH₃)(CH₂F) | —C₆H₄—CH₃ |

TABLE 12-continued

Structure (In-α):

Ar(X⁹_z)—C(CN)(R¹⁸)—CH₂—N(triazole)—S—SO₂—R $$\text{(In-}\alpha\text{)}$$

and

Structure (In-β): triazole-thione with N—SO₂—R $$\text{(In-}\beta\text{)}$$

| $X^9_z$ | $R^{18}$ | R |
|---|---|---|
| 4-Cl | —CH₂—C₆H₄—4-Cl | —C₆H₄—4-CH₃ |
| 4-Cl | —CH(CH₃)—C₆H₄—4-Cl | —C₆H₄—4-CH₃ |
| 4-Cl | —C₆H₄—4-Cl | —C₆H₄—4-CH₃ |
| 4-Cl | —CH₂—CH₂—C₆H₄—4-Cl | —C₆H₄—4-CH₃ |
| — | —CH₂—CH₂—(pyridyl)—Cl | —C₆H₄—4-CH₃ |
| — | —CH₂—CH₂—C₆H₄—4-F | —C₆H₄—4-CH₃ |
| — | —CH₂—CH₂—(pyridazinyl)—Cl | —C₆H₄—4-CH₃ |

Using 2-(1-chloro-cyclopropyl)-1-(2-chlorophenyl)-3-(5-mercapto-1,2,4-triazol-1-yl)-propan-2-ol as starting material and methanesulphonyl chloride as reaction component, the course of the process according to the invention can be illustrated by the equation below.

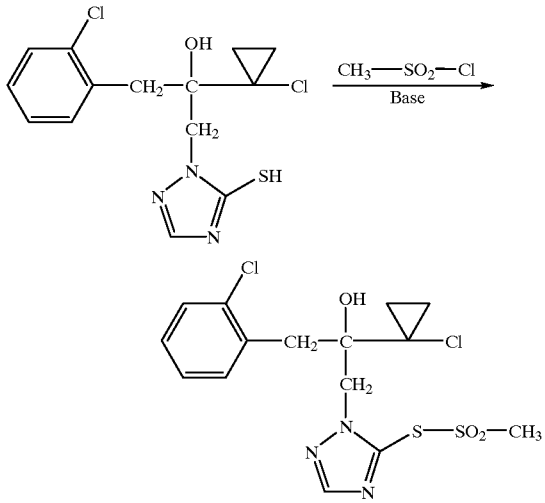

If the mercapto-triazole used as starting material reacts in the "thiono" form, the course of the process according to the invention can be illustrated by the equation below.

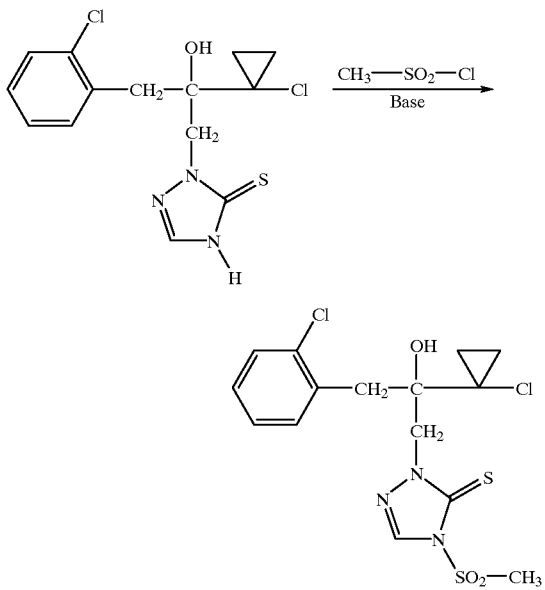

The formulae (II-α) and (II-β) provide a general definition of the mercapto-triazoles required as starting materials for carrying out the process according to the invention. They can be present in the "mercapto" form (II-α) or in the "thiono" form (II-β). However, for simplicity, only the "mercapto" form is mentioned hereinbelow.

In the formulae (II-α) and (II-β), $R^1$ preferably has those meanings which have already been mentioned in connection with the description of the substances of the formula (I-α) or (I-β) according to the invention as being preferred for this radical.

Some of the mercapto-triazoles of the formulae (II-α) or (II-β) are known (cf. WO 87-06 430). They can be prepared by reacting triazoles of the formula

in which
$R^1$ is as defined above
either
α) successively with strong bases and sulphur in the presence of a diluent, followed by hydrolysis with water, if appropriate in the presence of an acid,
or
β) with sulphur in the presence of a high-boiling diluent, followed, if appropriate, by treatment with water and, if appropriate, with acid.

The formula (IV) provides a general definition of the triazoles required as starting materials for carrying out the process for preparing mercapto-triazoles of the formula (II-α) or (II-β). In this formula, $R^1$ preferably has those meanings which have already been mentioned in connection with the description of the substances of the formula (I-α) or (I-β) according to the invention as being preferred for this radical.

The triazoles of the formula (IV) are known or can be prepared by known methods (cf. EP-A 0 015 756, EP-A 0 040 345, EP-A 0 052 424, EP-A 0 061 835, EP-A 0 297 345, EP-A 0 094 564,EP-A 0 196 038,EP-A 0 267 778, EP-A 0 378 953,EP-A 0 068 813, EP-A 0 044 605, EP-A 0 069 442, EP-A 0 055 833, EP-A 0 301 393,DE-A 2 324 010, DE-A 2 737 489, DE-A 2 551 560, EP-A 0 065 485, DE-A 2 735 872, EP-A 0 234 242, DE-A 2 201 063, EP-A 0 145 294 and DE-A 3 721 786).

Suitable bases for carrying out the above process (α) for preparing mercaptotriazoles of the formula (II-α) or (II-β) are all strong alkali metal bases which are customary for such reactions. Preference is given to using n-butyl-lithium, lithium diisopropyl-amide, sodium hydride, sodium amide and also potassium tert-butoxide as a mixture with tetramethylethylene-diamine (=TMEDA).

Suitable diluents for carrying out the above process (α) for preparing mercapto-triazoles of the formula (II-α) or (II-β) are all inert organic solvents which are customary for such reactions. Preference is given to using ethers, such as tetrahydrofuran, dioxane, diethyl ether and 1,2-dimethoxyethane, furthermore liquid ammonia or else strongly polar solvents, such as dimethyl sulphoxide.

Both when carrying out the above process (α) and also the process (β), sulphur is preferably employed in the form of a powder.

When carrying out the above process (α), water, if appropriate in the presence of an acid, is employed for hydrolysis. Suitable acids here are all inorganic or organic acids which are customary for such reactions. Preference is given to using acetic acid, dilute sulphuric acid and dilute hydrochloric acid. However, it is also possible to carry out the hydrolysis using aqueous ammonium chloride solution.

When carrying out the above process (α), the reaction temperatures can be varied within a certain range. In general, the process is carried out at temperatures between −70° C. and +20° C., preferably between −70° C. and 0° C.

The above processes (α) and (β) are generally carried out under atmospheric pressure. However, it is also possible to operate under elevated or reduced pressure. Thus, in particular when carrying out the process (β), operation under elevated pressure is possible.

When carrying out the above process (α), generally 2 to 3 equivalents, preferably 2.0 to 2.5 equivalents, of strong base and subsequently an equivalent amount or else an excess of sulphur are employed per mole of triazole of the formula (IV). The reaction can be carried out under an atmosphere of protective gas, for example under nitrogen or argon. Work-up is carried out by customary methods. In general, the reaction mixture is extracted with an organic solvent which is only sparingly soluble in water, the combined organic phases are dried and concentrated and the residue that remains is, if appropriate, purified by recrystallization and/or chromatography.

Suitable diluents for carrying out the above process (β) are all high-boiling organic solvents which are customary for such reactions. Preference is given to using amides, such as dimethylformamide and dimethylacetamide, moreover heterocyclic compounds, such as N-methyl-pyrrolidone, and also ethers, such as diphenyl ether.

When carrying out the above process (β), a treatment with water and, if appropriate, with acid, can be carried out, if appropriate, after the reaction. This treatment is carried out like the hydrolysis in the practice of the process (α).

When carrying out the above process (β), the reaction temperatures can also be varied within a relatively large range. In general, the reaction is carried out at temperatures between 150° C. and 300° C., preferably between 180° C. and 250° C.

When carrying out the above process (β), generally 1 to 5 mol, preferably 1.5 to 3 mol, of sulphur are employed per mole of triazole of the formula (IV). Work-up is carried out by customary methods. In general, the reaction mixture is extracted with an organic solvent which is only sparingly soluble in water, the combined organic phases are dried and concentrated and the residue that remains is, if appropriate, freed of any impurities that may be present using customary methods, such as recrystallization or chromatography.

The formula (III) provides a general definition of the sulphonyl halides required as reaction components for carrying out the process according to the invention. In this formula, R preferably has those meanings which have already been mentioned in connection with the description of the substances of the formula (I-α) or (I-β) according to the invention as being preferred for this radical. Hal also preferably represents chlorine or bromine.

The sulphonyl halides of the formula (III) are known or can be prepared by known methods.

Suitable acid binders for carrying out the process according to the invention are all customary inorganic or organic bases. Preference is given to using alkali metal hydrides, such as lithium hydride or sodium hydride, furthermore alkaline earth metal hydroxides or alkali metal hydroxides such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal acetates or alkaline earth metal acetates such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

Suitable diluents for carrying out the process according to the invention are all customary inert organic solvents. Preference is given to using aromatic hydrocarbons, such as toluene, xylene or decalin, furthermore halogenated hydrocarbons, such as dichloromethane, chloroform, carbon tetrachloride, dichloroethane or trichloroethane, moreover ethers, such as diethyl ether, diisopropyl ether, methyl tert-butyl ether, methyl tert-amyl ether, dioxane or tetrahydrofuran, and furthermore nitriles, such as acetonitrile, propionitrile, n- or isobutyronitrile.

When carrying out the process according to the invention, the reaction temperatures can be varied within a relatively large range. In general, the process is carried out at temperatures between –20° C. and +100° C., preferably at temperatures between 0° C. and +80° C.

The process according to the invention is generally carried out under atmospheric pressure. However, it is also possible to operate under elevated or reduced pressure.

When carrying out the process according to the invention, generally 1 to 2 mol of sulphonyl halide of the formula (III) and an equivalent amount or else an excess of acid binder are employed per mole of mercapto-triazole of the formula (II-α) or (II-β). Work-up is carried out by customary methods. In general, the reaction mixture, if appropriate after prior addition of an organic solvent which is only sparingly miscible with water, is extracted with saturated aqueous ammonium chloride solution, the organic phase is dried and concentrated under reduced pressure. The resulting product can be freed, if appropriate, of any impurities that may still be present using customary methods, for example recrystallization or chromatography.

The sulphonyl-mercapto-triazolyl derivatives of the formula (I-α) or (I-β) obtainable by the process according to the invention can be converted into acid addition salts or metal salt complexes.

Suitable acids for the preparation of acid addition salts of the compounds of the formula (I-α) or (I-β) are preferably those which have already been mentioned in connection with the description of the acid addition salts according to the invention as being preferred acids.

The acid addition salts of the compounds of the formula (I-α) or (I-β) can be obtained in a simple manner by customary salt formation methods, for example by dissolving a compound of the formula (I-α) or (I-β) in a suitable inert solvent and adding the acid, for example hydrochloric acid, and they can be isolated in a known manner, for example by filtering off, and, if appropriate, purified by washing with an inert organic solvent.

Suitable salts for the preparation of metal salt complexes of the compounds of the formula (I-α) or (I-β) are preferably those of metals which have already been mentioned in connection with the description of the metal salt complexes according to the invention as being preferred metal salts.

The metal salt complexes of the compounds of the formula (I-α) or (I-β) can be obtained in a simple manner by customary processes, for example by dissolving the metal salt in alcohol, for example ethanol, and adding the solution to compounds of the formula (I-α) or (I-β). Metal salt complexes can be isolated in a known manner, for example by filtering off, and, if appropriate, purified by recrystallization.

The active substances according to the invention have strong microbicidal activity and can be employed for controlling undesirable microorganisms, such as fungi and bacteria, in crop protection and in the protection of materials.

In crop protection, fungicides are employed for controlling Plasmodiophoromycetes, Oomycetes, Chytridiomycetes, Zygomycetes, Ascomycetes, Basidiomycetes, Deuteromycetes.

Some causative organisms of fungal and bacterial diseases which come under the generic names listed above may be mentioned as examples, but not by way of limitation:
Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea;*
(conidia form: Drechslera, syn: Helminthosporium);
Cochliobolus species, such as *Cochliobolus sativus;*
(conidia form: Drechslera, syn: Helminthosporium);
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae;*
Pseudocercosporella species, such as *Pseudocercosporella herpotrichoides.*

The good toleration, by plants, of the active substances, at the concentrations required for controlling plant diseases, permits treatment of above-ground parts of plants, of vegetative propagation stock and seeds, and of the soil.

The active substances according to the invention are particularly suitable for controlling *Pyricularia oryzae* and *Pellicularia sasakii* on rice, and also for controlling cereal diseases, such as Pseudocercosporella, Erysiphe species and Fusarium species. Moreover, the substances according to the invention can also be used effectively against Venturia and Sphaerotheca. Additionally, they also have very good in vitro activity.

In the protection of materials the substances according to the invention can be used to protect industrial materials against infestation and destruction by undesirable microorganisms.

The term industrial materials in the present context refers to nonliving materials which have been prepared for use in industry. Examples can be industrial materials which are to be protected by novel active substances against microbial alteration or destruction, adhesives, sizes, paper and card, textiles, leather, wood, coating compositions and plastics articles, cooling lubricants and other materials which can be infested or decomposed by microorganisms. In the context of the materials to be protected mention may also be made of parts of production plants, for example cooling water circuits, which may be adversely affected by reproduction of microorganisms. Preferred industrial materials in the context of the present invention are adhesives, sizes, papers and cards, leather, wood, coating compositions, cooling lubricants and heat transfer fluids, especially wood.

Examples of microorganisms which can bring about degradation or an alteration in the industrial materials are bacteria, fungi, yeasts, algae and slime organisms. The active substances according to the invention preferably act against fungi, especially mould fungi, wood-discolouring and wood-destroying fungi (Basidiomycetes) and also against slime organisms and algae.

By way of example, mention may be made of the following genera:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on their respective physical and/or chemical properties, the active substances can be converted into customary formulations, such as solutions, emulsions, suspensions, powders, foams, pastes, granules, aerosols, very fine capsules in polymeric substances and in coating compositions for seed, and also ULV cold-mist and warm-mist formulations.

These formulations are prepared in a known manner, for example by mixing the active substances with extenders, that is, liquid solvents, liquefied gases under pressure, and/or solid carriers, optionally with the use of surface-active agents, that is, emulsifying agents and/or dispersing agents, and/or foam-forming agents. If the extender used is water, it is also possible to employ, for example, organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water; by liquefied gaseous extenders or carriers are meant liquids which are gaseous at ambient temperature and under atmospheric pressure, for example aerosol propellants, such as butane, propane, nitrogen and carbon dioxide; suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and also granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Possible further additives are mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 percent by weight of active compound, preferably between 0.5 and 90%.

The active substances according to the invention, when used in crop protection, can be used as such or in their formulations as a mixture with known fungicides, bactericides, acaricides, nematicides or insecticides, for example so as to widen the spectrum of action or to prevent the build-up of resistance. In many cases, synergistic effects are obtained, i.e. the efficacy of the mixture is higher than the efficacy of the individual components.

Suitable components for the mixtures are, for example, the following substances:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, toiclophos-methyl, tolylfluanid, triadimefon, triadimenol, triazoxide, trichiamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Imsecticides/acancides/nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis,* bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenfos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, suiprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active substances, such as herbicides, or with fertilizers and growth regulators, is also possible.

The active substances can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active substances by the ultra-low volume method or to inject the active substance formulation or the active substance itself into the soil. The seeds of the plants can also be treated.

In the treatment of parts of plants, the concentrations of active substance in the use forms can be varied within a relatively large range: they are in general between 1 and 0.0001% by weight, preferably between 0.5 and 0.001% by weight.

In the treatment of seed, amounts of active substance of from 0.001 to 50 g per kilogram of seed, preferably from 0.01 to 10 g, are generally required.

In the case of the treatment of soil, active-substance concentrations of from 0.00001 to 0.1% by weight, preferably from 0.0001 to 0.02% by weight, are required at the site of action.

The compositions used for protecting industrial materials comprise the active substances in an amount of in general from 1 to 95%, preferably from 10 to 75%.

The concentrations in which the novel active substances are applied depend on the nature and on the incidence of the microorganisms to be controlled and on the composition of the material to be protected. The optimum amount for use can be determined by means of test series. In general, the use concentrations are in the range from 0.001 to 5% by weight, preferably from 0.05 to 1.0% by weight, based on the material to be protected.

The effectiveness and the spectrum of action of the active substances to be used in the protection of materials in accordance with the invention and of the compositions, concentrates or, very generally, formulations which can be prepared therefrom can be increased by adding, if desired, further antimicrobially active compounds, fungicides, bactericides, herbicides, insecticides or other active substances to increase the spectrum of action or to achieve particular effects, for example additional protection against insects. These mixtures may possess a broader spectrum of action than the compounds according to the invention.

The preparation and the use of the substances according to the invention is illustrated by the examples below.

PREPARATION EXAMPLES

Example 1

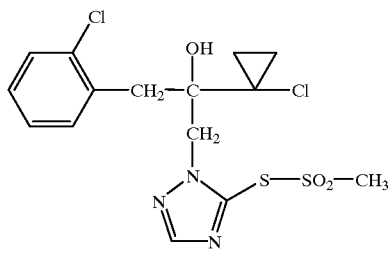
(I-1α)

and

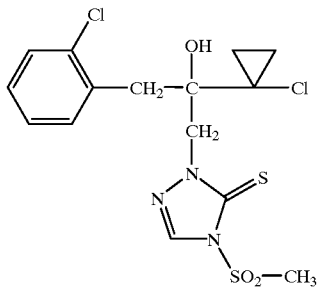
(I-1β)

At 0° C., a mixture of 1.72 g (5 mmol) of 2-(1-chloro-cyclopropyl)-1-(2-chloro-phenyl)-3-(5-mercapto-1,2,4-triazol-1-yl)-propan-2-ol and 0.84 ml (6 mmol) of triethylamine in 20 ml of absolute tetrahydrofuran is admixed with stirring with 0.68 g (6 mmol) of methanesulphonyl chloride. After the addition, stirring is continued at 0° C. for a further 2 hours, and the mixture is then diluted with ethyl acetate. The reaction mixture is extracted repeatedly with saturated aqueous ammonium chloride solution. The organic phase is dried over sodium sulphate and concentrated under reduced pressure. In this manner, 2.05 g (97% of theory) of a solid which comprises 2 parts by weight of 2-(1-chloro-cyclopropyl)-1-(2-chloro-phenyl)-3-(5-methanesulphonyl-mercapto-1,2,4-triazol-1-yl)-propan-2-ol and 1 part by weight of 2-(1-chloro-cyclopropyl)-1-(2-chloro-phenyl)-3-(4-methanesulphonyl-5-thiono-4,5-dihydro-1,2,4-triazol-1-yl)-propan-2-ol are obtained.

$^1$H NMR spectrum of the compound (I-1α) (400 MHz; CDCl$_3$; TMS): δ=0.5–0.95 (m, 4H); 3.15.(d, 1H); 3.6 (s, 3H); 3.62 (d, 1H); 4.7 (d, 1H); 5.15 (d, 1H); 7.2–7.55 (m, 4H); 8.1 (s, 1H) ppm.

$^1$H NMR spectrum of the compound (I-1β) (400 MHz; CDCl$_3$; TMS): δ=0.5–0.95 (m, 4H); 3.1 (d, 1H); 3.1 (s, 3H); 3.15 (d, 1H); 4.05 (d, 1H); 5.0 (d, 1H); 7.2–7.55 (m, 4H); 8.05 (s, 1H) ppm.

The substances listed in the examples below are also prepared in the manner indicated above.

Example 2

(I-2α)

-continued (I-2β)

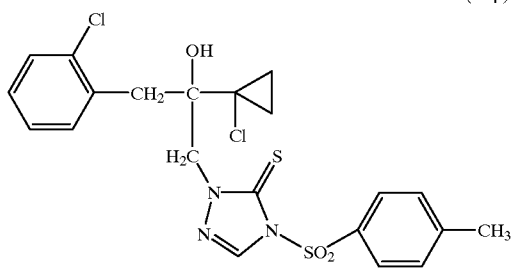

¹H NMR spectrum of the compound (I-2α) (200 MHz, CDCl₃, TMS): δ=0.4–1.0 (m, 4H); 2.5 (s, 3H); 3.05 (d, 1H); 3.7 (d, 1H); 4.1 (d, 1H); 5.0 (d, 1H); 7.2–7.6 m (8H), 8.1 (s, 1H) ppm ¹H NMR spectrum of the compound (I-2β) (200 MHz, CDCl₃, TMS): δ=0.4–1.0 (m, 4H); 2.4 (s, 3H); 3.1 (d, 1H); 3.6 (d, 1H); 4.15 (d, 1H); 4.95 (d, 1H); 7.2–7.6 (m, 8H), 7.95 (s, 1H) ppm Example 3

(I-3α)

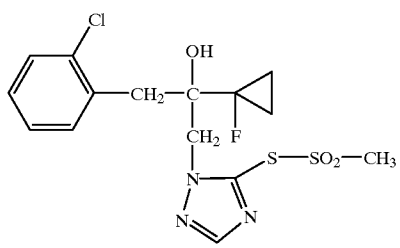

(I-3β)

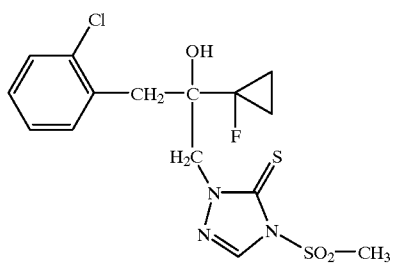

¹H NMR spectrum of the compound (I-3α) (200 MHz, CDCl₃, TMS): δ=0.1–0.9 (m, 4H); 3.15 (d, 1H); 3.45 (d, 1H); 3.75 (s, 3H); 4.6 (AB); 7.2–7.5 (m, 4H), 8.2 (s, 1H) ppm ¹H NMR spectrum of the compound (I-3β) (200 MHz, CDCl₃, TMS): δ=0.1–0.9 (m, 4H); 3.15 (d, 1H); 3.45 (d, 1H); 3.6 (s, 3H); 4.3 (d, 1H); 5.0 (d, 1H); 7.2–7.5 (m, 4H), 8.1 (s, 1H) ppm Preparation of starting materials Example 4

(II-1)

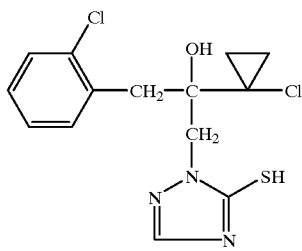

Variant α:

At −20° C., a mixture of 3.12 g (10 mmol) of 2-(1-chloro-cyclopropyl)-1-(2-chlorophenyl)-3-(1,2,4-triazol-1-yl)-propan-2-ol and 45 ml of absolute tetrahydrofuran is admixed with 8.4 ml (21 mmol) of n-butyl-lithium in hexane and stirred at 0° C. for 30 minutes. The reaction mixture is subsequently cooled to −70° C., admixed with 0.32 g (10 mmol) of sulphur powder and stirred at −70° C. for 30 minutes. The mixture is warmed to −10° C., admixed with ice-water and adjusted to pH 5 by addition of dilute sulphuric acid. The mixture is extracted repeatedly with ethyl acetate and the combined organic phases are dried over sodium sulphate and concentrated under reduced pressure. In this manner, 3.2 g (93% of theory) of 2-(1-chloro-cyclopropyl)-1-(2-chlorophenyl)-3-(5-mercapto-1,2,4-triazol-1-yl)-propan-2-ol are obtained in the form of a solid substance which, after recrystallization, melts at 138–139° C.

Variant β:

With stirring, a mixture of 3.12 g (10 mmol) of 2-(1-chloro-cyclopropyl)-1-(2-chlorophenyl)-3-(1,2,4-triazol-1-yl)-propan-2-ol, 0.96 g (30 mmol) of sulphur powder and 20 ml of absolute N-methyl-pyrrolidone is heated at 200° C. for 44 hours. The reaction mixture is subsequently concentrated under reduced pressure (0.2 mbar). The resulting crude product (3.1 g) is recrystallized from toluene. In this manner, 0.7 g (20% of theory) of 2-(1-chloro-cyclopropyl)-1-(2-chlorophenyl)-3-(5-mercapto-1,2,4-triazol-1 -yl)-propan-2-ol is obtained in the form of a solid substance of melting point 138–139° C.

Example 5

(II-2)

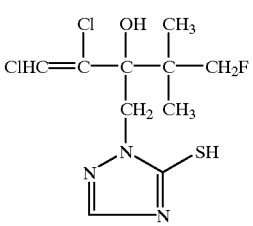

At −70° C., a mixture of 1.41 g (5 mmol) of 1,2-dichloro-4,4-dimethyl-5-fluoro-3-hydroxy-3-[(1,2,4-triazol-1-yl)-methyl]-1-pentene and 25 ml of absolute tetrahydrofuran is admixed with 4 ml (10 mmol) of n-butyl-lithium in hexane and stirred at −70° C. for one hour. The reaction mixture is then admixed with 0.19 g (6 mmol) of sulphur powder and stirred at −70° C. for 4 hours. The mixture is subsequently hydrolyzed at −70° C. by addition of 1 ml of methanol and 1 ml of acetic acid. The reaction mixture is initially diluted with ethyl acetate and then extracted repeatedly with saturated aqueous ammonium chloride solution. The organic phase is dried over sodium sulphate and concentrated under reduced pressure. The resulting crude product (1.7 g) is purified by silica gel chromatography using a mixture of petroleum ether and ethyl acetate=1:1 as mobile phase. In this manner, 0.5 g (32% of theory) of 1,2-dichloro-4,4-dimethyl-5-fluoro-3-hydroxy-3-[(5-mercapto-1,2,4-triazol-1-yl)-methyl]-1-pentene is obtained in the form of a solid substance of melting point 162–164° C.

The compounds listed in Table 13 below are also prepared using the methods given in Examples 4 and 5.

TABLE 13

(II-a)

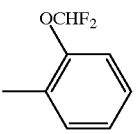

| Ex. No. | Comp. No. | R² | R³ | Physical constant |
|---|---|---|---|---|
| 6 | (II-3) | —CCl=CHCl | —C(CH₃)₃ | M.p. 168–169° C. |
| 7 | (II-4) | 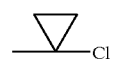 |  | GC/MS (CI):376 (M + H⁺) |
| 8 | (II-5) |  | 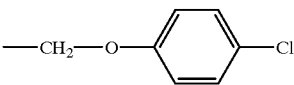 | M.p. 163–164° C. |
| 9 | (II-6) |  | —C(CH₃)₃ | M.p. 127° C. |
| 10 | (II-7) | 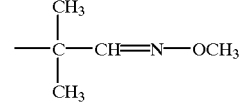 | 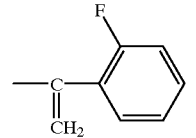 | oil |
| 11 | (II-8) | 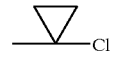 | 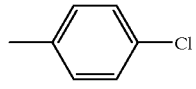 | GC/MS (CI):340 (M + H⁺) |
| 12 | (II-9) | 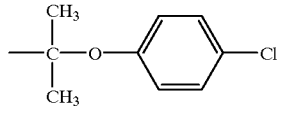 |  | GC/MS (CI):424 (M + H⁺) |
| 13 | (II-10) | 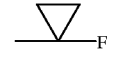 |  | M.p. 168° C. |
| 14 | (II-11) | 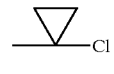 | | GC/MS (CI):314 (M + H⁺) |

TABLE 13-continued (II-a)

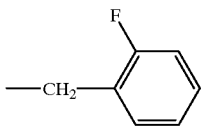

| Ex. No. | Comp. No. | R² | R³ | Physical constant |
|---|---|---|---|---|
| 15 | (II-12) | 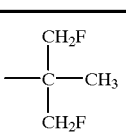 | 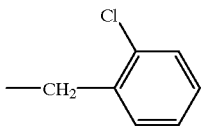 | GC/MS (Cl):346 (M + H⁺) |
| 16 | (II-13) | 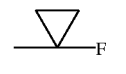 | 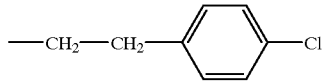 | M.p. 115–118° C. |
| 17 | (II-14) | 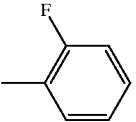 | —C(CH₃)₃ | GC/MS (Cl):340 (M + H⁺) |
| 18 | (II-15) |  | 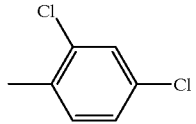 | GC/MS (Cl):334 (M + H⁺) |
| 19 | (II-16) | 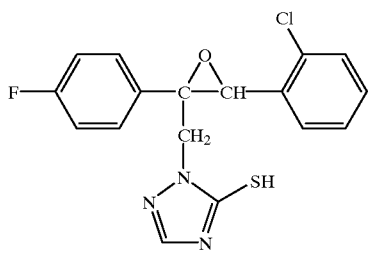 | —C₄H₉-n | *) |

*)The compound is characterized by the following signals in the $^1$H NMR

Example 20

(II-17)

At –70° C., a mixture of 1.3 g (4 mmol) of 3-(2-chlorophenyl)-2-(4-fluoro-phenyl)-2-(1,2,4-triazol-1-yl-methyl)-oxirane (Z form) and 25 ml of absolute tetrahydrofuran is admixed with 2.0 ml (5 mmol) of n-butyl-lithium in hexane and stirred at –70° C. for 1 hour. The reaction mixture is then admixed with 0.16 g (5 mmol) of sulphur powder and stirred at –70° C. for 4 hours. Subsequently, 1 ml of methanol and 1 ml of acetic acid are simultaneously added dropwise with stirring at –70° C. The resulting mixture is diluted with dichloromethane and extracted repeatedly with saturated aqueous ammonium chloride solution. The organic phase is dried over sodium sulphate and then concentrated under reduced pressure. The resulting crude product (1.9 g) which, according to the gas chromatogram, contains 51.0% of the desired product, in addition to 20.7% of starting material, is recrystallized from toluene. In this manner, 0.8 g (55% of theory) of 3-(2-chlorophenyl)-2-(4-fluoro-phenyl)-2-(5-mercapto-1,2,4-triazol-1-yl-methyl)-oxirane (Z form) is obtained as a solid substance of melting point 179 to 180° C.

$^1$H NMR spectrum (200 MHz, CDCl₃, TMS): δ=3.7 (d, J=15 Hz, 1H); 4.1 (s, 1H); 5.15 (d, J=15 Hz, 1H); 6.95–7.6 (m, 8H); 7.65 (s, 1H); 11.0 (s, 1H) ppm.

GC/MS (ci): 362 (M+H⁺)

Example 21

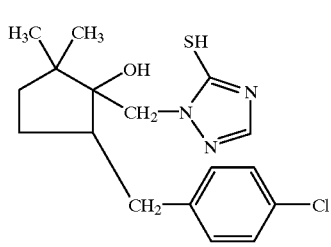

(II-18)

At −20° C., a mixture of 1.6 g (5 mmol) of 5-(4-chlorobenzyl)-2,2-dimethyl-1-(1,2,4-triazol-1-yl-methyl)-cyclopentan-1-ol (Z form) and 30 ml of absolute tetrahydrofuran is admixed with 4 ml (10 mmol) of n-butyl-lithium in hexane, and stirring is continued at 0° C. for 30 minutes. The reaction mixture is subsequently cooled to −70° C., admixed with stirring with 0.19 g (6 mmol) of sulphur powder and then stirred at −70° C. for 1 hour and subsequently at 0° C. for 2 hours, The resulting mixture is diluted with ethyl acetate and extracted repeatedly with saturated aqueous ammonium chloride solution. The organic phase is dried over sodium sulphate and then concentrated under reduced pressure. The resulting crude product (0.2 g) is recrystallized from toluene. In this manner, 1.1 g (63% of theory) of 5-(4-chloro-benzyl)-2,2-dimethyl-1-(5-mercapto-1,2,4-triazol-1-yl-methyl)-cyclopentan-1-ol (Z form) are obtained as a solid substance of melting point 179 to 180° C.

GC/MS (ci): 352 (M+H$^+$)

Example 22

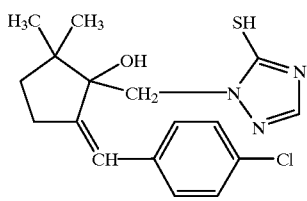

(II-19)

At −20° C., a mixture of 1.59 g (5 mmol) of 2-(4-chlorobenzylidene)-5,5-dimethyl-1-(1,2,4-triazol-1-yl-methyl)-cyclopentan-1-ol and 30 ml of absolute tetrahydrofuran is admixed with 4.4 ml (11 mmol) of n-butyl-lithium in hexane, and stirring is continued at 0° C. for 30 minutes. The reaction mixture is subsequently cooled to −70° C., admixed with stirring with 0.19 g (6 mmol) of sulphur powder and then stirred at −70° C. for 1 hour and subsequently at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (1.9 g) is chromatographed over silica gel using ethyl acetate. In this manner, 0.8 g (46% of theory) of 2-(4-chloro-benzylidene)-5,5-dimethyl-1-(5-mercapto-1,2,4-triazol-1-yl-methyl)-cyclopentan-1-ol is obtained.

$^1$H NMR spectrum (200 MHz, CDCl$_3$; TMS): δ=0.9 (s, 3H); 1.15 (s,3H); 1.6–1.95 (m, 2H); 2.4–3.0 (m, 2H); 4.25 (d, 1H); 4.55 (d, 1H); 5.9 (m, 1H); 7.1–7.3 (m, 4H); 7.6 (s,1H) ppm

Example 23

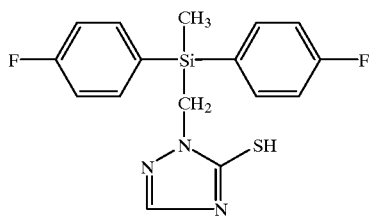

(II-20)

At 0° C., a mixture of 1.58 g (5 mmol) of bis-(4-fluorophenyl)-methyl-(1,2,4-triazol-1-yl-methyl)-silane and 30 ml of absolute tetrahydrofuran is admixed with 2 ml (5 mmol) of n-butyl-lithium in hexane, and stirred at 0° C. for 1 hour. The reaction mixture is subsequently cooled to −70° C., admixed with stirring with 0.16 g (5 mmol) of sulphur powder and then stirred at −70° C. for 1 hour and subsequently at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (1.8 g) is purified by silica gel chromatography using a mixture of petroleum ether and ethyl acetate=1:1 as mobile phase. In this manner, 0.6 g (35% of theory) of bis-(4-fluorophenyl)-methyl-(5-mercapto-1,2,4-triazol-1-yl-methyl)-silane is obtained.

$^1$H NMR spectrum (200 MHz, CDCl$_3$, TMS) δ=0.7 (s, 3H); 4.2 (s, 2H); 7.05 (m, 4H); 7.55 (m, 5H); 13.1 (s, 1H) ppm GC/MS (EI): 347 (M$^+$, 20%)

Example 24

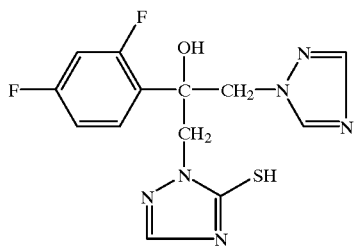

(II-21)

At −20° C., a mixture of 1.53 g (5 mmol) of 2-(2,4-difluoro-phenyl)-1,3-bis-(1,2,4-triazol-1-yl)-propan-2-ol and 30 ml of absolute tetrahydrofuran is admixed with 4.4 ml (11 mmol) of n-butyl-lithium in hexane, and stirring is continued at 0° C. for 30 minutes. The reaction mixture is subsequently cooled to −70° C., admixed with stirring with 0.19 g (6 mmol) of sulphur powder and then stirred at −70° C. for 1 hour and subsequently at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (2.3 g) is purified by silica gel chromatography using a mixture of ethyl acetate and ethanol=9:1 as mobile phase. In this manner, 1.0 g (59% of theory) of 2-(2,4-difluoro-phenyl)-1-(5-mercapto-1,2,4-triazol-1-yl)-3-(1,2,4-triazol-1-yl)-propan-2-ol is obtained in the form of a solid substance of melting point 187° C.

GC/MS (ci): 339 (M+H$^+$)

Example 25

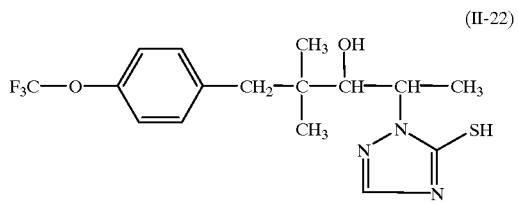
(II-22)

At −20° C., a mixture of 1.72 g (5 mmol) of 2,2-dimethyl-3-hydroxy-4-(1,2,4-triazol-1-yl)-1-(4-trifluoromethoxy-phenyl)-pentane and 30 ml of absolute tetrahydrofuran is admixed with 4.4 ml (11 mmol) of n-butyl-lithium in hexane, and stirring is continued at 0° C. for 30 minutes. The reaction mixture is subsequently cooled to −70° C., admixed with stirring with 0.19 g (6 mmol) of sulphur powder and then stirred at −70° C. for 1 hour and subsequently at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (2.2 g) is purified by silica gel chromatography using a mixture of petroleum ether and ethyl acetate=1:1 as mobile phase. In this manner, 1.4 g (75% of theory) of 2,2-dimethyl-3-hydroxy-4-(5-mercapto-1,2,4-triazol-1-yl)-1-(4-trifluoromethoxy-phenyl)-pentane are obtained in the form of a solid substance of melting point 125 to 126° C.

GC/MS(ci): 376 (M+H$^+$)

Example 26

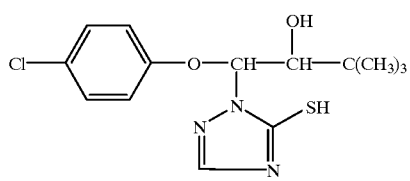
(II-23)

At −20° C., a mixture of 1.48 g (5 mmol) of 1-(4-chloro-phenoxy)-1-(1,2,4-triazol-1-yl)-3,3-dimethyl-butan-2-ol and 30 ml of absolute tetrahydrofuran is admixed with 4 ml (10 mmol) of n-butyl-lithium in hexane, and stirring is continued at −20° C. for 30 minutes. At −20° C., the reaction mixture is then admixed with stirring with 0.19 g (6 mmol) of sulphur powder and then stirred at −20° C. for 1 hour and subsequently at 0° C. for 2 hours. The resulting mixture is diluted with ethyl acetate and extracted repeatedly with saturated aqueous ammonium chloride solution. The organic phase is dried over sodium sulphate and then concentrated under reduced pressure. The resulting crude product (1.9 g) is purified by silica gel chromatography using a mixture of petroleum ether and ethyl acetate=1:1 as mobile phase. In this manner, 0.7 g (43% of theory) of 1-(4chlorophenoxy)-1-(5-mercapto-1,2,4-triazol-1-yl)-3,3-dimethyl-butan-2-ol is obtained in the form of a solid substance of melting point 193 to 194° C.

MS(ci): 328 (M+H$^+$)

Example 27

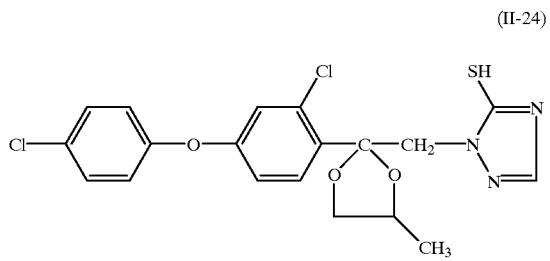
(II-24)

With stirring, a mixture of 2.0 g (5 mmol) of 2-[2-chloro-4-(4-chloro-phenoxy)-phenyl]-2-(1,2,4-triazol-1-yl-methyl)-4-methyl-1,3-dioxolan, 0.32 g (10 mmol) of sulphur powder and 10 ml of absolute N-methylpyrrolidone is heated at 200° C. for 22 hours. The reaction mixture is subsequently concentrated under reduced pressure (0.2 mbar). The residue that remains is admixed with ethyl acetate, and the resulting mixture is extracted repeatedly with saturated aqueous ammonium chloride solution. The organic phase is dried over sodium sulphate and then concentrated under reduced pressure. The resulting crude product (1.8 g) is purified by silica gel chromatography using a mixture of petroleum ether and ethyl acetate=1:1 as mobile phase. In this manner, 0.9 g (41% of theory) of 2-[2-chloro-4-(4-chloro-phenoxy)-phenyl]-2-[(5-mercapto-1,2,4-triazol-1-yl)-methyl]-4-methyl-1,3-dioxolan is obtained in the form of an isomer mixture.

MS (ci): 438 (M+H$^+$, 100%)

Example 28

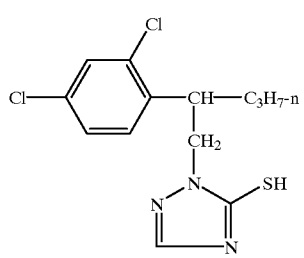
(II-25)

Under an atmosphere of nitrogen and with stirring, a mixture of 1.42 g (5 mmol) of 2-(2,4-dichloro-phenyl)-1-(1,2,4-triazol-1-yl)-pentane, 0.32 g (10 mmol) of sulphur powder and 10 ml of absolute N-methylpyrrolidone is heated at 200° C. for 3 hours. The reaction mixture is subsequently concentrated under reduced pressure. The residue that remains is admixed with ethyl acetate, and the resulting mixture is extracted repeatedly with saturated aqueous ammonium chloride solution. The organic phase is dried over sodium sulphate and then concentrated under reduced pressure. The resulting crude product (2.1 g) is purified by silica gel chromatography using a mixture of petroleum ether and ethyl acetate=1:1 as mobile phase. In this manner, 1.5 g (95% of theory) of 2-(2,4-dichloro-phenyl)-1-(5-mercapto-1,2,4-triazol-1-yl)-pentane are obtained in the form of a solid substance of melting point 103° C.

193
Example 29

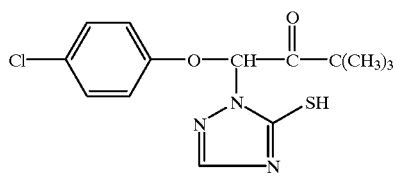
(II-26)

Under an atmosphere of nitrogen and with stirring, a mixture of 2.93 g (10 mmol) of 1-(4-chloro-phenoxy)-1-(1,2,4—triazol-1-yl)-3,3-dimethyl-butan-2-one, 0.64 g (20 mmol) of sulphur powder and 10 ml of absolute N-methylpyrrolidone is heated at 200° C. for 8 hours. The reaction mixture is subsequently concentrated under reduced pressure and the residue that remains is dissolved in dichloromethane. The resulting mixture is extracted repeatedly with saturated aqueous ammonium chloride solution.

The organic phase is dried over sodium sulphate and then concentrated under reduced pressure. The resulting crude product (2.7 g) is purified by silica gel chromatography using a mixture of petroleum ether and ethyl acetate=1:1 as mobile phase. In this manner, 2.0 g (62% of theory) of 1-(4-chlorophenoxy)-1-(5-mercapto-1,2,4-triazol-1-yl)-3,3-dimethyl-butan-2-one are obtained in the form of a solid substance of melting point 134 to 136° C.

Example 30

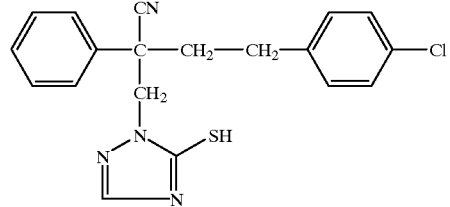
(II-27)

Under an atmosphere of nitrogen and with stirring, a mixture of 1.68 g (5 mmol) of 4-(4-chloro-phenyl)-2-cyano-2-phenyl-1-(1,2,4-triazol-1-yl)-butane, 0.32 g (10 mmol) of sulphur powder and 10 ml of absolute N-methylpyrrolidone is heated at 200° C. for 47 hours. The reaction mixture is subsequently concentrated under reduced pressure, and the residue that remains is dissolved in ethyl acetate. The resulting mixture is extracted repeatedly with saturated aqueous ammonium chloride solution. The organic phase is dried over sodium sulphate and then concentrated under reduced pressure. The resulting crude product (1.9 g) is purified by silica gel chromatography using a mixture of petroleum ether and ethyl acetate=1:1 as mobile phase. In this manner, 0.7 g (38% of theory) of 4-(4-chloro-phenyl)-2-cyano-2-phenyl-1-(5-mercapto-1,2,4-triazol-1-yl)-butane is obtained in the form of an oil.

$^1$H NMR spectrum (400 MHz, CDCl$_3$, TMS): δ=2.4 (m, 3H); 2.75 (m, 1H); 4.5 (AB, 2H); 7.0 (d, 2H); 7.2 (d, 2H); 7.4 (m, 3H); 7.55 (m, 2H); 7.8 (s, 1H); 11.7 (1H) ppm.

194
Example A
Erysiphe test (barley)/protective
Solvent: 10 parts by weight of N-methyl-pyrrolidone
Emulsifier: 0.6 parts by weight of alkylaryl polyglycol ether To produce a suitable preparation of active substance, 1 part by weight of active substance is mixed with the stated amounts of solvent and emulsifier, and the concentrate is diluted with water to the desired concentration.

To test for protective activity, young plants are sprayed with the preparation of active substance at the stated application rate. After the spray coating has dried on, the plants are dusted with spores of *Erysiphe graminis* f.sp. *hordei*.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, while an efficacy of 100% means that no infection is observed.

Active substances, active substance concentrations and test results are shown in the table below.

TABLE A

Erysiphe test (barley)/protective

| Active substance | Application rate of active substance in g/ha | Efficacy in % |
|---|---|---|
| According to the invention: | | |
| (I-1α) + (I-1β) | 250 | 100 |

Example B
Erysiphe test (barley)/curative
Solvent: 10 parts by weight of N-methyl-pyrrolidone
Emulsifier: 0.6 parts by weight of alkylaryl polyglycol ether To produce a suitable preparation of active substance, 1 part by weight of active substance is mixed with the stated amounts of solvent and emulsifier, and the concentrate is diluted with water to the desired concentration.

To test for curative activity, young plants are dusted with spores of *Erysiphe graminis* f.sp. *hordei*. 48 hours after the inoculation, the plants are sprayed with the preparation of active substance at the stated application rate.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the control, while an efficacy of 100% means that no infection is observed.

Active substances, active substance concentrations and test results are shown in the table below.

TABLE B

Erysiphe test (barley)/curative

| Active substance | Application rate of active substance in g/ha | Efficacy in % |
|---|---|---|
| According to the invention: | | |
| (I-1α) + (I-1β) | 250 | 100 |

Example C

Sphaerotheca test (cucumber)/protective/systemic

Solvent: 47 parts by weight of acetone
Emulsifier: 3 parts by weight of alkyl-aryl polyglycol ether To produce a suitable preparation of active substance, 1 part by weight of active substance is mixed with the stated amounts of solvent and emulsifier, and the concentrate is diluted with water to the desired concentration.

To test for protective activity, young plants are sprayed with the preparation of active substance at the stated application rate. After the spray coating has dried on, the plants are inoculated with an aqueous spore suspension of *Sphaerotheca fuliginea*. The plants are placed in a greenhouse at approximately 23° C. and at a relative atmospheric humidity of approximately 70%.

Evaluation is carried out 10 days after the inoculation. 0% means an efficacy which corresponds to that of the control, while an efficacy of 100% means that no infection is observed.

Active substances, active substance concentrations and test results are shown in the table below.

TABLE C

Sphaerotheca test (cucumber)/protective

| Active substance | Application rate of active substance in g/ha | Efficacy in % |
|---|---|---|
| According to the invention: | | |
| (I-1α) + (I-1β) | 50 | 98 |

Example D

Venturia test (apple)/protective

Solvent: 47 parts by weight

Emulsifier: 3 parts by weight

To produce a suitable preparation of active substance, 1 part by weight of active substance is mixed with the stated amounts of solvent and emulsifier, and the concentrate is diluted with water to the desired concentration.

To test for protective activity, young plants are sprayed with the preparation of active substance at the stated application rate. After the spray coating has dried on, the plants are inoculated with an aqueous conidia suspension of the causative organism of apple scab (*Venturia inaequalis*) and then remain in an incubation cabin at 20° C. and 100% relative atmospheric humidity for 1 day.

The plants are then placed in a greenhouse at 21° C. and at a relative atmospheric humidity of approximately 90%.

Evaluation is carried out 12 days after the inoculation. 0% means an efficacy which corresponds to that of the control, while a of 100% means that no infection is observed.

Active substances, active substance concentrations and test results are shown in the table below.

TABLE D

Venturia test (apple)/protective

| Active substance | Application rate of active substance in g/ha | Efficacy in % |
|---|---|---|
| According to the invention: | | |
| (I-1α) + (I-1β) [chlorophenyl-CH₂-C(OH)(cyclopropyl-Cl)-CH₂-triazolyl structures with S-SO₂-CH₃ and SO₂-CH₃ substituents] | 50 | 100 |

Example E

Botrytis test (bean)/protective

Solvent: 47 parts by weight of acetone

Emulsifier: 3 parts by weight of alkyl-aryl polyglycol ether

To produce a suitable preparation of active substance, 1 part by weight of active substance is mixed with the stated amounts of solvent and emulsifier, and the concentrate is diluted with water to the desired concentration.

To test for protective activity, young plants are sprayed with the preparation of active substance at the stated application rate. After the spray coating has dried on, two small pieces of agar overgrown with *Botrytis cinerea* are placed onto each leaf. The inoculated plants are placed in a dark chamber at approximately 20° C. and 100% relative atmospheric humidity.

2 days after the inoculation, the size of the diseased areas on the leaves is evaluated. 0% means an efficacy which corresponds to that of the control, while an efficacy of 100% means that no infection is observed.

Active substances, active substance concentrations and test results are shown in the table below.

TABLE E

Botrytis test (bean)/protective

| Active substance | Application rate of active substance in g/ha | Efficacy in % |
|---|---|---|
| According to the invention: | | |
| (I-1α) + (I-1β) [same structures as in Table D] | 500 | 99 |

What is claimed is:

1. A sulphonyl-mercapto-triazolyl derivative of the formula

(I-α)

or

(I-β)

in which

R represents straight-chain or branched alkyl having 1 to 8 carbon atoms, phenylalkyl having 1 to 4 carbon atoms in the alkyl moiety which is optionally mono- to trisubstituted by identical or different substituents selected from the group consisting of halogen and alkyl having 1 to 4 carbon atoms or represents phenyl which is optionally mono- to trisubstituted by identical or different substituents selected from the group consisting of halogen and alkyl having 1 to 4 carbon atoms, and $R^1$ represents a radical of the formula

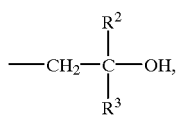

in which $R^2$ represents straight-chain or branched alkyl having 1 to 6 carbon atoms, it being possible for these radicals to be mono- or tetrasubstituted by identical or different substituents selected from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, it being possible for each of these radicals to be mono- to trisubstituted by identical or different substituents selected from the group consisting of halogen, alkoxy having 1 to 4 carbon atoms and cycloalkyl having 3 to 7 carbon atoms, or represents cycloalkyl having 3 to 7 carbon atoms, it being possible for each of these radicals to be mono- or trisubstituted by identical or different substituents selected from the group consisting of halogen, cyano and alkyl having 1 to 4 carbon atoms, or represents aralkyl having 6 to 10 carbon atoms in the aryl moiety and 1 to 4 carbon atoms in the straight chain or branched alkyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 identical or different halogen atoms, halogenoalkyl having 1 to 2 carbon atoms and 1 to 5 identical or different halogen atoms, halogenoalkylthio having 1 to 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, cycloalkyl having 3 to 7 carbon atoms in the phenyl, phenoxy, alkoxycarbonyl having 1 to 4 carbon atoms in the alkoxy moiety, alkoxyiminoalkyl having 1 to 4 carbon atoms in the alkoxy moiety and 1 to 4 carbon atoms in the alkyl moiety, nitro and cyano, or represents aroxyalkyl having 6 to 10 carbon atoms in the aryl moiety and 1 to 4 carbon atoms in the straight-chain or branched oxyalkyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro or cyano, or represents aryl having to 6 to 10 carbon atoms, it being possible for each of these radicals to mono to trisubstituted by identical or different substituents selected from the group consisting of halogen, alkyl having 1 to 4 carbon atoms, alkoxy having 1 to 4 carbon atoms, alkythio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety and 1 to 4 carbon atoms in the alkyl moiety, nitro and cyano, and $R^3$ represents straight-chain or branched alkyl having 1 to 6 carbon atoms, it being possible for these radicals to be mono- to tetrasubstituted by identical or different substituents selected from the group consisting of halogen, alkoxy having 1 to 4 carbon atoms, alkoximino having 1 to 4 carbon atoms in the alkoxy moiety and cycloalkyl having 3 to 7 carbon atoms, or represents straight-chain or branched alkenyl having 2 to 6 carbon atoms, it being possible for each of these radicals to be mono- to tetrasubstituted by identical or different substituents selected from the group consisting of halogen, alkoxy having 1 to 4 carbon atoms and cycloalkyl having 3 to 7 carbon atoms, or represents cycloalkyl having 3 to 7 carbon atoms, it being possible for each of these radicals to be mono- to trisubstituted by identical or different substituents selected from the group consisting of halogen or cyano and alkyl having 1 to 4 carbon atoms, or represents aralkyl having 6 to 10 carbon atoms in the aryl moiety and 1 to 4 carbon atoms in the straight-chain or branched alkyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl or phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or represents aralkenyl having 6 to 10 carbon atoms in the aryl moiety and 2 to 4 carbon atoms in the alkenyl moiety, it being possible for each of the aryl moieties to be mono- or trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano or represents aroxyalkyl having 6 to 10 carbon atoms in the aryl moiety and 1 to 4 carbon atoms in the straight-chain or branched oxyalkyl moiety, it being possible for each of the aryl moieties to be mono- to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety nitro and cyano, or represents aryl having 6 to 10 carbon atoms, it being possible for each of these radicals to be mono- or trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkyl having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and cyano, or an addition product thereof with an acid or metal salt.

2. A microbicidal composition comprising a microbicidally effective amount of a compound or addition product as claimed in claim 1 and an inert diluent.

3. A method for controlling undesired microorganisms in plant protection and in the preservation of materials, which method comprises applying to such undesired microorganisms or to their habitat a microbicidally effective amount of a compound or addition product as claimed in claim 1.

4. a. A microbicidal compound of formula

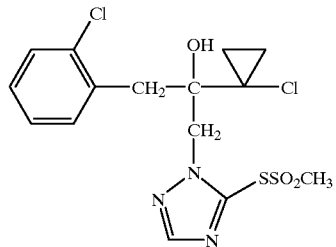

(I-1α)

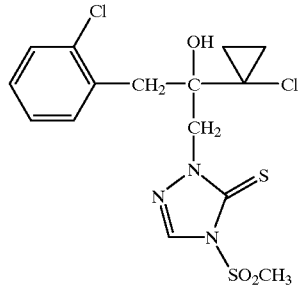

(I-1β)

* * * * *